United States Patent
Chen et al.

(10) Patent No.: US 10,328,054 B2
(45) Date of Patent: Jun. 25, 2019

(54) SUBSTITUTED PYRROLIDINES AS MGLUR5 ANTAGONISTS

(71) Applicant: Hua Medicine (Shanghai) Ltd., Shanghai (CN)

(72) Inventors: Li Chen, Shanghai (CN); Yuejiao Duan, Shanghai (CN); Jin She, Shanghai (CN); Chengde Wu, Shanghai (CN)

(73) Assignee: Hua Medicine (Shanghai) Ltd., Shanghai (CN)

( * ) Notice: Subject to any disclaimer, the term of this patent is extended or adjusted under 35 U.S.C. 154(b) by 0 days.

(21) Appl. No.: 15/771,920

(22) PCT Filed: Oct. 21, 2016

(86) PCT No.: PCT/CN2016/102946
§ 371 (c)(1),
(2) Date: Apr. 27, 2018

(87) PCT Pub. No.: WO2017/071536
PCT Pub. Date: May 4, 2017

(65) Prior Publication Data
US 2018/0318254 A1    Nov. 8, 2018

(30) Foreign Application Priority Data
Oct. 28, 2015  (CN) .......................... 2015 1 0713865

(51) Int. Cl.
| | |
|---|---|
| *A61K 31/403* | (2006.01) |
| *C07D 209/52* | (2006.01) |
| *C07D 401/14* | (2006.01) |
| *C07D 401/06* | (2006.01) |
| *C07D 403/06* | (2006.01) |
| *C07D 417/06* | (2006.01) |
| *C07D 417/14* | (2006.01) |
| *C07D 471/04* | (2006.01) |
| *A61P 25/28* | (2006.01) |
| *A61K 31/4025* | (2006.01) |
| *A61K 31/4184* | (2006.01) |
| *A61K 31/437* | (2006.01) |
| *A61K 31/4439* | (2006.01) |
| *A61K 31/497* | (2006.01) |
| *A61K 31/501* | (2006.01) |
| *A61K 31/506* | (2006.01) |

(52) U.S. Cl.
CPC ........ *A61K 31/403* (2013.01); *A61K 31/4025* (2013.01); *A61K 31/4184* (2013.01); *A61K 31/437* (2013.01); *A61K 31/4439* (2013.01); *A61K 31/497* (2013.01); *A61K 31/501* (2013.01); *A61K 31/506* (2013.01); *A61P 25/28* (2018.01); *C07D 401/06* (2013.01); *C07D 401/14* (2013.01); *C07D 403/06* (2013.01); *C07D 417/06* (2013.01); *C07D 417/14* (2013.01); *C07D 471/04* (2013.01)

(58) Field of Classification Search
CPC ........................... A61K 31/403; C07D 209/52
USPC .......................................... 514/412; 548/452
See application file for complete search history.

(56) References Cited

U.S. PATENT DOCUMENTS

2008/0269250 A1   10/2008  Glatthar

FOREIGN PATENT DOCUMENTS

| CA | 3000794 | * | 5/2017 |
|---|---|---|---|
| WO | 2014/124560 | | 8/2014 |

OTHER PUBLICATIONS

Jordan, V. C. Nature Reviews: Drug Discovery, 2, 2003, 205.*
Hackam, et al. JAMA, 296(14), 2006, 1731-1732.*
Komeyama, et al., "Intramolecular Alkynylcyclopropanation of Olefins Catalyzed by Bi(OTf)3:Stereoselective Synthesis of 1-Alkynyl-3-azabicyclo[3.1.0]hexanes," Angewandte Chemie, International Edition, vol. 48, No. 52, Dec. 31, 2009, pp. 9875-9878.
International Preliminary Report on Patentability for PCT/CN2016/102946, dated Mar. 5, 2018.
Written Opinion and International Search Report for PCT/CN2016/102946, dated Jan. 4, 2018 and Jan. 11, 2018.

* cited by examiner

*Primary Examiner* — Douglas M Willis
(74) *Attorney, Agent, or Firm* — McDonnell Boehnen Hulbert & Berghoff LLP

(57) ABSTRACT

Provided herein are compounds of the formula (I), as well as pharmaceutically acceptable salts thereof, wherein the substituents are as those disclosed in the specification. These compounds, and the pharmaceutical compositions containing them, are useful for the treatment or prevention of mGluR5 mediated disorders, such as acute and/or chronic neurological disorders, cognitive disorders and memory deficits, as well as acute and chronic pain.

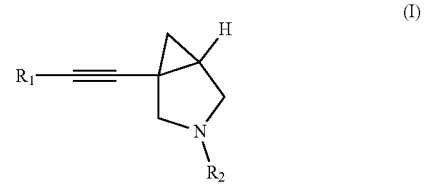

24 Claims, No Drawings

SUBSTITUTED PYRROLIDINES AS MGLUR5 ANTAGONISTS

CROSS-REFERENCE TO RELATED APPLICATIONS

This application is a national stage application under 35 U.S.C. § 371 of International Application No. PCT/CN2016/102946, filed Oct. 21, 2016, which claims priority to the Chinese Patent Application No. 201510713865.7, filed on Oct. 28, 2015, the disclosures of which are explicitly incorporated by reference herein.

BACKGROUND OF THE INVENTION

Field of the Invention

The invention is directed to mGluR5 antagonists useful for the treatment or prevention of mGluR5 mediated disorders, such as acute and/or chronic neurological disorders, cognitive disorders and memory deficits, as well as acute and chronic pain.

Description of Related Art

Glutamate is the most prominent neurotransmitter in the body, being present in over 50% of nervous tissue. Glutamate mediates its effects through two major groups of receptors: ionotropic and metabotropic. Ionotropic glutamate receptors are ion channel receptors which are often responsible for fast excitatory transmission. They are generally divided into N-methyl-D-aspartate (NMDA), α-amino-3-hydroxy-5-methyl-4-isoxazole propionic acid (AMPA) and kainite receptors. By contrast, metabotropic glutamate receptors (mGluRs) belong to the class C G-protein-coupled receptor (GPCR) protein family and are mainly involved in the modulation of fast excitatory transmission. As such, they are attractive therapeutic targets for treatment of disorders involving malfunction of glutamate signaling. The mGluRs are further divided into three groups (Group I, II and III) based on amino acid sequence homology, signal transduction mechanism and pharmacological properties. Group I receptors include mGluR1 and mGluR5, Group II includes mGluR2 and mGluR3 and Group III includes mGluR4, mGluR6, mGluR7 and mGluR8. The Group I mGluR1 and mGluR5 couple to G-proteins of the Gq family, Gq and G11, and their activation leads to activation of phospholipase C, resulting in the hydrolysis of membrane phosphatidylinositol (4, 5)-bisphosphate to diacylglycerol, which subsequently activates protein kinase C, and inositol trisphosphate, which in turn activates the inositol trisphosphate receptor to promote the release of intracellular calcium.

Anatomical studies demonstrate a broad and selective distribution of mGluRs in the mammalian nervous system. For example, mGluR5 are abundantly expressed in the striatum, cortex, hippocampus, caudate-putamen and nucleus accumbens; see for example: Shigemoto, R., Nomura, S., Hidemitsu, S., et al. *Neuroscience Lett.* 1993, 163, 53-57. As these brain areas have been shown to be involved in emotion, motivational processes, learning and memory, as well as motor control, mGluR5 modulators have long been regarded as possessing therapeutic potential for a wide range of indications.

mGluR5 antagonists can be used for modulating the activity of the mGluR5 and for use in the treatment or prevention of mGluR5 mediated disorders, such as acute and/or chronic neurological disorders, cognitive disorders and memory deficits, acute and chronic pain, protection against drug or disease induced liver damage or failure, urinary inconsistence. Other diseases contemplated include cerebral ischemia, chronic neurodegeneration including Huntington's chorea, amyotrophic lateral sclerosis, Alzheimer's disease, Parkinson's disease, psychiatric disorders, schizophrenia, mood disorders, emotion disorders, disorders of extrapyramidal motor function, obesity, disorders of pulmonary system and respiration, motor control and function, attention deficit disorders, concentration disorders, mental retardation (including mental retardation related to Fragile X syndrome), autism spectrum disorders (ASDs), pain disorders, neurodegenerative disorders, epilepsy, convulsive disorders, migraine, dyskinesia, eating disorders, vomiting, muscle spasms, urinary inconsistence, sleep disorders, sexual disorders, circadian disorders, drug withdrawal, drug addiction, compulsive disorders, anxiety, panic disorders, depressive disorders, skin disorders, retinal ischemia, retinal degeneration, glaucoma, disorders associated with organ transplantation, asthma, ischemia and astrocytomas, diseases of the cardiovascular system, diseases of the gastrointestinal system such as gastroesophageal reflux disease and irritable bowel syndrome, diseases of the endocrine system, diseases of the exocrine system, diseases of the skin, cancer and diseases of the ophthalmic system. The development and use of mGluR5 antagonists has been summarized in numerous review articles for example: Gasparini, F., Bilbe, G., Gomez-Mancilla, G., and Spooren, W., *Current Opinion in Drug Discovery & Developmen,* 655-665, 2008, 11(5); Rocher, J.-P., Bonnet, B., Bolea, C., et al., *Current Topics in Medicinal Chemistry.* 2011, 11, 680-695; Dekundy, A., Gravius, A., Hechenberger, M, et al., *J. Neural Transm.* 2011, 118, 1703-1716; Niswender, C. M.; Conn, P. *J., Annu Rev Pharmacol Toxicol,* 2010, 50, 295-322; Emmitte K A. mGluR5 negative allosteric modulators: a patent review (2010-2012). Guiying Li, Morten Jørgensen, *Expert Opin Ther Pat.* 2013, Apr. 23(4), 393-408; and Brian M Campbell. Metabotropic glutamate receptor 5-negative allosteric modulators for the treatment of psychiatric and neurological disorders (2009-July 2013), Pharmaceutical Patent Analyst. 2(6): 767-802.

SUMMARY OF THE INVENTION

The present invention is directed to compounds of the formula (I),

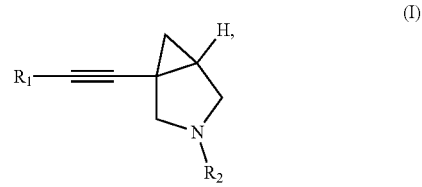

or a pharmaceutically acceptable salt thereof, to pharmaceutical compositions containing said compounds or a pharmaceutically acceptable salt thereof, wherein the definitions of $R_1$, $R_2$, are as defined below, and to methods of treating diseases and disorders. The compounds and compositions disclosed herein are mGluR5 antagonists useful for the treatment of mGluR5 mediated disorders, including acute and/or chronic neurological disorders, cognitive disorders and memory deficits, as well as acute and chronic pain.

All documents cited or relied upon below are expressly incorporated herein by reference.

DETAILED DESCRIPTION OF THE INVENTION

In an embodiment of the present invention, provided are compounds of formula (I):

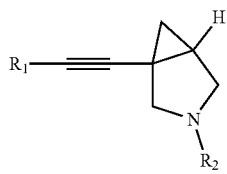

or a pharmaceutically acceptable salt thereof,
wherein:

$R_1$ is a 5- to 10-membered mono- or bicyclic heteroaryl ring that contains 1-3 heteroatoms selected from the group consisting of N, O and S, wherein the 5- to 10-membered ring system is optionally substituted with 0-3 substituents independently selected from alkyl, halogen, —OH, —CN, nitro, —CF$_3$, —O—CF$_3$, —O-alkyl, —O-aryl, —S-alkyl, —S-aryl, —S(O)-alkyl, —S(O)-aryl, —S(O$_2$)-alkyl, —S(O$_2$)-aryl, —CH$_2$-aryl, aryl, heteroaryl, —O—CH$_2$-aryl, —N(CH$_3$)$_2$, cycloalkyl, heterocycloalkyl, —C(O)-alkyl, —C(O)cycloalkyl, —C(O)heterocycloalkyl, —C(O)-aryl, —C(O)-heteroaryl, —C(O)O-alkyl, —C(O)O-cycloalkyl, —C(O)O-heterocycloalkyl, —C(O)O-aryl, —C(O)O-heteroaryl, —C(O)N-alkyl, —C(O)N-cycloalkyl, —C(O)N-heteroalkyl, —C(O)N-aryl, —C(O)N-heteroaryl or substituted lower alkyl, wherein the substituents may combine to form an optionally substituted 5-7 membered fused and optionally substituted carbocyclic or heterocyclic ring; or a 5- to 10-membered mono- or bicyclic aryl ring, wherein the 5- to 10-membered aryl ring is optionally substituted with 0-3 substituents independently selected from alkyl, halogen, —OH, —CN, nitro, —CF$_3$, —OCF$_3$, —O-alkyl, —O-aryl, —S-alkyl, —S-aryl, —S(O)-alkyl, —S(O)-aryl, —S(O$_2$)-alkyl, —S(O$_2$)-aryl, —CH$_2$-aryl, aryl, heteroaryl, —O—CH$_2$-aryl, —N(CH$_3$)$_2$, cycloalkyl, heterocycloalkyl, —C(O)-alkyl, —C(O)cycloalkyl, —C(O)-heterocycloalkyl, —C(O)-aryl, —C(O)-heteroaryl, —C(O)O-alkyl, —C(O)O-cycloalkyl, —C(O)O-heterocycloalkyl, —C(O)O-aryl, —C(O)O-heteroaryl, —C(O)N-alkyl, —C(O)N-cycloalkyl, —C(O)N-heteroalkyl, —C(O)N-aryl, —C(O)N-heteroaryl or substituted lower alkyl, wherein the substituents may combine to form a 5-7 membered fused and optionally substituted carbocyclic or heterocyclic ring.

$R_2$ is alkanoyl, arylalkanoyl, heteroaryl acyl, aryl sulfonyl, heteroaryl sulfonyl, alkoxycarbonyl, —C(O)O-aryl, arylalkoxycarbonyl, or acylamino, wherein the aryl or heteroaryl are optionally substituted with 0-3 substituents independently selected from alkyl, halogen, —OH, —CN, nitro, —CF$_3$, —OCF$_3$, —O-alkyl, —O-aryl, —S-alkyl, —S-aryl, —S(O)— alkyl, S(O)-aryl, —S(O$_2$)-alkyl, —S(O$_2$)aryl, —CH$_2$-aryl, heteroaryl, —O—CH$_2$-aryl, —N(CH$_3$)$_2$, cycloalkyl, heterocycloalkyl, —C(O)-alkyl, —C(O)cycloalkyl, —C(O)-heterocycloalkyl, —C(O)-aryl, —C(O)-heteroaryl, —C(O)O-alkyl, —C(O)O-cycloalkyl, —C(O)O-heterocycloalkyl, —C(O)O-aryl, —C(O)O-heteroaryl, —C(O)N-alkyl, —C(O)N-cycloalkyl, —C(O)N-heteroalkyl, —C(O)N-aryl, —C(O)N-heteroaryl or substituted lower alkyl, wherein the substituents may combine to form an optionally substituted 5-7 membered fused carbocyclic or heterocyclic ring; or a 5- to 10-membered mono- or bicyclic heteroaryl ring that contains 1-3 heteroatoms selected from the group consisting of N, O and S, wherein the 5- to 10-membered ring system is optionally substituted with 0-3 substituents independently selected from alkyl, halogen, —OH, —CN, nitro, —CF$_3$, —O—CF$_3$, —O-alkyl, —O-aryl, —S-alkyl, —S-aryl, —S(O)-alkyl, —S(O)-aryl, —S(O$_2$)-alkyl, —S(O$_2$)-aryl, —CH$_2$-aryl, aryl, heteroaryl, —O—CH$_2$-aryl, —N(CH$_3$)$_2$, cycloalkyl, heterocycloalkyl, —C(O)-alkyl, —C(O)cycloalkyl, —C(O)heterocycloalkyl, —C(O)-aryl, —C(O)-heteroaryl, —C(O)O-alkyl, —C(O)O-cycloalkyl, —C(O)O-heterocycloalkyl, —C(O)O-aryl, —C(O)O-heteroaryl, —C(O)N-alkyl, —C(O)N-cycloalkyl, —C(O)N-heteroalkyl, —C(O)N-aryl, —C(O)N-heteroaryl or substituted lower alkyl, wherein the substituents may combine to form an optionally substituted 5-7 membered fused and optionally substituted carbocyclic or heterocyclic ring; or a 5- to 10-membered mono- or bicyclic aryl ring, wherein the 5- to 10-membered ring system is optionally substituted with 0-3 substituents independently selected from alkyl, halogen, —OH, —CN, nitro, —CF$_3$, —OCF$_3$, —O-alkyl, —O-aryl, —S-alkyl, —S-aryl, —S(O)-alkyl, S(O)-aryl, —S(O$_2$)-alkyl, —S(O$_2$)aryl, —CH$_2$-aryl, aryl, heteroaryl, —O—CH$_2$-aryl, —N(CH$_3$)$_2$, cycloalkyl, heterocycloalkyl, —C(O)-alkyl, —C(O)cycloalkyl, —C(O)-heterocycloalkyl, —C(O)-aryl, —C(O)-heteroaryl, —C(O)O-alkyl, —C(O)O-cycloalkyl, —C(O)O-heterocycloalkyl, —C(O)O-aryl, —C(O)O-heteroaryl, —C(O)N-alkyl, —C(O)N-cycloalkyl, —C(O)N-heteroalkyl, —C(O)N-aryl, —C(O)N-heteroaryl or substituted lower alkyl, wherein the substituents may combine to form an optionally substituted 5-7 membered fused carbocyclic or heterocyclic ring.

In a further embodiment of the present invention, provided is a compound according to formula (I), or a pharmaceutically acceptable salt thereof, wherein:

$R_1$ is a substituted or unsubstituted ring selected from the following list:

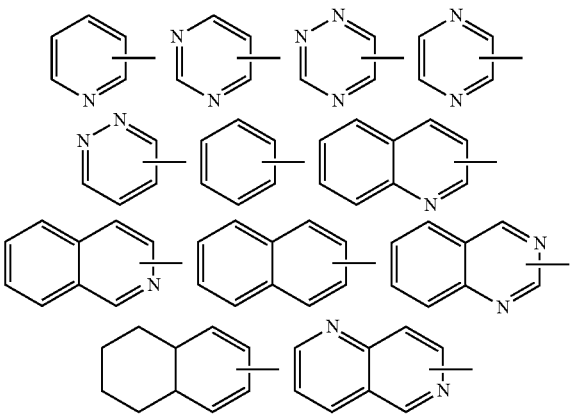

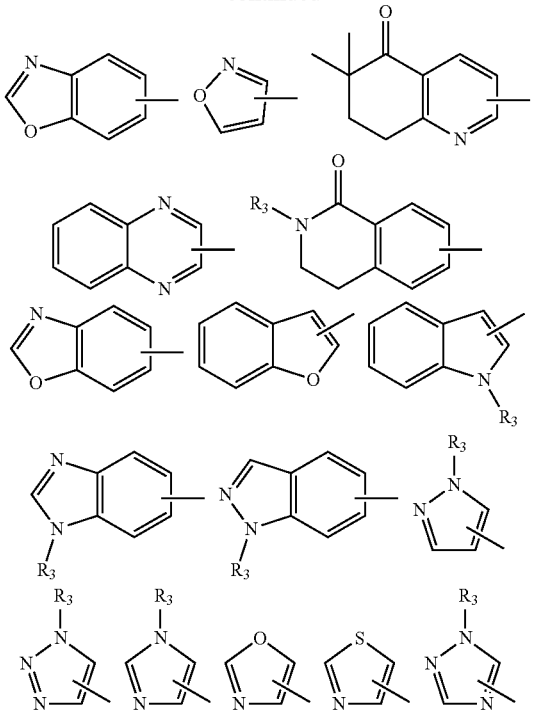

wherein the ring is optionally substituted with 0-3 substituents independently selected from alkyl, halogen, —OH, —CN, nitro, —CF$_3$, —OCF$_3$, —O-alkyl, —O-aryl, —S-alkyl, —S-aryl, —S(O)-alkyl, S(O)-aryl, —S(O$_2$)-alkyl, —S(O$_2$)aryl, —CH$_2$-aryl, aryl, heteroaryl, —O—CH$_2$-aryl, —N(CH$_3$)$_2$, cycloalkyl, heterocycloalkyl, —C(O)-alkyl, —C(O)cycloalkyl, —C(O)— heterocycloalkyl, —C(O)-aryl, —C(O)-heteroaryl, —C(O)O-alkyl, —C(O)O-cycloalkyl, —C(O)O-heterocycloalkyl, —C(O)O-aryl, —C(O)O-heteroaryl, —C(O)N-alkyl, —C(O)N— cycloalkyl, —C(O)N-heteroalkyl, —C(O)N-aryl, —C(O)N-heteroaryl or substituted lower alkyl, wherein the substituents may combine to form an optionally substituted 5-7 membered fused carbocyclic or heterocyclic ring;

R$_3$ is —H or lower alkyl;

R$_2$ is alkanoyl, arylalkanoyl, heteroaryl acyl, aryl sulfonyl, heteroaryl sulfonyl, alkoxycarbonyl, —C(O)O-aryl, arylalkoxycarbonyl, or acylamino, wherein the aryl or heteroaryl are optionally substituted with 0-3 substituents independently selected from alkyl, halogen, —OH, —CN, nitro, —CF$_3$, —OCF$_3$, —O-alkyl, —O-aryl, —S-alkyl, —S-aryl, —S(O)— alkyl, S(O)-aryl, —S(O$_2$)-alkyl, —S(O$_2$)aryl, —CH$_2$-aryl, heteroaryl, —O—CH$_2$-aryl, —N(CH$_3$)$_2$, cycloalkyl, heterocycloalkyl, —C(O)-alkyl, —C(O)cycloalkyl, —C(O)-heterocycloalkyl, —C(O)-aryl, —C(O)-heteroaryl, —C(O)O-alkyl, —C(O)O-cycloalkyl, —C(O)O-heterocycloalkyl, —C(O)O-aryl, —C(O)O-heteroaryl, —C(O)N-alkyl, —C(O)N-cycloalkyl, —C(O)N-heteroalkyl, —C(O)N-aryl, —C(O)N-heteroaryl or substituted lower alkyl, wherein the substituents may combine to form an optionally substituted 5-7 membered fused carbocyclic or heterocyclic ring; or a 5- to 10-membered mono- or bicyclic heteroaryl ring that contains 1-3 heteroatoms selected from the group consisting of N, O and S, wherein the 5- to 10-membered ring system is optionally substituted with 0-3 substituents independently selected from alkyl, halogen, —OH, —CN, nitro, —CF$_3$, —O—CF$_3$, —O-alkyl, —O-aryl, —S-alkyl, —S-aryl, —S(O)-alkyl, —S(O)-aryl, —S(O$_2$)-alkyl, —S(O$_2$)-aryl, —CH$_2$-aryl, aryl, heteroaryl, —O—CH$_2$-aryl, —N(CH$_3$)$_2$, cycloalkyl, heterocycloalkyl, —C(O)-alkyl, —C(O)cycloalkyl, —C(O)heterocycloalkyl, —C(O)-aryl, —C(O)-heteroaryl, —C(O)O-alkyl, —C(O)O-cycloalkyl, —C(O)O-heterocycloalkyl, —C(O)O-aryl, —C(O)O-heteroaryl, —C(O)N-alkyl, —C(O)N-cycloalkyl, —C(O)N-heteroalkyl, —C(O)N-aryl, —C(O)N-heteroaryl or substituted lower alkyl, wherein the substituents may combine to form an optionally substituted 5-7 membered fused and optionally substituted carbocyclic or heterocyclic ring; or a 5- to 10-membered mono- or bicyclic aryl ring, wherein the 5- to 10-membered ring system is optionally substituted with 0-3 substituents independently selected from alkyl, halogen, —OH, —CN, nitro, —CF$_3$, —OCF$_3$, —O-alkyl, —O-aryl, —S-alkyl, —S-aryl, —S(O)-alkyl, S(O)-aryl, —S(O$_2$)-alkyl, —S(O$_2$)aryl, —CH$_2$-aryl, aryl, heteroaryl, —O—CH$_2$-aryl, —N(CH$_3$)$_2$, cycloalkyl, heterocycloalkyl, —C(O)-alkyl, —C(O)cycloalkyl, —C(O)-heterocycloalkyl, —C(O)-aryl, —C(O)-heteroaryl, —C(O)O-alkyl, —C(O)O-cycloalkyl, —C(O)O-heterocycloalkyl, —C(O)O-aryl, —C(O)O-heteroaryl, —C(O)N-alkyl, —C(O)N-cycloalkyl, —C(O)N-heteroalkyl, —C(O)N-aryl, —C(O)N-heteroaryl or substituted lower alkyl, wherein the substituents may combine to form an optionally substituted 5-7 membered fused carbocyclic or heterocyclic ring.

In a further embodiment of the present invention, provided is a compound according to formula (I), or a pharmaceutically acceptable salt thereof, wherein:

R$_1$ is an optionally mono- or disubstituted 5- to 6-membered monocyclic heteroaryl ring that contains 1-3 heteroatoms selected from the group consisting of N, O and S; and R$_2$ is optionally mono- or disubstituted 5- to 10-membered mono- or bicyclic aryl, or optionally mono- or disubstituted mono- or bicyclic heteroaryl that contains 1-3 heteroatoms selected from the group consisting of N, O and S, or optionally substituted —C(O)—C$_1$-C$_5$-alkyl, —C(O)—C$_1$-C$_5$-alkyl-aryl, —C(O)-aryl, —C(O)-heteroaryl, —C(O)O—C$_1$-C$_5$-alkyl, —C(O)O—C$_1$-C$_5$-alkyl-aryl or —S(O$_2$)-phenyl.

In a further embodiment of the present invention, provided is a compound according to formula (I), or a pharmaceutically acceptable salt thereof, wherein:

R$_1$ is 2-pyridinyl or substituted 2-pyridinyl, 4-pyridinyl or substituted 4-pyridinyl, or R$_1$ is pyrimidinyl, pyrazinyl, pyridazinyl or thiazoly.

In a further embodiment of the present invention, provided is a compound according to formula (I), or a pharmaceutically acceptable salt thereof, wherein:

R$_1$ is 2-pyridinyl optionally substituted with 1 or 2 substituents independently selected from halogen, —C$_1$-C$_4$-alkyl, —O—C$_1$-C$_4$-alkyl, wherein halogen includes —F, —Cl, —Br or —I; —C$_1$-C$_4$-alkyl includes, but are not limited to, methyl, ethyl, propyl, iso-propyl, butyl, iso-butyl, tert-butyl; —O—C$_1$-C$_4$-alkyl includes, but are not limited to methoxyl, ethyoxyl, propoxyl, iso-propoxyl, butoxyl, iso-butoxyl or tert-butoxyl, or R$_1$ is 4-pyridinyl optionally substituted with 1 or 2 substituents independently selected from halogen, —C$_1$-C$_4$-alkyl, —O—C$_1$-C$_4$-alkyl, wherein halogen includes —F, —Cl, —Br or —I; —C$_1$-C$_4$-alkyl includes, but are not limited to, methyl, ethyl, propyl, iso-propyl, butyl, iso-butyl, tert-butyl, —O—$C_1$-$C_4$-alkyl includes, but are not limited to methoxyl, ethyoxyl, propoxyl, iso-propoxyl, butoxyl, iso-butoxyl or tert-butoxyl; or $R_1$ is pyrimidinyl, pyrazinyl, pyridazinyl or thiazoly optionally substituted with 1 or 2 substituents independently selected from halogen, —$C_1$-$C_4$-alkyl, —O—$C_1$-$C_4$-alkyl, wherein halogen includes —F, —Cl, —Br or —I; —$C_1$-$C_4$-alkyl includes, but are not limited to, methyl, ethyl, propyl, iso-propyl, butyl, iso-butyl, tert-butyl; the —O—$C_1$-$C_4$-alkyl includes, but are not limited to methoxyl, ethyoxyl, propoxyl, iso-propoxyl, butoxyl, iso-butoxyl or tert-butoxyl.

$R_2$ is a 5- to 10-membered mono- or bicyclic aryl or heteroaryl ring that contains 1, 2, or 3 heteroatoms independently selected from the group consisting of N, O and S, wherein the 5- to 10-membered ring system is optionally substituted with 1 or 2 substituents independently selected from —$C_1$-$C_4$-alkyl, halogen, —CN, nitro, —$CF_3$, —$OCF_3$, —O—$C_1$-$C_4$-alkyl, —$SCH_3$, —S(O)—$CH_3$, —S($O_2$)—$CH_3$, —$CO_2CH_3$, —C(O)$NH_2$, —C(O)NH($CH_3$), —C(O)N($CH_3$)$_2$, phenyl, wherein halogen includes —F, —Cl, —Br or —I; the —$C_1$-$C_4$-alkyl includes, but are not limited to methyl, ethyl, propyl, iso-propyl, butyl, iso-butyl, tert-butyl; the —O—$C_1$-$C_4$-alkyl includes, but are not limited to methoxyl, ethoxyl, propoxyl, iso-proxyl, butoxyl, iso-butoxyl, tert-butoxyl, wherein the 5- to 10-membered ring system is preferably phenyl, pyridinyl, benzimidazolyl, azaindolyl; or $R_2$ is —C(O)—$C_1$-$C_5$-alkyl, —C(O)—$C_1$-$C_5$-alkyl-aryl, —C(O)-phenyl, —C(O)-benzyl, —CO-pyridinyl, —C(O)O—$C_1$-$C_5$-alkyl, —C(O)O—$C_1$-$C_5$-alkyl-phenyl, —C(O)O-phenyl, —C(O)O-benzyl —S($O_2$)-phenyl, —C(O)N-aryl, —C(O)N-alkyl, —C(O)N-alkyl-$CF_3$, wherein —$C_1$-$C_5$-alkyl includes methyl, ethyl, propyl, iso-propyl, butyl, iso-butyl, tert-butyl, pentyl, iso-pentyl, tert-pentyl, neo-pentyl. The benzyl or phenyl in the substitutions is optionally further substituted with 1 or 2 substituents selected from halogen, —$C_1$-$C_4$-alkyl, —CN or —O—$CF_3$ which is optionally further substituted with a 1 or 2 substituents independent selected from halogen, —$C_1$-$C_4$-alkyl, —CN or —O—$CF_3$ wherein halogen includes —F, —Cl, —Br or —I; —$C_1$-$C_4$-alkyl includes, but are not limited to, methyl, ethyl, propyl, iso-propyl, butyl, iso-butyl, tert-butyl.

In a still further embodiment of the present invention, provided is a pharmaceutical composition, comprising a therapeutically effective amount of a compound according to formula (I) or a pharmaceutically acceptable salt thereof and a pharmaceutically acceptable carrier.

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are now described.

As used herein, the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

As used herein, the term "alkenyl", alone or in combination with other groups, refers to a straight-chain or branched hydrocarbon residue having an olefinic bond of two to twenty carbon atoms, preferably two to sixteen carbon atoms, more preferably two to ten carbon atoms.

The term "cycloalkyl" refers to a monovalent mono- or polycarbocyclic radical of three to ten, preferably three to six carbon atoms. This term is further exemplified by radicals such as cyclopropyl, cyclobutyl, cyclopentyl, cyclohexyl, cycloheptyl, norbornyl, adamantyl, indanyl and the like. In a preferred embodiment, the "cycloalkyl" moieties can optionally be substituted with one, two, three or four substituents, with the understanding that said substituents are not, in turn, substituted further unless indicated otherwise in the Examples or claims below.

Each substituent can independently be, alkyl, alkoxy, halogen, amino, hydroxyl or oxygen (O=) unless otherwise specifically indicated. Examples of cycloalkyl moieties include, but are not limited to, optionally substituted cyclopropyl, optionally substituted cyclobutyl, optionally substituted cyclopentyl, optionally substituted cyclopentenyl, optionally substituted cyclohexyl, optionally substituted cyclohexylene, optionally substituted cycloheptyl, and the like or those which are specifically exemplified herein.

The term "heterocycloalkyl" denotes a mono- or polycyclic alkyl ring, wherein one, two or three of the carbon ring atoms is replaced by a heteroatom such as N, O or S. Examples of heterocycloalkyl groups include, but are not limited to, morpholinyl, thiomorpholinyl, piperazinyl, piperidinyl, pyrrolidinyl, tetrahydropyranyl, tetrahydrofuranyl, 1,3-dioxanyl and the like. The heterocycloalkyl groups may be unsubstituted or substituted and attachment may be through their carbon frame or through their heteroatom(s) where appropriate, with the understanding that said substituents are not, in turn, substituted further unless indicated otherwise in the Examples or claims below.

The term "lower alkyl", alone or in combination with other groups, refers to a branched or straight-chain alkyl radical of one to nine carbon atoms, preferably one to six carbon atoms, more preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

The term "aryl" refers to an aromatic mono- or polycarbocyclic radical of 6 to 12 carbon atoms having at least one aromatic ring. Examples of such groups include, but are not limited to, phenyl, naphthyl, 1, 2, 3, 4-tetrahydronaphthalene, 1, 2-dihydronaphthalene, indanyl, 1H-indenyl and the like.

The alkyl, lower alkyl and aryl groups may be substituted or unsubstituted. When substituted, there will generally be, for example, 1 to 4 substituents present, with the understanding that said substituents are not, in turn, substituted further unless indicated otherwise in the Examples or claims below. These substituents may optionally form a ring with the alkyl, lower alkyl or aryl group with which they are connected. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl (hydroxyl)alkyl), ethers (e.g. alkoxy, aryloxy, alkoxyalkyl, aryloxyalkyl, more preferably, for example, methoxy and ethoxy), aldehydes (e.g. carboxaldehyde), ketones (e.g. alkylcarbonyl, alkylcarbonylalkyl, arylcarbonyl, arylalkylcarbonyl, arycarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g.

alkoxycarbonylamino, aryloxycarbonylamino, aminocarbonyloxy, mono- or di-alkylaminocarbonyloxy, arylminocarbonloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more heteroatoms, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl, benzothiazoyl and carbolinyl).

The term "heteroaryl," refers to an aromatic mono- or polycyclic radical of 5 to 12 atoms having at least one aromatic ring containing one, two, or three ring heteroatoms selected from N, O, and S, with the remaining ring atoms being C. One or two ring carbon atoms of the heteroaryl group may be replaced with a carbonyl group. Examples of such groups include, but are not limited to, pyrimidinyl, pyridyl, indoyl, quinolinyl, pyridon-2-yl, isoquinolinyl, 5,6,7,8-tetrahydroquinolinyl, thienyl, furanyl, imidazolyl, pyrazolyl, thiazolyl, isothiazolyl, oxazolyl, oxadiazolyl, thiadiazolyl, pyrazolidinyl, pyrazinyl, pyridazinyl, thianaphthyl, benzofuranyl, isobenzofuranyl, oxyindolyl, isoindolyl, indazolyl, indolinyl, 7-azaindolyl, benzopyranyl, coumarinyl, isocoumarinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and the like.

The heteroaryl group described above may be substituted independently with one, two, or three substituents, with the understanding that said substituents are not, in turn, substituted further unless indicated otherwise in the Examples or claims below. These substituents may optionally form a ring with the heteroaryl group to which they are connected. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl), aldehydes (e.g. carboxaldehyde), ketones (e.g. alkylcarbonyl, alkylcarbonylalkyl, arylcarbonyl, arylalkylcarbonyl, arylcarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, aryloxycarbonylamino, aminocarbonyloxy, mono- or di-alkylaminocarbonyloxy, arylminocarbonloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more heteroatoms, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl, benzothiazoyl and carbolinyl).

As used herein, the term "alkoxy" means alkyl-O—; and "alkanoyl" means alkyl-CO—. Alkoxy substituent groups or alkoxy-containing substituent groups may be substituted by, for example, one or more alkyl groups, with the understanding that said substituents are not, in turn, substituted further unless indicated otherwise in the Examples or claims below.

As used herein, the term "halogen" means a fluorine, chlorine, bromine or iodine radical, preferably a fluorine, chlorine or bromine radical, and more preferably a fluorine or chlorine radical.

Compounds of formula (I) can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). The invention embraces all of these forms.

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include, for example, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, sulfuric and methanesulfonic acids. Acceptable base salts include alkali metal (e.g. sodium, potassium), alkaline earth metal (e.g. calcium, magnesium) and aluminum salts.

In the practice of the method of the present invention, an effective amount of any one of the compounds of this invention or a combination of any of the compounds of this invention or a pharmaceutically acceptable salt thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases. Thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions or of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as a "therapeutically effective amount". For example, the dose of a compound of the present invention is typically in the range of about 1 mg to about 1000 mg per day. Preferably, the therapeutically effective amount is in an amount of from about 1 mg to about 500 mg per day.

It will be appreciated, that the compounds of general formula (I) in this invention may be derivatized at functional groups to provide derivatives which are capable of conversion back to the parent compound in vivo. Physiologically acceptable and metabolically labile derivatives, which are capable of producing the parent compounds of general formula (I) in vivo are also within the scope of this invention.

Compounds of the present invention can be prepared beginning with commercially available starting materials and utilizing general synthetic techniques and procedures known to those skilled in the art. Chemicals may be purchased from companies such as for example Aldrich, Argonaut Technologies, VWR and Lancaster.

The compounds of formula (I) can be prepared by the following General Reaction Scheme:

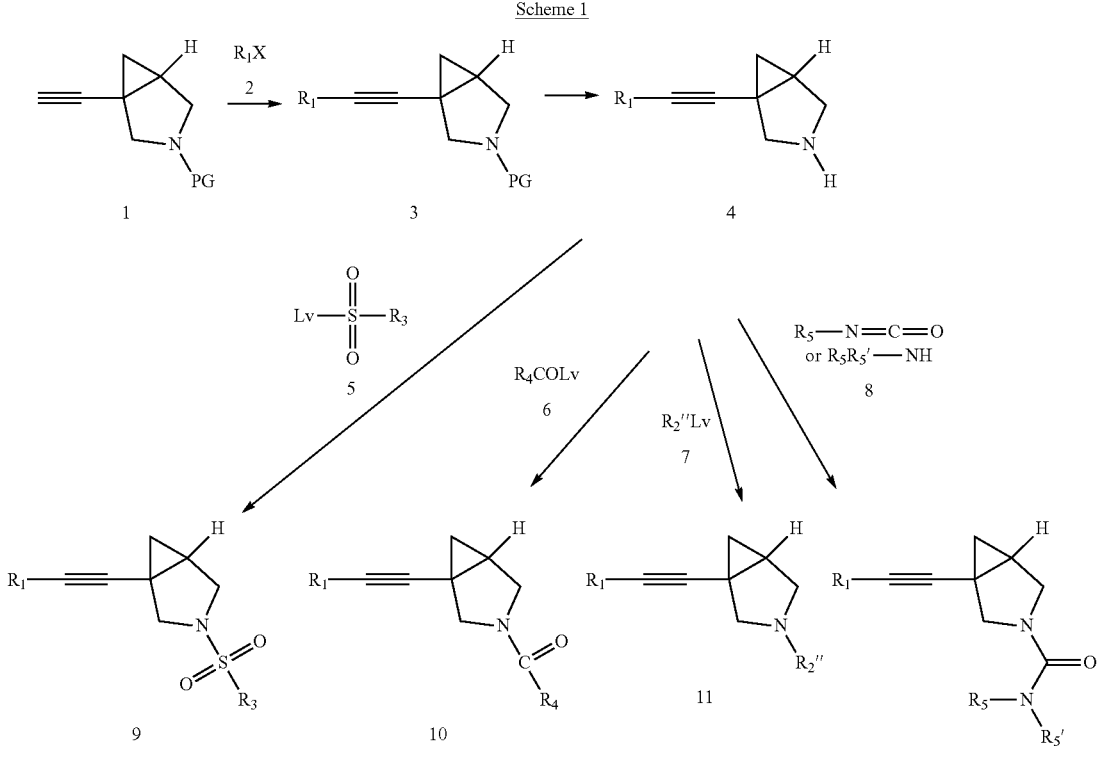

In Scheme 1 compound of formula 1, in which PG is a protecting group, for example a 1,1-dimethylethoxycarbonyl (Boc) group, is known as a common intermediate, and the preparation of compound 1 would be described in Scheme 3.

Reaction of compounds 1 and 2 to form the alkyne 3 can be achieved by Sonogashira coupling of the alkyne 1 and halohydrocarbon 2 in a suitable inert solvent, for example THF, by adding $Pd(PPH_3)_2Cl_2$, $Et_3N$ and CuI, then the reaction mixture microwaved at a medium temperature, for example 90° C., after reaction is complete and the newly formed compound 3 can be isolated using conventional techniques, for example by quenching the reaction with an aqueous solution followed by extraction of the products into an organic solvent, washing with brine, drying and chromatography over silica gel, if necessary (Sonogashira, K. (2002), "Development of Pd—Cu catalyzed cross-coupling of terminal acetylenes with $sp^2$-carbon halides", *J. Organomet. Chem.* 653: 46-49; King, A. O.; Yasuda, N. (2004), "Palladium-Catalyzed Cross-Coupling Reactions in the Synthesis of Pharmaceuticals Organometallics in Process Chemistry", Top. *Organomet. Chem.* 6: 205-245).

Conditions for the removal of the protecting group in 3 to give a compound of structure 4, will depend on the particular choice of protecting group employed. Skilled organic chemists will be familiar with the various potential protecting and the procedures for their removal. In this regard, reference to a compendium of protecting groups such as Wuts, P. G. and Greene, T. W., *Greene's Protective Groups in Organic Synthesis*, $4^{th}$ ed., cited above may be useful. In one convenient implementation, a Boc ((1,1-dimethylethoxy)carbonyl) group may be used. In this case, its removal to give a compound of structure 4 may be readily achieved by treatment with an acid, for example trifluoroacetic acid (TFA) in a suitable solvent, for example dichloromethane followed by a conventional workup.

Further transformation of compounds of structure 4 to compounds of the invention will depend on the particular target compound desired. In the case that introduction of a sulfonyl group is desired to give a compound of structure 8, a compound of structure 4 may be treated with an activated sulfonyl derivative 5 in which Lv is a leaving group, for example a chloride. Such transformations are generally carried out in the presence of an organic or inorganic base, for example trimethylamine (TEA) in a suitable solvent such as dichloromethane. Skilled organic chemists will be familiar with the general reaction scope and be able to choose appropriate conditions for the target compound of interest.

In the event that an amide or carbamate of structure 9 is desired ($R_4$=aryl, heteroaryl, alkyl, alkoxy, or arylalkoxy), a compound of structure 4 may be treated with an activated ester derivative 6 in which Lv is a suitable leaving group for acylation reactions, for example a halogen atom such as a chloride. Such reactions may be carried out under a wide variety of conditions well known to skilled organic chemists. In one set of conditions, an acyl chloride 6, in which Lv is chloride can be allowed to react with the amine 4 in an inert solvent such as dichloromethane at a suitable temperature, for example room temperature in the presence of base, for example TEA followed by a conventional workup involving quenching with an aqueous solution, extraction of the product into an organic solvent, drying, evaporation and optionally, chromatographic purification of the residue.

In case the desired compound is an N-aryl or N-heteroaryl derivative of structure 11, a compound of structure 4 may be reacted with a compound of structure 7 in which Lv represents a leaving group suitable for participation in a Buchwald reaction or Chan-Lam coupling reaction and $R_2''$ represents a $R_2$ of the invention or incorporates functionality that can transformed into a $R_2$ of the invention through manipulation of substituents and protecting groups after the coupling reaction. Typical groups include iodide, bromide and chloride. Reactions typically are run in the presence of a base, which can either be a strong base such as LiHMDS or a weaker base such as $Cs_2CO_3$ in the presence of a palladium catalyst and suitable ligand. The selection of the base, solvent and ligand for a particular desired transformation may be guided by literature precedent (Surry, D. S. and Buchwald, S. L, *Chem. Sci.* 2011, 2: 27-50; D. M. T. Chan, K. L. Monaco, R.-P. Wang, M. P. Winteres, *Tetrahedron Lett.* 1998, 39: 2933-2936). For aryl and heteroaryl moieties with highly reactive leaving groups, for example 2-fluoropyridine, a direct reaction between that compound and compound 4 in the presence of a suitable base, for example potassium carbonate at an elevated temperature, for example 90-130° C. can affect their transformation to a compound of structure 11.

In case the desired compound is the urea derivative of structure of 12 ($R_5$=aryl, heteroaryl, $C_1$-$C_4$-alkyl, trifluoromethylalkyl, $R_5'$=hydrogen, $C_1$-$C_4$-alkyl, wherein $R_5$, $R_5'$ and the nitrogen atom to which they are attached may be combined to form an azacycloalkane), compound of structure 4 may be treated with isocyanate in the presence of presence of base, for example TEA, or treated with amine in the presence of CDI, to get the desired compound of structure of 12 (Johnson Douglas S., Ahn Kay, Kesten Suzanne, et al. Bioorganic & medicinal chemistry letters 2009, 19(10):2865-2869; Satoshi Sasaki, Nobuo Cho, Yoshi Nara, et al. J. Med. Chem. 2003, 46 (1): 113-124).

Scheme 2

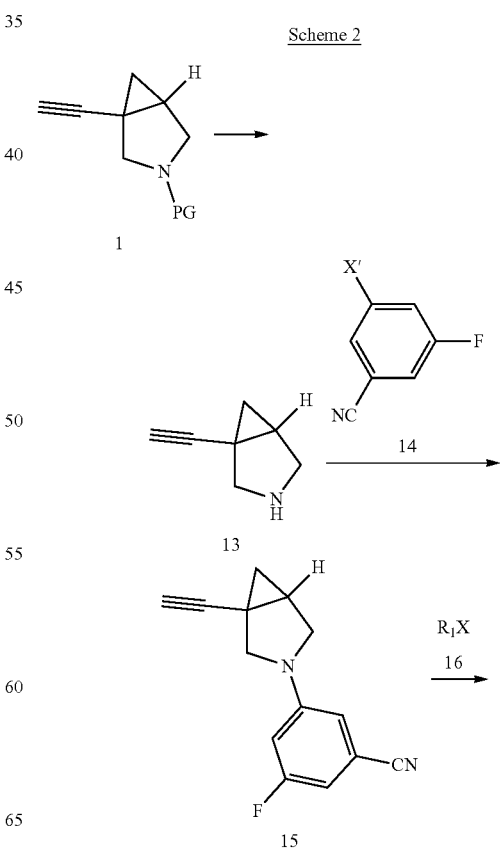

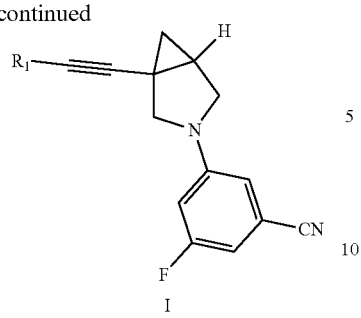

The method for preparation of compounds of formula (I) (for $R_2$=3-cyano-5-fluorophenyl) is shown in Scheme 2. Compounds 1 as described in Scheme 1 by deprotecting to give alkyne 13, may then undergo a Buchwald coupling reaction with compound 14 in which X' is halogen, like iodide, bromide and chloride to give compound 15. Compound 15 and 16 undergo a Sonogashira coupling reaction (Sonogashira, K., "Development of Pd—Cu catalyzed cross-coupling of terminal acetylenes with sp²-carbon halides", *J. Organomet. Chem.* 2002, 653: 46-49) to give the compounds of formula (I) (for $R_2$=3-cyano-5-fluorophenyl).

Scheme 3

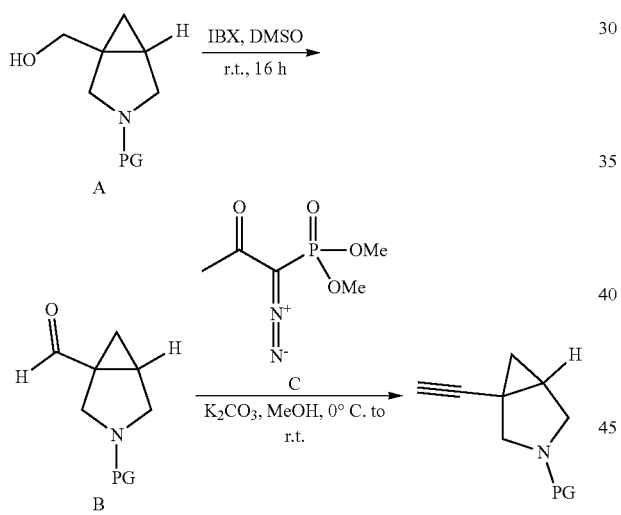

The procedure for preparation of compound 1 is shown in Scheme 3. Compound A is commercially available from Wuxi AppTech, treatmentment of A with an appropriate oxidant, like IBX in an inert solvent DMSO for example to give aldehyde B (Frigerio, M.; Santadostino, M.; Sputore, S.; Palmisano, G. *J. Org. Chem.* 1995, 60, 7272). Reacting B with Bestmann-Ohira Reagent Dimethyl (1-diazo-2-oxo-propyl)-phosphonate through Seyferth-Gilbert homologation in the presence of base like potassium carbonate in a solvent such as methanol yields the desired compounds of formular 1 (S. Müller, B. Liepold, G. J. Roth, H. J. Bestmann, Synlett, 1996, 521-522; Ohira, S. Synthetic Commun. 1989, 19: 561-564).

The invention will now be further described in the Examples below, which are intended as an illustration only and do not limit the scope of the invention.

EXAMPLES

Example 1

Preparation of tert-butyl 1-ethynyl-3-azabicyclo[3.1.0]hexane-3-carboxylate

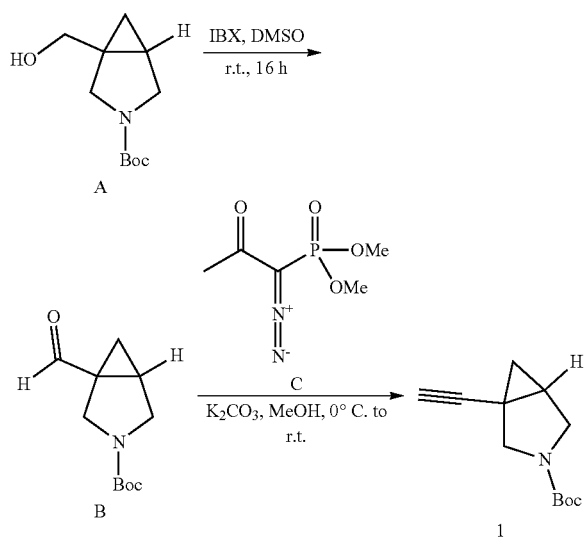

Experimental Section

Procedure for Preparation of B

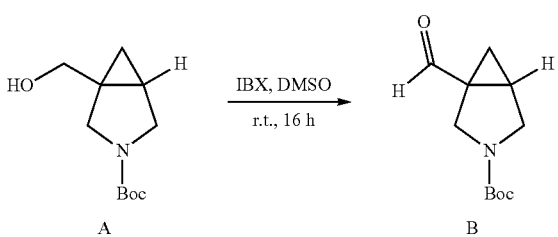

To a solution of compound A (3.50 g, 16.4 mmol) in DMSO (30 mL) was added IBX (6.89 g, 24.6 mmol). The mixture was stirred at rt. for 16 hrs. TLC indicated compound A was consumed completely. The white suspension was diluted with EA (50 mL), filtered by celite pad. The filter was washed with saturated $NaHCO_3$ (50 mL), then saturated $Na_2SO_3$ (50 mL) (KI paper test, negative), brine (50 mL), dried over anhydrous $Na_2SO_4$, filtered and concentrated. The crude product B (2.95 g, yield: 85%) was used for the next step without further purification.

Procedure for Preparation of 1

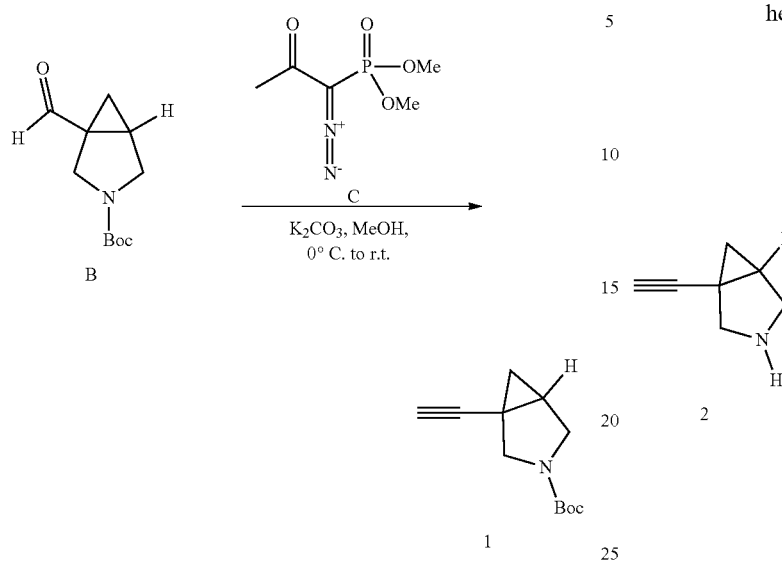

To a solution of compound B (2.95 g, 13.9 mmol) in MeOH (30 mL) was added K₂CO₃ (5.79 g, 41.8 mmol), and then C (4.83 g, 25.1 mmol) was added at 0° C. The mixture was stirred at rt. for 16 hrs. TLC indicated compound B was consumed completely and one new spot formed. The reaction mixture was diluted with DCM (50 mL) and H₂O (40 mL). The combined organic layers were washed with brine (60 mL), dried over anhydrous Na₂SO₄, filtered and concentrated under reduced pressure to give a residue. The residue was purified by column chromatography to give product 1 (2.70 g, yield: 93%).

Example 2

Procedure for Preparation of 1-ethynyl-3-azabicyclo[3.1.0]hexane

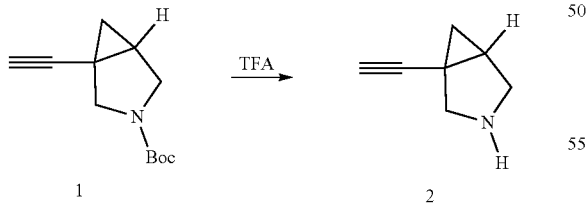

To a solution of 1 (2.0 g, 9.65 mmol) in DCM (20 mL) was added TFA (10 mL). The mixture was stirred at rt. for 1 hr., LCMS showed that 1 was consumed completely. The reaction mixture was concentrated under reduced pressure. The residue was dissolved in MeOH, then neutralized pH to 8-9 by basic resin, filtered and concentrated under reduced pressure to give the crude product 2 (1.0 g, crude), which was used for the next step without purification.

Example 3

Preparation of 3-(1-ethynyl-3-azabicyclo[3.1.0]hexan-3-yl)-5-fluorobenzonitrile

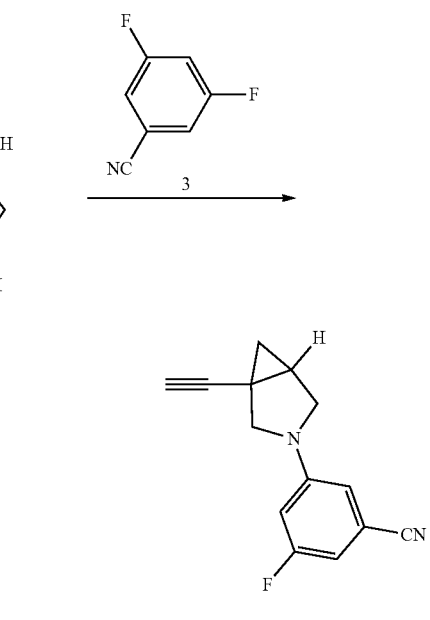

Experimental Section

Procedure for Preparation of 4

To a solution of 2 (1.0 g, 9.33 mmol) and 3 (1.5 g, 11.2 mmol) in DMF (10 mL) was added K₂CO₃ (2.5 g, 18.6 mmol). The mixture was stirred at 110° C. for 16 hrs. The reaction mixture was concentrated under reduced pressure. The residue was diluted with water (20 mL) and extracted with EA (30 mL×3), filtered and concentrated under reduced pressure to give a residue, which was purified by prep-HPLC to give product 4 (450 mg, yield: 21%).

Example 4

Preparation of 1-(pyridin-2-ylethynyl)-3-azabicyclo[3.1.0]hexane

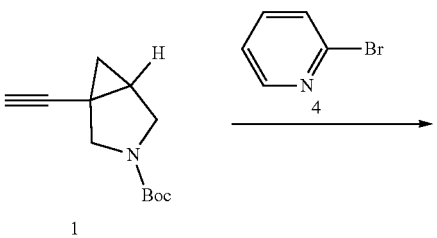

-continued

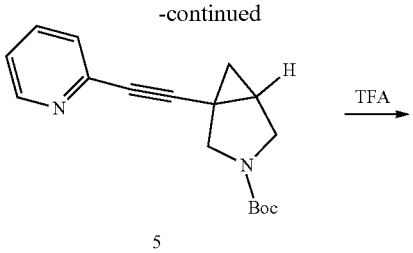

5

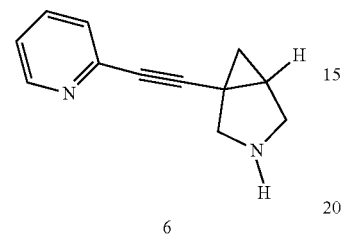

6

Experimental Section

Procedure for Preparation of 5

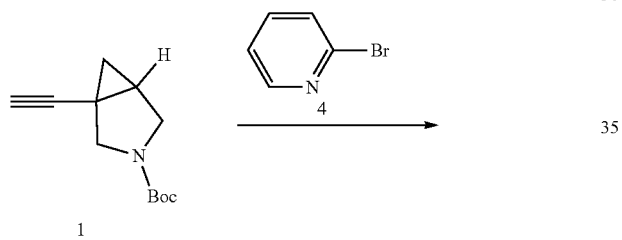

A mixture of 1 (640.00 mg, 3.09 mmol), 4 (732.33 mg, 4.64 mmol), Pd(PPh₃)₂Cl₂ (216.89 mg, 309.00 μmol), Et₃N (625.35 mg, 6.18 mmol) and CuI (58.85 mg, 309.00 μmol) were taken up into a microwave tube in THF (20 mL). The sealed tube was degassed with N₂ twice and then heated at 90° C. for 1 hr under microwave. TLC showed the starting material was consumed. After cooling to rt., EA (20 mL) and water (20 mL) were added. The aqueous layer was extracted with EA (20 mL×2). The combined organic layers were washed with brine (30 mL), dried over anhydrous Na₂SO₄, concentrated in vacuo to give the crude product, which was purified by chromatograph column to give product 5 (800.00 mg, yield: 91.05%).

LCMS: m/z, 285 (M+H)⁺.

Procedure for Preparation of 6

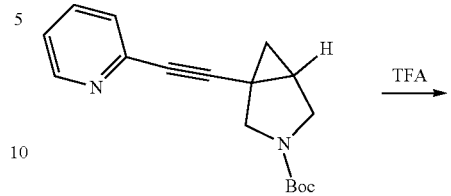

To a mixture of 5 (700.00 mg, 2.46 mmol) in DCM (20 mL) was added TFA (4 mL) in one portion at rt., the mixture was stirred at rt. for 1 hr. LCMS showed the reaction was completed. The mixture was concentrated in reduced pressure at 50° C. The residue was poured into saturated NaHCO₃ solution (50 mL) and stirred for 10 min. The aqueous phase was extracted with EA (30 mL×3). The combined organic phase was washed with saturated brine (30 mL×1), dried over anhydrous Na₂SO₄, filtered and concentrated in vacuo to afford product 6 (400.00 mg, yield: 88.26%).

Example Compound 1

Preparation of 3-fluoro-S-(1-(pyridin-2-ylethynyl)-3-azabicyclo[3.1.0]hexan-3-yl) benzonitrile

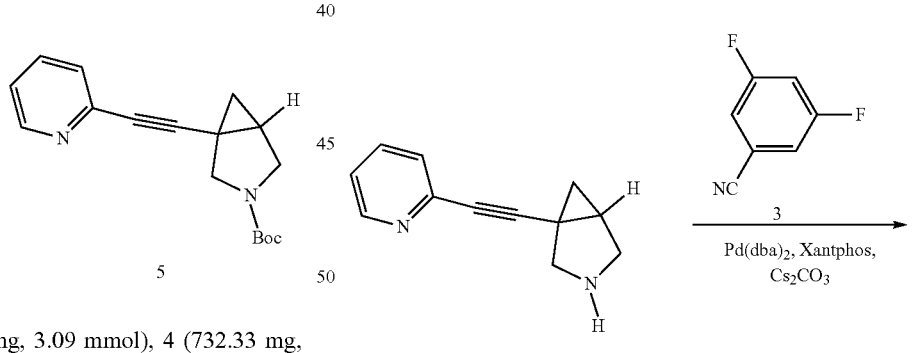

Compound 1

Experimental Section

Procedure for Preparation of Compound 1

A mixture of 6 (400.00 mg, 2.17 mmol) and 3 (868.04 mg, 4.34 mmol) in toluene (20 mL) was added Pd(dba)$_2$ (124.84 mg, 217.00 μmol), Cs$_2$CO$_3$ (1.41 g, 4.34 mmol) and Xantphos (125.62 mg, 217.00 μmol) in one portion at rt. under N$_2$ atmosphere. The mixture was then heated at 110° C. and stirred for 18 hrs. LCMS showed the reaction was completed. The mixture was cooled to rt. and filtered. The filtrate was concentrated in reduced pressure at 60° C. The residue was purified by prep-HPLC to afford Compound 1 (292.00 mg, yield: 44.06%).

LCMS: m/z, 304 (M+H)$^+$;

$^1$H NMR (400 MHz, CDCl3): δ 8.54 (d, J=4.65 Hz, 1H), 7.63 (td, J=7.76, 1.59 Hz, 1H), 7.38 (d, J=7.83 Hz, 1H), 7.21 (dd, J=7.09, 5.38 Hz, 1H), 6.66 (d, J=7.58 Hz, 1H), 6.54 (s, 1H), 6.38-6.45 (m, 1H), 3.72 (d, J=9.05 Hz, 1H), 3.41-3.54 (m, 3H), 2.19 (dt, J=8.31, 4.40 Hz, 1H), 1.43 (dd, J=8.07, 4.89 Hz, 1H), 0.98 (t, J=5.01 Hz, 1H).

Example Compound 2

Preparation of 3-(4-fluorophenyl)-1-(pyridin-2-ylethynyl)-3-azabicyclo[3.1.0]hexane

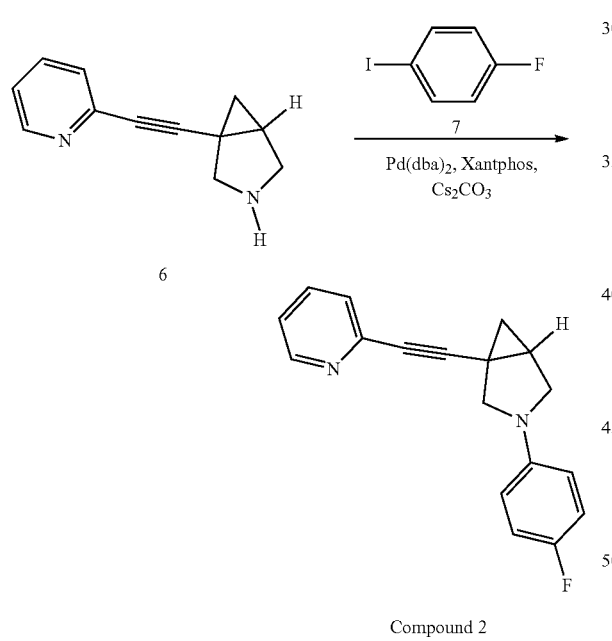

Compound 2

Experimental Section

Procedure for Preparation of Compound 2

To a mixture of 6 (100.00 mg, 542.77 μmol) and 7 (361.49 mg, 1.63 mmol) in toluene (5.00 mL) was added Pd(dba)$_2$ (31.21 mg, 54.28 μmol), Cs$_2$CO$_3$ (353.69 mg, 1.09 mmol) and Xantphos (31.41 mg, 54.28 μmol) in one portion at rt. under N$_2$ atmosphere. The mixture was then heated to 110° C. and stirred for 18 hrs. LCMS showed the reaction was completed. The mixture was cooled to rt. and filtered. The filtrate was concentrated in reduced pressure at 60° C. The residue was purified by prep-HPLC to afford the desired product Compound 2 (15.00 mg, yield: 9.72%).

LCMS: m/z, 279 (M+H)$^+$;

$^1$HNMR (400 MHz, CDCl3): δ 8.48 (d, J=4.85 Hz, 1H), 7.56 (td, J=7.72, 1.76 Hz, 1H), 7.32 (d, J=7.94 Hz, 1H), 7.09-7.17 (m, 1H), 6.86 (t, J=8.71 Hz, 2H), 6.37-6.47 (m, 2H), 3.69 (d, J=8.60 Hz, 1H), 3.48 (d, J=8.82 Hz, 1H), 3.19-3.35 (m, 2H), 2.07 (dt, J=8.21, 4.38 Hz, 1H), 1.27 (dd, J=8.05, 4.52 Hz, 1H), 1.05 (t, J=4.63 Hz, 1H).

Example Compound 3

Preparation of 1-(pyridin-2-ylethynyl)-3-(4-(trifluoromethoxy)phenyl)-3-azabicyclo[3.1.0]hexane

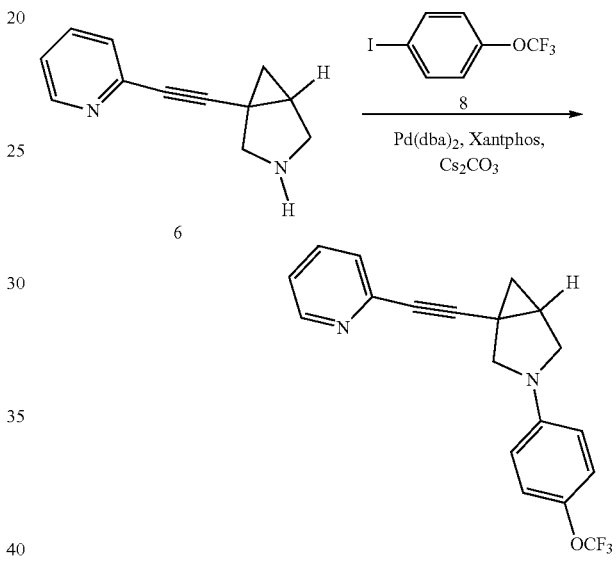

Compound 3

Experimental Section

Procedure for Preparation of Compound 3

To a mixture of 6 (100.00 mg, 542.77 μmol) and 8 (299.73 mg, 1.09 mmol) in toluene (5.00 mL) was added Pd(dba)$_2$ (31.21 mg, 54.28 μmol), Cs$_2$CO$_3$ (353.69 mg, 1.09 mmol) and Xantphos (31.41 mg, 54.28 μmol) in one portion at rt. under N$_2$ atmosphere. The mixture was then heated to 110° C. and stirred for 18 hours. LCMS showed the reaction was completed. The mixture was cooled to rt. and filtered. The filtrate was concentrated in reduced pressure at 60° C. The residue was purified by prep-HPLC to afford the desired product Compound 3 (8.00 mg, yield: 4.36%).

LCMS: m/z, 345 (M+H)$^+$;

$^1$HNMR (400 MHz, CDCl3): δ 8.54 (d, J=4.85 Hz, 1H), 7.63 (td, J=7.72, 1.76 Hz, 1H), 7.39 (d, J=7.72 Hz, 1H), 7.20 (dd, J=7.06, 5.51 Hz, 1H), 7.07 (d, J=8.60 Hz, 2H), 6.51 (d, J=9.26 Hz, 2H), 3.76 (d, J=8.82 Hz, 1H), 3.55 (d, J=9.04 Hz, 1H), 3.32-3.46 (m, 2H), 2.10-2.19 (m, 1H), 1.36 (dd, J=8.05, 4.52 Hz, 1H), 1.05 (t, J=4.63 Hz, 1H).

Example Compound 4

Preparation of 3-(5-fluoropyridin-3-yl)-1-(pyridin-2-ylethynyl)-3-azabicyclo[3.1.0]hexane

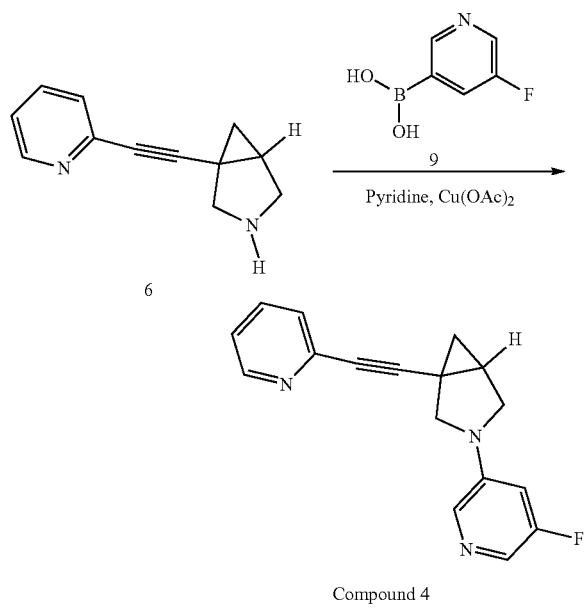

Compound 4

Experimental Section

Procedure for Preparation of Compound 4

To a mixture of 6 (100.00 mg, 542.77 μmol) and 9 (152.96 mg, 1.09 mmol) in DCM (20 mL), was added Cu(OAc)$_2$ (197.17 mg, 1.09 mmol) and Pyridine (128.80 mg, 1.63 mmol) in one portion at rt. in the open air. The mixture was stirred at rt. for 15 hrs. TLC showed the reaction was completed. The mixture was concentrated in reduced pressure. The residue was purified by prep-TLC followed by prep-HPLC purification to afford the desired product Compound 4 (30.00 mg, yield: 19.64%).

LCMS: m/z, 280.0 (M+H)$^+$;

$^1$HNMR (400 MHz, CDCl3): δ 8.55-8.54 (m, 1H), 7.84 (s, 1H), 7.79 (s, 1H), 7.64-7.61 (m, 1H), 7.40-7.38 (m, 1H), 7.23-7.21 (m, 1H), 6.54-6.51 (m, 1H), 3.78-3.76 (m, 1H), 3.57-3.55 (m, 1H), 3.48-3.45 (m, 2H), 2.20-2.18 (m, 1H), 1.44-1.40 (m, 1H), 1.04-1.01 (m, 1H).

Example Compound 5

Preparation of 3-(phenylsulfonyl)-1-(pyridin-2-ylethynyl)-3-azabicyclo[3.1.0]hexane

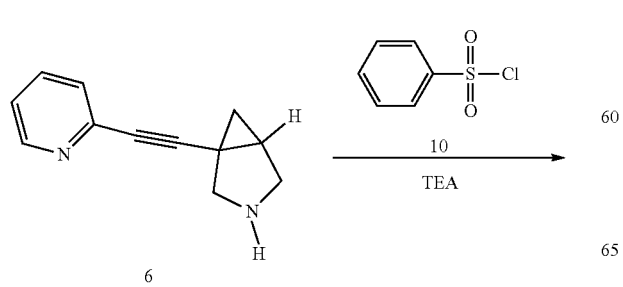

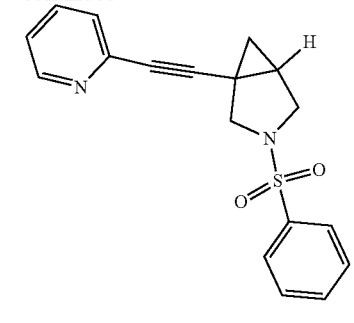

Compound 5

Experimental Section

Procedure for Preparation of Compound 5

To a mixture of 6 (150.00 mg, 814.16 μmol) and TEA (247.15 mg, 2.44 mol) in DCM (15 mL), was added 10 (287.59 mg, 1.63 mmol) dropwise at rt. The mixture was stirred at rt. for 3 hr. LCMS showed the reaction was completed. The mixture was quenched with water (10 mL), the aqueous phase was extracted with DCM (20 mL×2). The combined organic phase was washed with saturated brine (5 mL), dried over anhydrous Na$_2$SO4, filtered and concentrated in vacuo. The residue was purified by prep-HPLC to afford product Compound 5 (100.00 mg, yield: 33.51%).

LCMS: m/z, 325.0 (M+H)$^+$;

1HNMR (400 MHz, CDCl3): δ 8.51-8.49 (m, 1H), 7.80-7.79 (m, 2H), 7.63-7.54 (m, 4H), 7.33-7.31 (m, 1H), 7.20-7.18 (m, 1H), 3.76-3.74 (m, 1H), 3.60-3.58 (m, 1H), 3.18-3.12 (m, 2H), 1.90-1.88 (m, 1H), 1.23-1.20 (m, 1H), 1.14-1.11 (m, 1H).

Example Compound 6

Preparation of 3-(5-fluoropyridin-2-yl)-1-(pyridin-2-ylethynyl)-3-azabicyclo[3.1.0]hexane

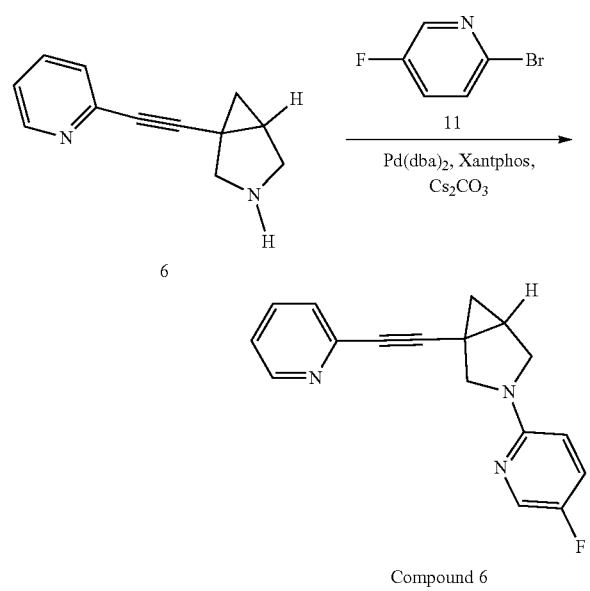

Compound 6

Experimental Section

Procedure for Preparation of Compound 6

A mixture of 6 (100.00 mg, 542.77 μmol), 11 (191.04 mg, 1.09 mmol), Xantphos (31.41 mg, 54.28 μmol), Cs$_2$CO$_3$ (530.54 mg, 1.63 mmol) and Pd(dba)$_2$ (31.21 mg, 54.28 μmol) were taken up into a microwave tube in toluene (8 mL). The sealed tube was heated at 130° C. for 1 hr under microwave. TLC showed the starting material was consumed completely, after cooling to rt., the reaction mixture was concentrated in reduced pressure. The residue was purified by prep-TLC followed by prep-HPLC purification to afford Compound 6 (17.00 mg, yield: 5.10%).

LCMS: m/z, 280.0 (M+H)$^+$;

$^1$HNMR (400 MHz, CDCl3): δ 8.54-8.53 (m, 1H), 8.01-7.99 (m, 1H), 7.64-7.62 (m, 1H), 7.39-7.37 (m, 1H), 7.23-7.20 (m, 2H), 6.31-6.28 (m, 1H), 3.92-3.89 (m, 1H), 3.75-3.72 (m, 1H), 3.57-3.50 (m, 2H), 2.16-2.12 (m, 1H), 1.39-1.36 (m, 1H), 1.02-1.00 (m, 1H).

Example Compound 7

Preparation of 3-fluoro-5-(1-(pyrazin-2-ylethynyl)-3-azabicyclo[3.1.0]hexan-3-yl) benzonitrile

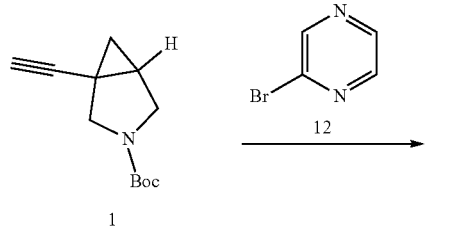

1

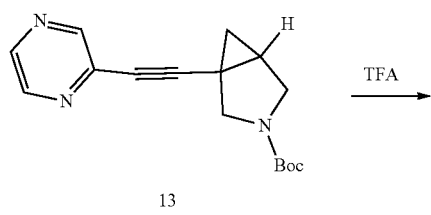

13

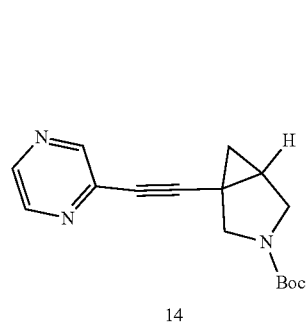

14

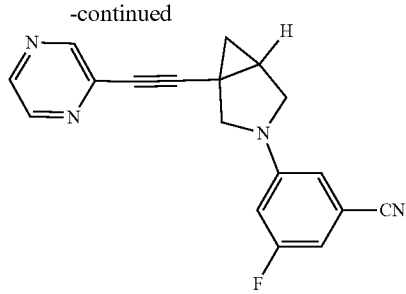

Compound 7

Experimental Section

Procedure for Preparation of 13

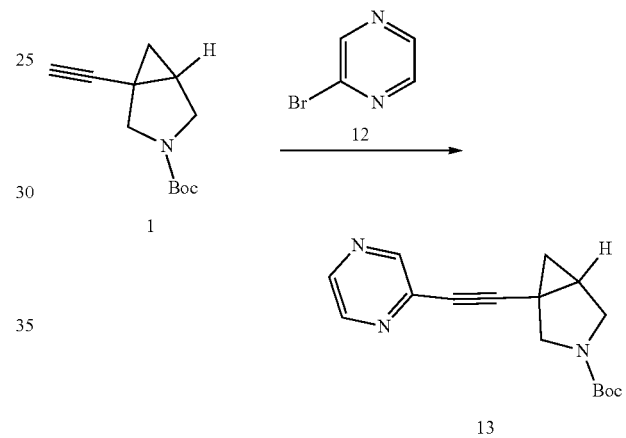

13

To a solution of 1 (300.00 mg, 1.45 mmol) and 12 (345.16 mg, 2.17 mmol) in THF (5 mL), Pd(PPh$_3$)$_2$Cl$_2$ (50.80 mg, 72.37 μmol), TEA (439.38 mg, 4.34 mmol) and CuI (27.57 mg, 144.74 μmol) were added, the reaction mixture was taken up into a microwave tube. The sealed tube was heated at 90° C. for 1 hr under microwave. TLC showed the starting material was consumed completely, the reaction mixture was diluted with EA (10 mL), washed with brine (5 mL), dried over anhydrous Na$_2$SO$_4$, concentrated in vacuo to give the crude product which was purified by prep-HPLC to afford product 13 (300.00 mg, yield: 72.41%).

Procedure for Preparation of 14

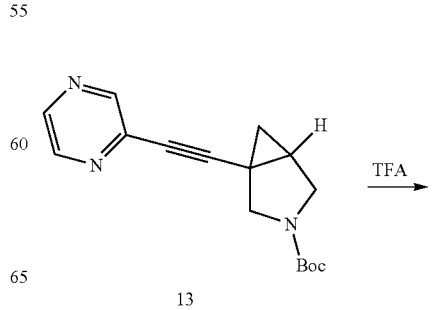

13

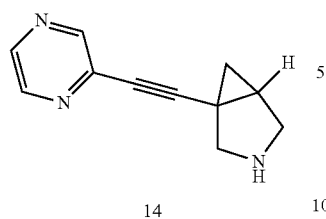

14

Compound 13 (300.00 mg, 1.05 mmol) was dissolved in TFA (1 mL) and DCM (5 mL), the solution was stirred at rt. for 3 hr, TLC showed the reaction was completed. The reaction mixture was concentrated to dryness and the residue was basified by adding 15% aq. NaOH (10 mL), extracted with EA (10 mL×3). The combined organic phase was washed with water (10 mL), brine (10 mL), dried over anhydrous $Na_2SO_4$, and concentrated to dryness to afford product 14 (160.00 mg, crude), which was used for the next step directly.

Procedure for Preparation of Compound 7

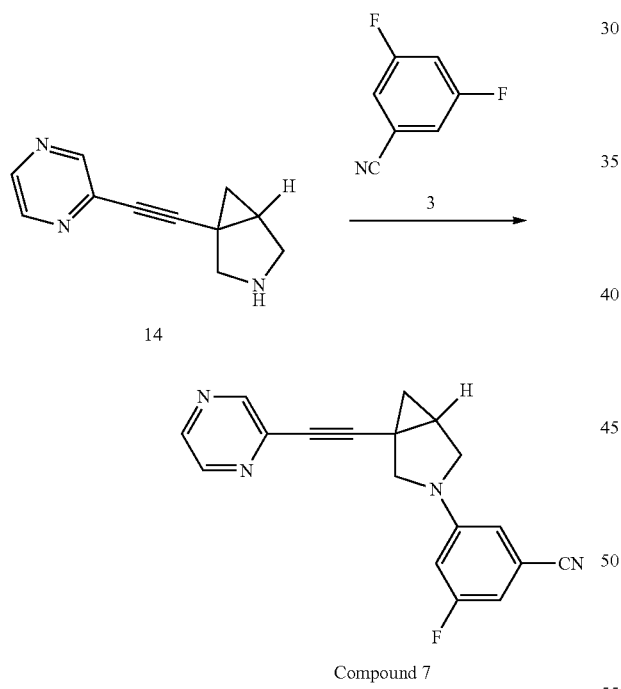

A mixture of 3 (160.00 mg, 863.84 μmol), 14 (320.06 mg, 1.30 mmol), Pd(dba)$_2$ (49.67 mg, 86.38 μmol), $Cs_2CO_3$ (844.37 mg, 2.59 mmol) and Xantphos (41.18 mg, 86.38 μmol) were taken up into a microwave tube in toluene (4 mL). The sealed tube was heated at 120° C. for 1 hr under microwave. TLC showed the starting material was consumed completely. After cooling to rt., EA (10 mL) and water (10 mL) were added. The aqueous layer was extracted with EA (5 mL×3). The combined organic layers were washed with brine (5 mL), dried over anhydrous $Na_2SO_4$, concentrated in vacuo to give the crude product which was purified by prep-HPLC to afford product Compound 7 (85.00 mg, yield: 32.33%).

LCMS: m/z, 305.1 (M+H)$^+$;

$^1$HNMR (400 MHz, CDCl3): δ 1.06 (t, J=5.2 Hz, 1H), 1.48 (dd, J=5.2, 8.0 Hz, 1H), 2.25 (t, J=4.0 Hz, 1H), 3.48-3.53 (m, 3H), 3.76 (d, J=9.2 Hz, 1H), 6.44 (d, J=11.8 Hz, 1H), 6.57 (s, 1H), 6.69 (d, J=7.6 Hz, 1H), 8.47 (d, J=2.8 Hz, 1H), 8.52 (s, 1H), 8.64 (s, 1H).

Example Compound 8

Preparation of 3-fluoro-5-(1-(pyrimidin-2-ylethynyl)-3-azabicyclo[3.1.0]hexan-3-yl) benzonitrile

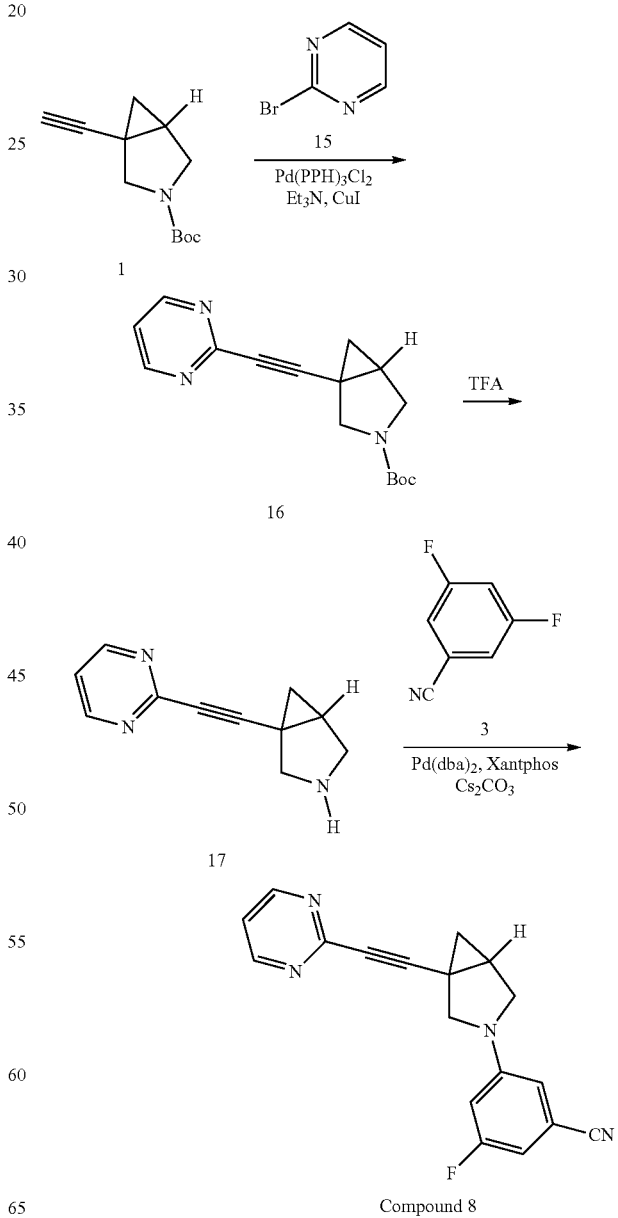

Experimental Section

Procedure for Preparation of 16

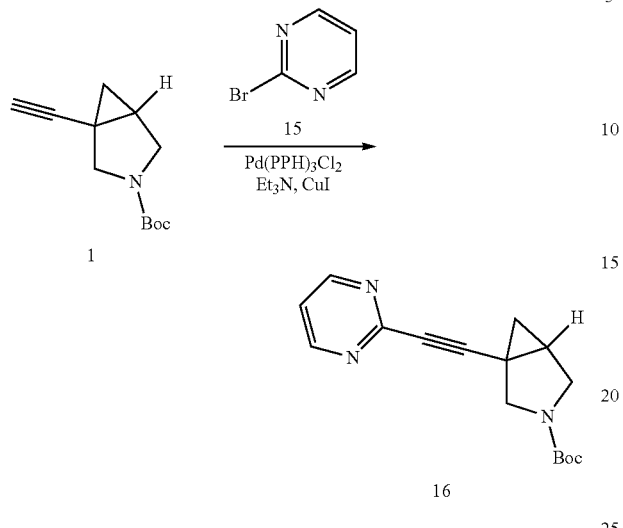

A mixture of 1 (300.00 mg, 1.45 mmol), 15 (460.21 mg, 2.89 mmol), CuI (27.57 mg, 144.74 μmol), TEA (439.38 mg, 4.34 mmol) and Pd(PPh$_3$)$_2$Cl$_2$ (50.80 mg, 72.37 μmol,) were taken up into a microwave tube in THF (10 mL). The sealed tube was heated at 90° C. for 1 hr under microwave. LCMS showed the starting material was consumed completely. After cooling to rt., the reaction mixture was concentrated under reduced pressure. The residue was purified by silica gel chromatography to afford product 16 (300.00 mg, yield: 61.89%).

LCMS: m/z, 230.2 (M+H)$^+$.

Procedure for Preparation of 17

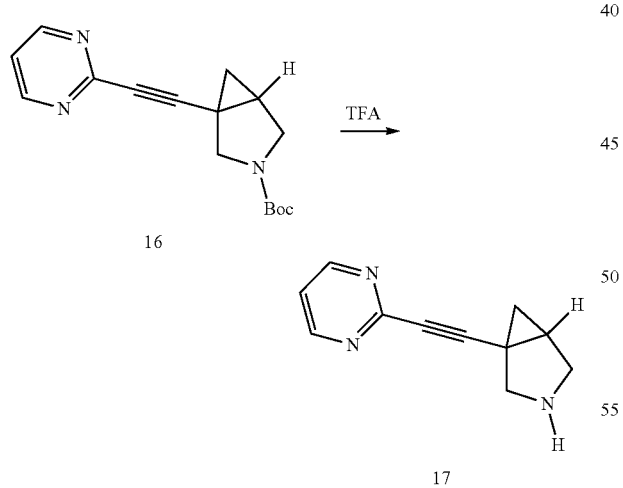

To a solution of 16 (250.00 mg, 876.15 μmol) in DCM (4.5 mL), was added TFA (1.5 mL) in one portion at rt. The mixture was stirred at rt. for 3 hr. LCMS showed the reaction was completed. The reaction mixture was added saturated Na$_2$CO$_3$ (3 mL). The aqueous phase was extracted with DCM (20 mL×3). The combined organic phase was dried over anhydrous Na$_2$SO$_4$, filtered and concentrated in vacuo to afford product 17 (150.00 mg, crude).

LCMS: m/z, 186.1 (M+H)$^+$.

Procedure for Preparation of Compound 8

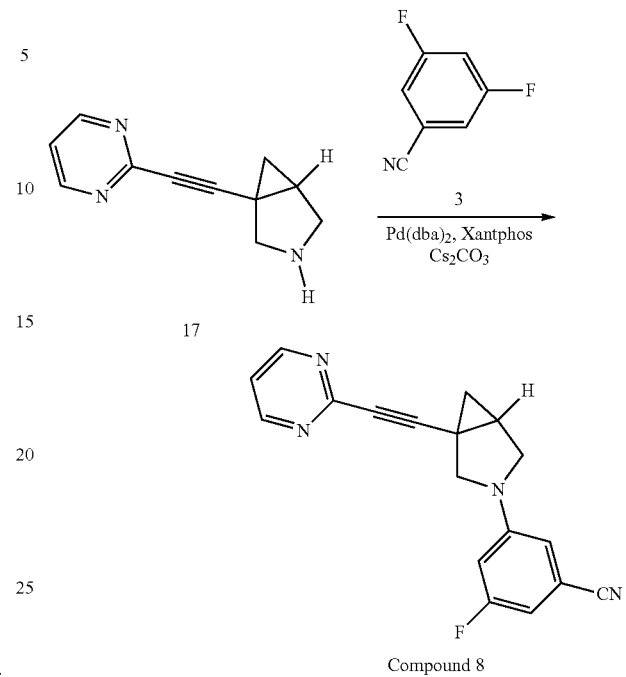

Compound 8

A mixture of 17 (150.00 mg, 809.85 μmol), 3 (400.08 mg, 1.62 mmol), Xantphos (46.86 mg, 80.98 μmol), Cs$_2$CO$_3$ (791.59 mg, 2.43 mmol) and Pd(dba)$_2$ (46.57 mg, 80.98 μmol) were taken up into a microwave tube in toluene (8 mL). The sealed tube was heated at 110° C. for 1 hr under microwave. LCMS showed the starting material was consumed completely, after cooling to rt., the reaction mixture was concentrated in reduced pressure. The residue was purified by prep-HPLC to afford product Compound 8 (30.00 mg, yield: 12.15%).

LCMS: m/z, 305.1 (M+H)$^+$;

$^1$HNMR (400 MHz, CDCl3): δ 8.71-8.69 (m, 1H), 7.25-7.22 (m, 1H), 6.68-6.66 (m, 1H), 6.54 (s, 1H), 6.43-6.40 (m, 1H), 3.75-3.73 (m, 1H), 3.54-3.52 (m, 2H), 3.46-3.44 (m, 1H), 2.29-2.25 (m, 1H), 1.53-1.49 (m, 1H), 1.05-1.02 (m, 1H).

Example Compound 9

Preparation of 3-fluoro-S-(1-((3-methylpyridin-2-yl) ethynyl)-3-azabicyclo[3.1.0]]hexan-3-yl) benzonitrile

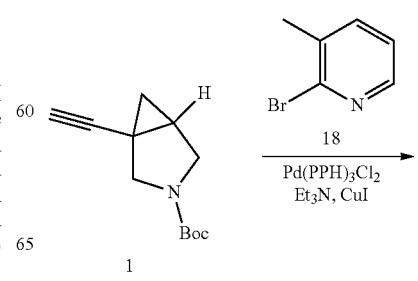

-continued

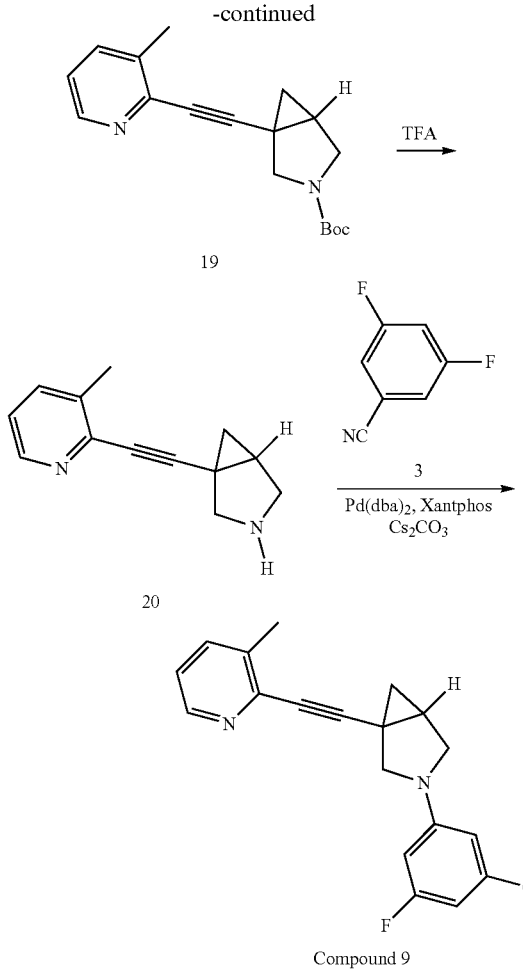

Experimental Section

Procedure for Preparation of 19

A mixture of 1 (500.00 mg, 2.41 mmol), 18 (539.46 mg, 3.14 mmol), CuI (22.97 mg, 120.62 μmol), Et₃N (732.31 mg, 7.24 mmol) and Pd(PPh₃)₂Cl₂ (84.66 mg, 120.62 μmol) were taken up into a microwave tube in THF (8 mL). The sealed tube was heated at 95° C. for 1 hr under microwave. LCMS showed the starting material was consumed completely and the title compound was detected. After cooling to rt., EA (80 mL) and saturated aqueous of Na₂CO₃ (20 mL) were added. The aqueous layer was extracted with EA (40 mL×2). The combined organic layers were washed with brine (30 mL), dried over anhydrous Na₂SO₄, concentrated in vacuo to give the crude product, which was purified by column chromatography to afford product 19 (600.00 mg, yield: 83.44%).

LCMS: m/z, 299.1 (M+H)⁺.

Procedure for Preparation of 20

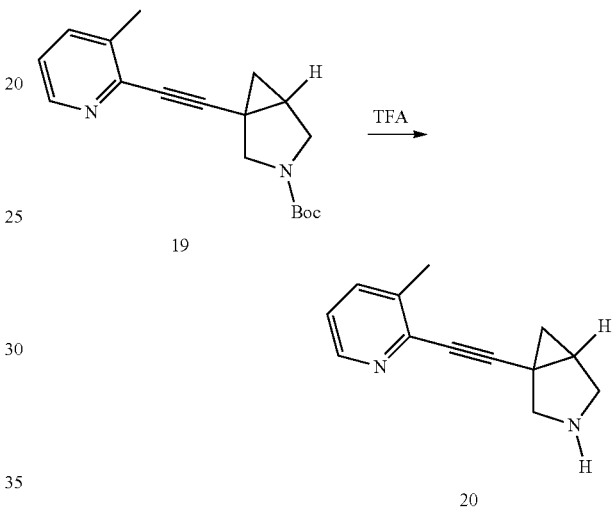

To a solution of 19 (350.00 mg, 1.17 mmol) in DCM (5 mL) was added TFA (1 mL) at rt., the mixture was stirred at rt. for 2 hr. LCMS showed the starting material was consumed completely and the title compound was detected, then, the reaction mixture was concentrated to dryness and diluted with water (10 mL). The aqueous phase was basified with saturated aqueous NaHCO₃ till pH=7, the aqueous layer was extracted with EA (40 mL×2), the organic layer was washed with brine (20 mL), dried over anhydrous Na₂SO₄ and evaporated in vacuo to afford product 20 (200.24 mg, crude).

LCMS: m/z, 199.2 (M+H)⁺.

Procedure for Preparation of Compound 9

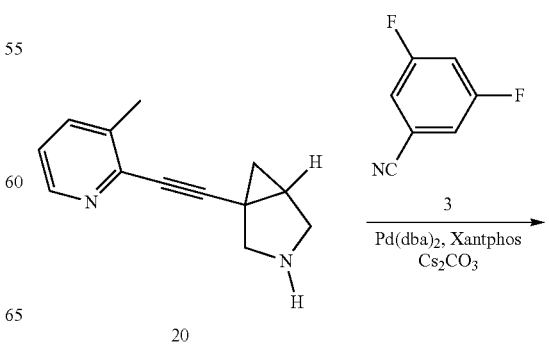

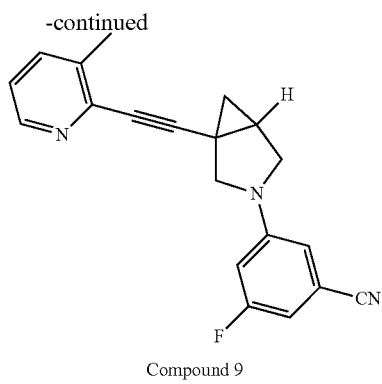

Compound 9

A mixture of 20 (150.00 mg, 756.58 μmol), 3 (224.26 mg, 907.90 μmol), Xantphos (3.61 mg, 7.57 μmol), Cs$_2$CO$_3$ (739.53 mg, 2.27 mmol) and Pd(dba)$_2$ (4.35 mg, 7.57 μmol) were taken up into a microwave tube in DMF (8 mL). The sealed tube was heated at 120° C. for 1 hr under microwave. TLC showed the starting material was consumed completely. After cooling to rt., EA (80 mL) and saturated aqueous of Na$_2$CO$_3$ (20 mL) were added. The aqueous layer was extracted with EA (60 mL×2). The combined organic layers were washed with brine (30 mL), dried over anhydrous Na$_2$SO$_4$, concentrated in reduced pressure to give the crude product, which was purified by prep-HPLC to afford product Compound 9 (59.00 mg, yield: 24.42%).

LCMS: m/z, 318.1 (M+H)$^+$;

$^1$HNMR (400 MHz, CDCl3): δ 8.38 (d, J=4.19 Hz, 1H), 7.51-7.47 (m, 1H), 7.15-7.12 (m, 1H), 6.68-6.62 (m, 1H), 6.55 (s, 1H), 6.45-6.41 (m, 1H), 3.77-3.74 (m, 1H), 3.42-3.58 (m, 3H), 2.42 (s, 3H), 2.14-2.25 (m, 1H), 1.38-1.51 (m, 1H), 1.00 (t, J=4.96 Hz, 1H).

Example Compound 10

Preparation of 3-phenyl-1-(pyridin-2-ylethynyl)-3-azabicyclo[3.1.0]hexane

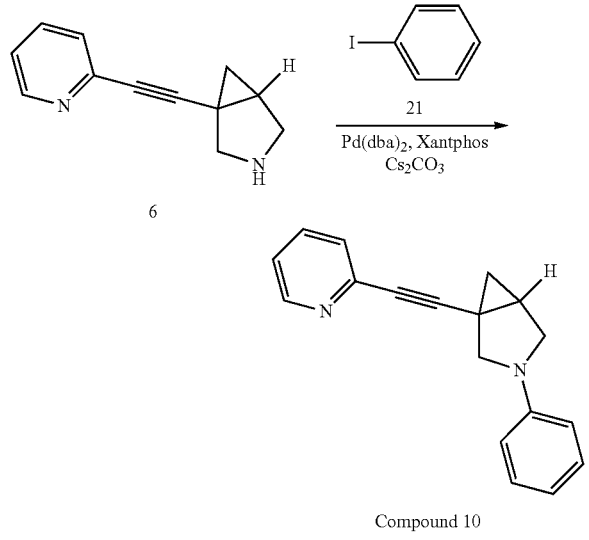

Compound 10

Experimental Section

Procedure for Preparation of Compound 10

To a mixture of 6 (100.00 mg, 542.77 μmol) and 21 (110.73 mg, 542.77 μmol) in toluene (5 mL) was added Pd(dba)$_2$ (31.21 mg, 54.28 μmol), Cs$_2$CO$_3$ (353.69 mg, 1.09 mmol) and Xantphos (31.41 mg, 54.28 μmol) in one portion at rt. under N$_2$ atmosphere. The mixture was then heated to 110° C. and stirred for 18 hrs. LCMS showed the reaction was completed. The mixture was cooled to rt. and filtered. The filtrate was concentrated in reduced pressure at 60° C. The residue was purified by prep-HPLC to afford product Compound 10 (9.00 mg, yield: 6.14%).

LCMS: m/z, 261.1 (M+H)$^+$;

$^1$HNMR (400 MHz, CDCl$_3$): δ ppm 8.54 (d, J=4.41 Hz, 1H), 7.55-7.69 (m, 1H), 7.40 (s, 1H), 7.21 (d, J=7.72 Hz, 3H), 6.72 (t, J=7.28 Hz, 1H), 6.57 (d, J=8.16 Hz, 2H), 3.80 (d, J=8.82 Hz, 1H), 3.59 (d, J=9.26 Hz, 1H), 3.31-3.46 (m, 2H), 2.10-2.18 (m, 1H), 1.34 (dd, J=8.05, 4.52 Hz, 1H), 1.08 (t, J=4.63 Hz, 1H).

Example Compound 11

Preparation of 3-fluoro-5-(1-(pyridazin-3-ylethynyl)-3-azabicyclo[3.1.0]hexan-3-yl)benzonitrile

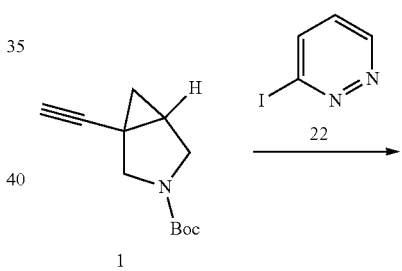

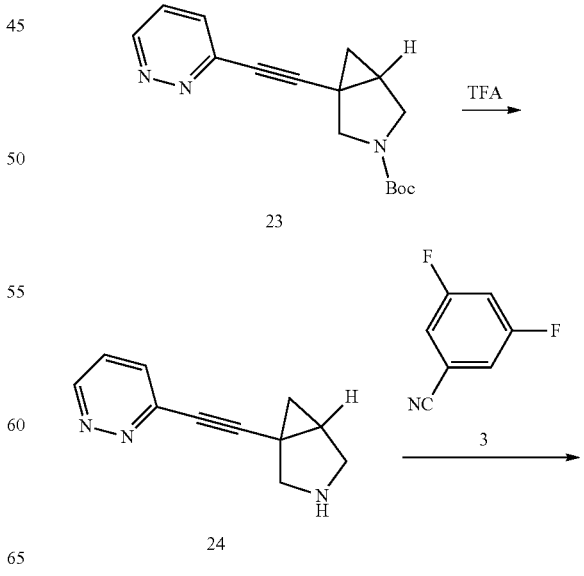

35

-continued

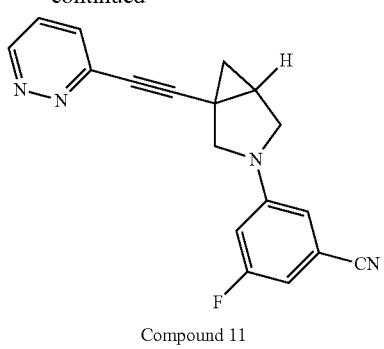

Compound 11

Experimental Section

Procedure for Preparation of 23

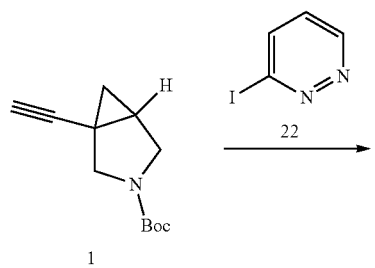

A mixture of 1 (300.54 mg, 1.45 mmol), 22 (448.01 mg, 2.17 mmol), Pd(PPh$_3$)$_2$Cl$_2$ (101.78 mg, 145.00 μmol), Et$_3$N (293.45 mg, 2.90 mmol) and CuI (27.62 mg, 145.00 μmol) were taken up into a microwave tube in THF (10 mL). The sealed tube was degassed with N$_2$ twice and then heated at 90° C. for 1 hr under microwave. TLC showed the starting material was consumed. After cooling to rt., EA (60 mL) and water (60 mL) were added. The aqueous layer was extracted with EA (60 mL×2). The combined organic layers were washed with brine (60 mL), dried over anhydrous Na$_2$SO$_4$, concentrated in vacuo to give the crude product, which was purified by chromatograph column to give product 23 (220.00 mg, yield: 53.17%).

LCMS: m/z, 286.1 (M+H)$^+$.

36

Procedure for Preparation of 24

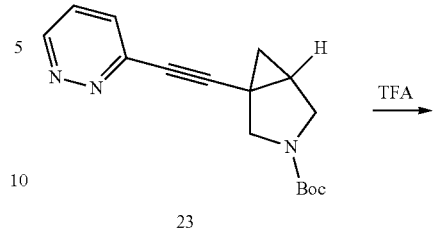

To a mixture of 23 (220.00 mg, 771.01 μmol) in DCM (8 mL) was added TFA (2 mL) in one portion at rt. The mixture was stirred at rt. for 1 hr. LCMS showed the reaction was completed. The mixture was concentrated in reduced pressure at 50° C. The residue was poured into saturated NaHCO$_3$ solution (30 mL) and stirred for 2 min. The aqueous phase was extracted with EA (20 mL×3). The combined organic phase was washed with saturated brine (20 mL×1), dried over anhydrous Na$_2$SO$_4$, filtered and concentrated in vacuo to afford product 24 (100.00 mg, crude).

LCMS: m/z, 186.1 (M+H)$^+$.

Procedure for Preparation of Compound 11

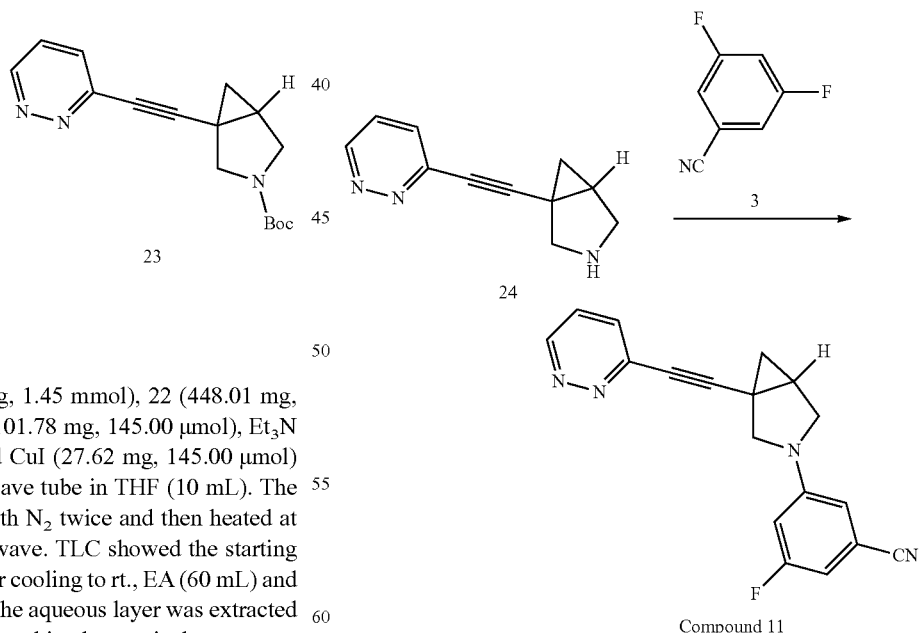

To a mixture of 24 (80.00 mg, 431.92 μmol) and 3 (160.03 mg, 647.88 μmol) in toluene (5 mL) was added Pd(dba)$_2$ (24.84 mg, 43.19 μmol), Cs$_2$CO$_3$ (281.46 mg, 863.84 μmol) and Xantphos (24.99 mg, 43.19 μmol) in one portion at rt. under N$_2$ atmosphere. The mixture was then heated to 110°

C. and stirred for 1 hr. TLC showed the reaction was completed. The mixture was cooled to rt. and filtered. The filtrate was concentrated in reduced pressure at 60° C. to give the residue, which was purified by prep-HPLC to give the desired product Compound 11 (3.40 mg, yield: 2.53%).

LCMS: m/z, 305.1 (M+H)+;

$^1$H NMR (400 MHz, CDCl$_3$): δ 9.05 (dd, J=5.01, 1.59 Hz, 1H), 7.42-7.50 (m, 1H), 7.37 (dd, J=8.44, 5.01 Hz, 1H), 6.62 (d, J=7.83 Hz, 1H), 6.50 (s, 1H), 6.34-6.40 (m, 1H), 3.67-3.74 (m, 1H), 3.47 (s, 3H), 2.20 (dt, J=8.31, 4.40 Hz, 1H), 1.44 (dd, J=8.19, 5.01 Hz, 1H), 1.00 (t, J=5.01 Hz, 1H).

Example Compound 12

Preparation of compound 3-(1-((2-chloropyridin-4-yl)ethynyl)-3-azabicyclo[3.1.0]hexan-3-yl)-5-fluorobenzonitrile

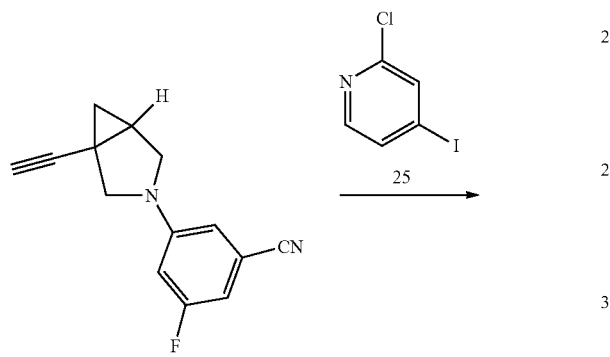

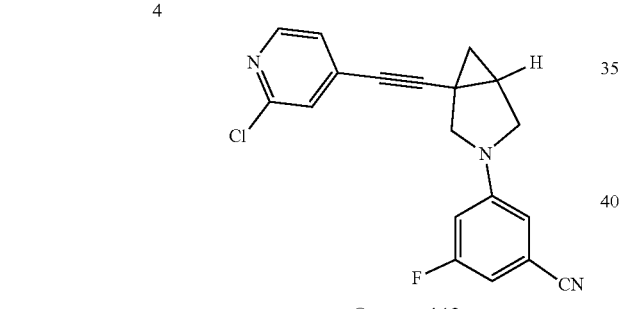

Compound 12

Experimental Section

Procedure for Preparation of Compound 12

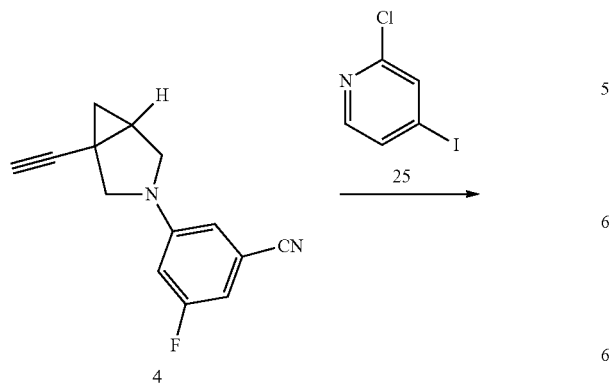

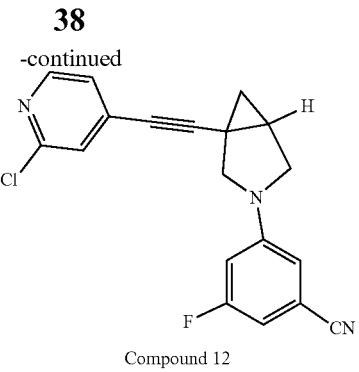

Compound 12

A mixture of compound 4 (30.0 mg, 132.6 μmol), 25 (31.7 mg, 132.6 μmol), CuI (2.5 mg, 13.2 μmol), PPh$_3$ (3.4 mg, 13.2 μmol) and Pd(PPh$_3$)$_2$Cl$_2$ (4.6 mg, 6.63 μmol) in TEA (12 mL) and THF (12 mL) was degassed and purged with N$_2$ for 3 times, and then the mixture was stirred at 35~40° C. for 16 hrs under N$_2$ atmosphere. LCMS showed 4 was consumed completely. The reaction mixture was concentrated under reduced pressure to give a residue. The residue was purified by prep-HPLC to give the desired product Compound 12 (15 mg, yield: 33%).

LCMS: m/z, 337.1 (M+H)+;

$^1$HNMR (400 MHz, CDCl$_3$): δ 8.26 (d, J=5.2 Hz, 1H), 7.24 (s, 1H), 7.10 (dd, J=4.8 Hz, 1H), 6.62 (d, J=7.2 Hz, 1H), 6.5 (s, 1H), 6.37 (dt, J=13.6 Hz, 1H), 3.67 (d, J=9.2 Hz, 1H), 3.48 (m, 3H), 2.14 (m, 1H), 1.36 (dd, J=8.4 Hz, 1H), 0.99 (t, J=10 Hz, 1H).

Example Compound 13

Preparation of 3-fluoro-5-(1-((6-methylpyridin-2-yl)ethynyl)-3-azabicyclo[3.1.0]hexan-3-yl) benzonitrile

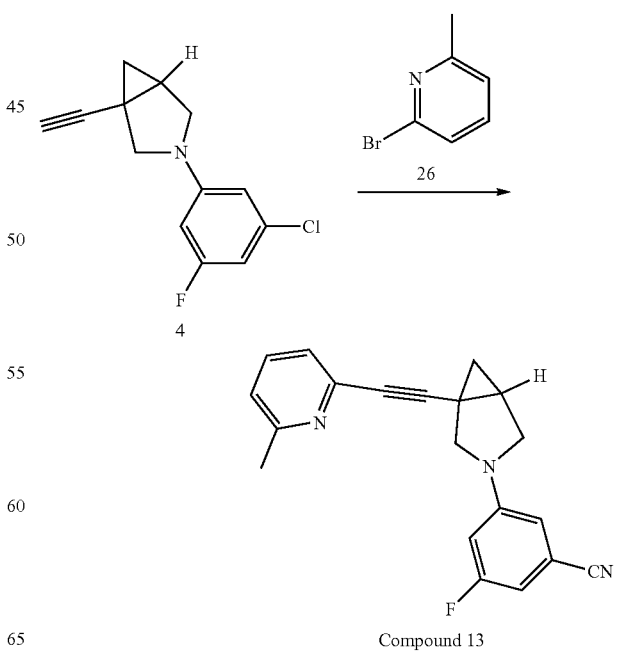

Compound 13

Experimental Section

Procedure for Preparation of Compound 13

A mixture of compound 4 (70.0 mg, 309 μmol), 26 (53.0 mg, 309 μmol), CuI (5.8 mg, 30.9 μmol), PPh₃ (8.1 mg, 30.9 μmol) and Pd(PPh₃)₂Cl₂ (10.8 mg, 15.4 μmol) in TEA (1 mL) and THF (1 mL) was degassed and purged with N₂ for 3 times, and then the mixture was stirred at rt. for 1 hr under N₂ atmosphere. LCMS showed that 4 was consumed completely. The reaction mixture was quenched by addition water (10 ml) at rt., and then diluted with EA (15 mL) and extracted with EA (15 mL×3). The combined organic layers were washed with NaCl (20 mL×2), filtered and concentrated under reduced pressure to give a residue. The residue was purified by prep-HPLC to give the desired product Compound 13 (23 mg, yield: 23%).

LCMS: m/z, 317.1 (M+H)⁺;

¹HNMR (400 MHz, CDCl₃): δ 7.57 (s, 1H), 7.27 (d, J=7.6 Hz, 1H), 7.13 (d, J=7.2 Hz, 1H), 6.70 (d, J=7.2 Hz, 1H), 6.57 (s, 1H), 6.45 (d, J=11.6 Hz, 1H), 3.75 (d, J=9.2 Hz, 1H), 3.55 (m, 3H), 2.85 (s, 3H), 2.23 (s, 1H), 1.48 (s, 1H), 1.01 (t, J=9.6 Hz, 1H).

Example Compound 14

Preparation of 3-(1-(6-chloropyridin-2-yl)-3-azabicyclo[3.1.0]hexan-3-yl)-5-fluorobenzonitrile

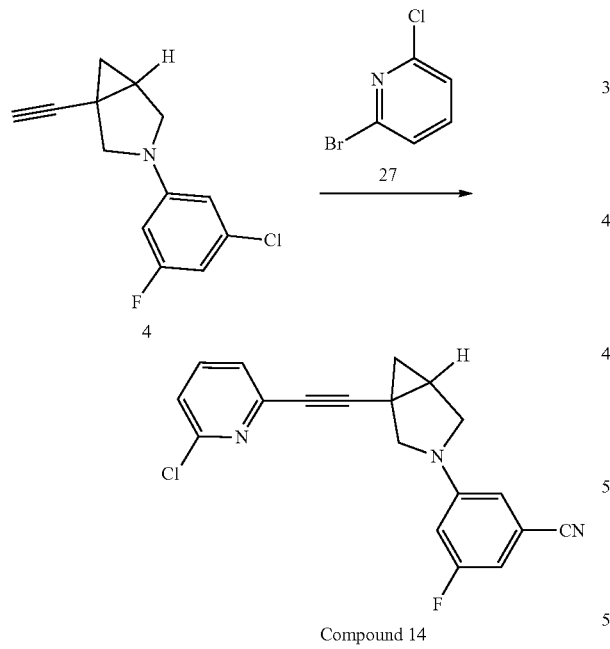

Experimental Section

Procedure for Preparation of Compound 14

A mixture of compound 4 (80.0 mg, 353 μmol), 27 (68.0 mg, 353 μmol), CuI (6.7 mg, 35.3 μmol), PPh₃ (9.2 mg, 35.3 μmol) and Pd(PPh₃)₂Cl₂ (12.4 mg, 17.6 μmol) in TEA (1 mL) and THF (1 mL) was degassed and purged with N₂ for 3 times, and then the mixture was stirred at 35~40° C. for 16 hrs under N₂ atmosphere. LCMS showed 4 was consumed completely. The reaction mixture was quenched by addition water (10 ml) at rt., and then diluted with EA (15 mL) and extracted with EA (15 mL×3). The combined organic layers were washed with brine (20 mL×2), filtered and concentrated under reduced pressure to give a residue. The residue was purified by prep-HPLC to give the desired product Compound 14 (26 mg, yield: 21%).

LCMS: m/z, 337.1 (M+H)⁺;

¹HNMR (400 MHz, CDCl₃): δ 7.57 (t, J=16 Hz, 1H), 7.35 (t, J=18 Hz, 2H), 6.71 (d, J=7.6 Hz, 1H), 6.57 (s, 1H), 6.46 (d, J=11.6 Hz, 1H), 3.76 (d, J=8.8 Hz, 1H), 3.56 (m, 3H), 2.25 (m, 1H), 1.48 (m, 1H), 1.04 (t, J=10 Hz, 1H).

Example Compound 15

Preparation of 3-fluoro-5-(1-((6-methoxypyridin-2-yl)ethynyl)-3-azabicyclo[3.1.0]hexan-3-yl) benzonitrile

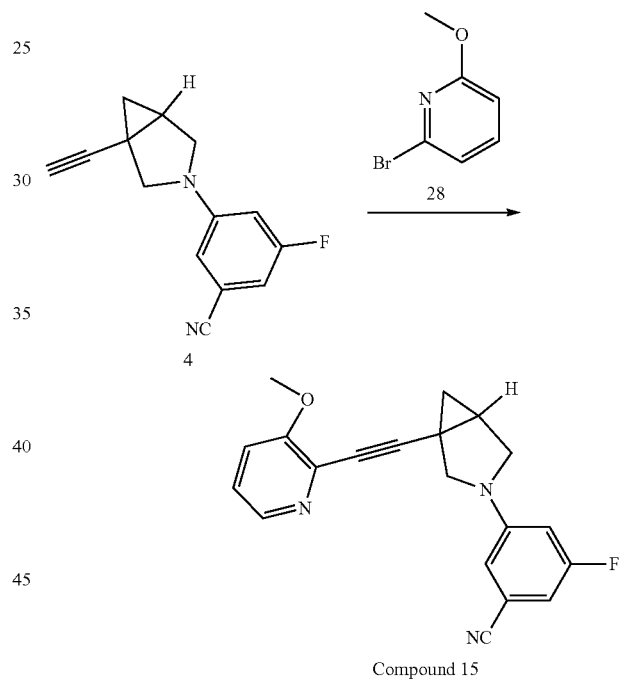

Experimental Section

Procedure for Preparation of Compound 15

A mixture of compound 4 (80.0 mg, 353 μmol), 28 (66.4 mg, 353 μmol), CuI (6.7 mg, 35.3 μmol), PPh₃ (9.2 mg, 35.3 μmol) and Pd(PPh₃)₂Cl₂ (12.4 mg, 17.6 μmol) in TEA (1 mL) and THF (1 mL) was degassed and purged with N₂ for 3 times, and then the mixture was stirred at 35~40° C. for 16 hrs under N₂ atmosphere. LCMS showed that 4 was consumed completely. The reaction mixture was quenched by addition water (10 ml) at rt., and then diluted with EA (15 mL) and extracted with EA (15 mL×3). The combined organic layers were washed with brine (20 mL×2), filtered and concentrated under reduced pressure to give a residue.

The residue was purified by prep-HPLC to give the desired product Compound 15 (15.0, yield: 12%).

LCMS: m/z, 333.1 (M+H)+;

$^1$HNMR (400 MHz, CDCl$_3$): δ 7.55 (t, J=15.6 Hz, 1H), 7.04 (d, J=7.2 Hz, 2H), 6.73 (t, J=19.6 Hz, 2H), 6.58 (s, 1H), 6.46 (d, J=11.6 Hz, 1H), 3.98 (s, 3H), 3.76 (d, J=8.8 Hz, 1H), 3.55 (m, 3H), 2.25 (m, 1H), 1.49 (t, J=13.2 Hz, 1H), 1.02 (t, J=10 Hz, 1H).

Example Compound 16

Preparation of 3-(2-fluorophenyl)-1-(pyridin-2-yl-ethynyl)-3-azabicyclo[3.1.0]hexane

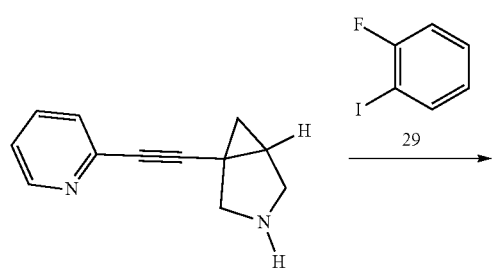

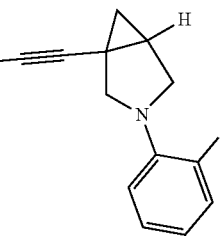

Compound 16

Experimental Section

Procedure for Preparation of Compound 16

A mixture of 6 (60.0 mg, 325 μmol), 29 (72.3 mg, 325 μmol), Cs$_2$CO$_3$ (212.0 mg, 651 μmol), Xantphos (18.8 mg, 32.5 μmol) and Pd$_2$(dba)$_3$ (29.8 mg, 32.5 μmol) in dioxane (4 mL) was degassed and purged with N$_2$ for 3 times, and then the mixture was stirred at 80° C. for 2 hrs under N$_2$ atmosphere. LCMS showed that 6 was consumed completely. The reaction mixture was quenched by addition water (5 mL) at rt., and then diluted with EA (10 mL) and extracted with EA (10 mL×3). The combined organic layers were washed with brine (20 mL×2), filtered and concentrated under reduced pressure to give a residue. The residue was purified by prep-HPLC to give the desired product Compound 16 (30 mg, yield: 33%).

LCMS: m/z, 304.1 (M+H)+;

$^1$HNMR (400 MHz, CDCl$_3$): δ 8.48 (d, J=4.8 Hz, 1H), 7.55 (m, 1H), 7.33 (d, J=8 Hz, 1H), 7.17 (m, 1H), 6.94 (m, 2H), 6.69 (m, 2H), 3.86 (m, 1H), 3.68 (m, 1H), 3.38 (m, 2H), 2.01 (m, 1H), 1.20 (t, J=7.6 Hz, 2H).

Example Compound 17

Preparation of 3-(2-chlorophenyl)-1-(pyridin-2-yl-ethynyl)-3-azabicyclo[3.1.0]hexane

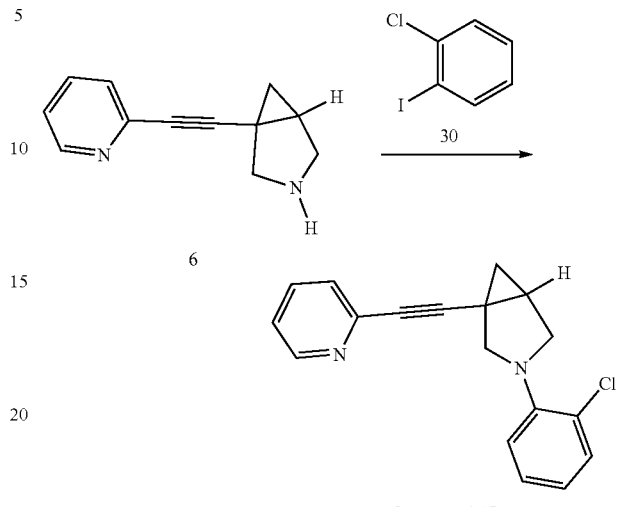

Compound 17

Experimental Section

Procedure for Preparation of Compound 17

A mixture of compound 6 (100 mg, 542 μmol), 30 (129 mg, 542 μmol), Cs$_2$CO$_3$ (353 mg, 1.09 mmol), Xantphos (31.4 mg, 54.2 μmol) and Pd$_2$(dba)$_3$ (49.7 mg, 54.2 μmol) in dioxane (1 mL) was degassed and purged with N$_2$ for 3 times, and then the mixture was stirred at 80° C. for 16 hrs under N$_2$ atmosphere. LCMS showed that 6 was consumed completely. The reaction mixture was quenched by addition water (15 mL) at rt., and then diluted with EA (30 mL) and extracted with EA (20 mL×3). The combined organic layers were washed with brine (30 mL×2), filtered and concentrated under reduced pressure to give a residue. The residue was purified by prep-HPLC to give the desired product Compound 17 (33 mg, yield: 20%).

LCMS: m/z, 278.1 (M+H)+;

$^1$HNMR (400 MHz, CDCl$_3$): δ 8.55 (d, J=4 Hz, 1H), 7.63 (m, 1H), 7.39 (d, J=8 Hz, 1H), 7.31 (m, 1H), 7.20 (m, 2H), 6.96 (m, 2H), 3.90 (d, J=8.8 Hz, 1H), 3.76 (d, J=9.2 Hz, 1H), 3.33 (m, 2H), 2.03 (m, 1H), 1.50 (t, J=9.2 Hz, 1H), 1.20 (m, 1H).

Example Compound 18

Preparation of 3-(3-chlorophenyl)-1-(pyridin-2-yl-ethynyl)-3-azabicyclo[3.1.0]hexane

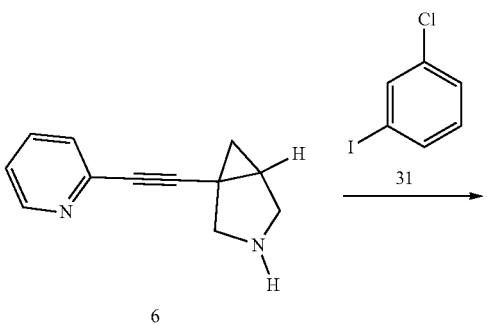

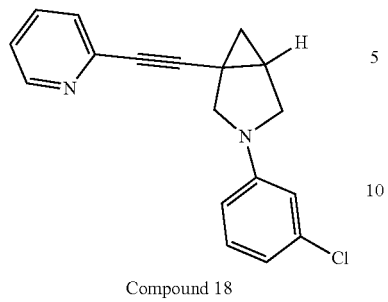

Compound 18

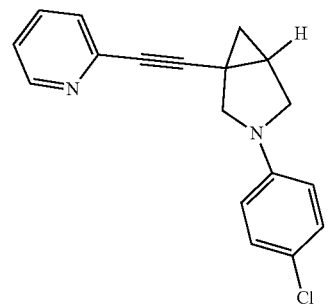

Compound 19

Experimental Section

Procedure for Preparation of Compound 18

A mixture of compound 6 (80 mg, 434 μmol), 31 (103 mg, 434 μmol), Cs$_2$CO$_3$ (282 mg, 868 μmol), Xantphos (24.1 mg, 43.4 μmol) and Pd$_2$(dba)$_3$ (39.7 mg, 43.4 μmol) in dioxane (4 mL) was degassed and purged with N$_2$ for 3 times, and then the mixture was stirred at 80° C. for 16 hrs under N$_2$ atmosphere. LCMS showed that 6 was consumed completely. The reaction mixture was quenched by addition water (10 mL) at rt., and then diluted with EA (10 mL) and extracted with EA (15 mL×3). The combined organic layers were washed with brine (20 mL×2), filtered and concentrated under reduced pressure to give a residue. The residue was purified by prep-HPLC to give the desired product Compound 18 (34 mg, yield: 26%).

LCMS: m/z, 294.1 (M+H)$^+$;

$^1$H NMR (400 MHz CDCl3): δ 8.48 (d, J=4.4 Hz, 1H), 7.58 (m, 1H), 7.33 (d, J=7.6 Hz, 1H), 7.15 (m, 1H), 7.06 (t, J=16 Hz, 1H), 6.62 (d, J=8 Hz, 1H), 6.46 (s, 1H), 6.37 (m, 1H), 3.70 (d, J=8.8 Hz, 1H), 3.48 (d, J=9.2 Hz, 1H), 3.38 (m, 2H), 2.10 (m, 1H), 1.32 (m, 1H), 0.97 (t, J=9.6 Hz, 1H).

Example Compound 19

Preparation of 3-(4-chlorophenyl)-1-(pyridin-2-yl-ethynyl)-3-azabicyclo[3.1.0]hexane Experimental Section Procedure for Preparation of Compound 19

A mixture of 6 (100 mg, 542 μmol), 32 (129 mg, 542 μmol), Cs$_2$CO$_3$ (353 mg, 1.09 mmol), Xantphos (31.4 mg, 54.2 mol) and Pd$_2$(dba)$_3$ (49.7 mg, 54.2 μmol) in dioxane (4 mL) was degassed and purged with N$_2$ for 3 times, and then the mixture was stirred at 80° C. for 16 hrs under N$_2$ atmosphere. LCMS showed that 6 was consumed completely. The reaction mixture was quenched by addition water (15 mL) at rt., and then diluted with EA (15 mL) and extracted with EA (20 mL×3). The combined organic layers were washed with brine (30 mL×2), filtered and concentrated under reduced pressure to give a residue. The residue was purified by prep-HPLC to give the desired product Compound 19 (43 mg, yield: 26%).

LCMS: m/z, 294.1 (M+H)$^+$;

$^1$H NMR (400 MHz CDCl$_3$): δ 8.58 (d, J=4.4 Hz, 1H), 7.67 (m, 1H), 7.42 (d, J=8 Hz, 1H), 7.24 (m, 3H), 6.51 (d, J=9.2 Hz, 2H), 3.79 (d, J=8.8 Hz, 1H), 3.58 (d, J=8.8 Hz, 1H), 3.44 (m, 2H), 2.19 (m, 1H), 1.40 (m, 1H), 1.10 (t, J=9.2 Hz, 1H).

Example Compound 20

Preparation of 3-(3-chloro-5-fluorophenyl)-1-(pyridin-2-ylethynyl)-3-azabicyclo[3.1.0]hexane

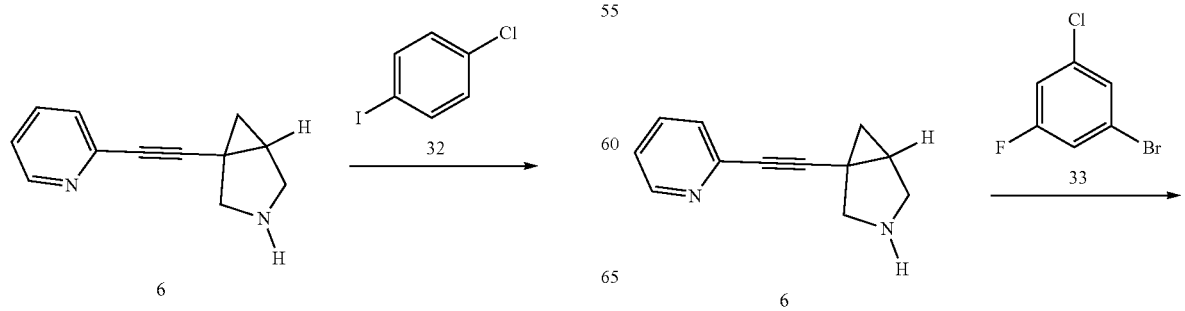

-continued

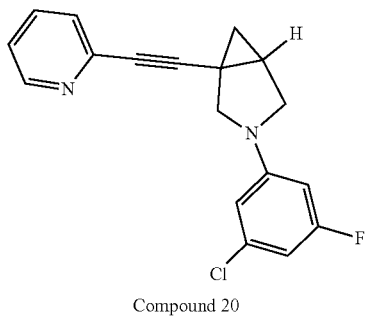

Compound 20

Experimental Section

Procedure for Preparation of Compound 20

A mixture of 6 (100 mg, 542 μmol), 33 (113 mg, 542 μmol), Cs$_2$CO$_3$ (353 mg, 1.09 mmol), Xantphos (31.4 mg, 54.2 μmol) and Pd$_2$(dba)$_3$ (49.7 mg, 54.2 μmol) in dioxane (4 mL) was degassed and purged with N$_2$ for 3 times, and then the mixture was stirred at 80° C. for 16 hrs under N$_2$ atmosphere. LCMS showed that 6 was consumed completely. The reaction mixture was quenched by addition water (5 mL) at rt., and then diluted with EA (10 mL) and extracted with EA (10 mL×3). The combined organic layers were washed with brine (20 mL×2), filtered and concentrated under reduced pressure to give a residue. The residue was purified by prep-HPLC to give the desired product Compound 20 (35 mg, yield: 20%).

LCMS: m/z, 294.1 (M+H)$^+$;

$^1$H NMR (400 MHz CDCl$_3$): δ 8.58 (d, J=4.4 Hz, 1H), 7.68 (m, 1H), 7.42 (d, J=8 Hz, 1H), 7.25 (m, 1H), 6.46 (d, J=9.2 Hz, 1H), 6.33 (s, 1H), 6.17 (d, J=11.6 Hz, 1H), 3.75 (d, J=9.2 Hz, 1H), 3.53 (m, 3H), 2.20 (m, 1H), 1.44 (m, 1H), 1.03 (t, J=9.6 Hz, 1H).

Example Compound 21

Preparation of 3-(4-chloro-2-fluorophenyl)-1-(pyridin-2-ylethynyl)-3-azabicyclo[3.1.0]hexane

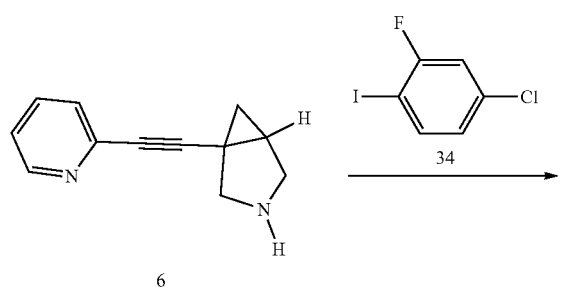

-continued

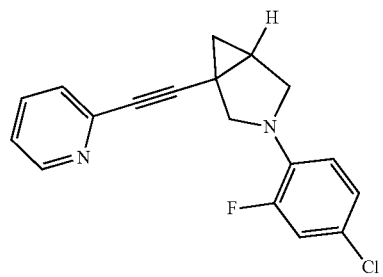

Compound 21

Experimental Section

Procedure for Preparation of Compound 21

A mixture of 6 (100 mg, 542 μmol), 34 (139 mg, 542 μmol), Cs$_2$CO$_3$ (353 mg, 1.09 mmol), Xantphos (31.4 mg, 54.2 μmol) and Pd$_2$(dba)$_3$ (49.7 mg, 54.2 μmol) in dioxane (4 mL) was degassed and purged with N$_2$ for 3 times, and then the mixture was stirred at 80° C. for 16 hrs under N$_2$ atmosphere. LCMS showed that 6 was consumed completely. The reaction mixture was quenched by addition water (15 mL) at rt., and then diluted with EA (15 mL) and extracted with EA (20 mL×3). The combined organic layers were washed with brine (20 mL×2), filtered and concentrated under reduced pressure to give a residue. The residue was purified by prep-HPLC to give the desired product Compound 21 (43 mg, yield: 25%).

LCMS: m/z, 312.1 (M+H)$^+$;

$^1$H NMR (400 MHz CDCl$_3$): δ 8.58 (d, J=4 Hz, 1H), 7.67 (t, J=14 Hz, 1H), 7.42 (d, J=7.6 Hz, 1H), 7.24 (t, J=12 Hz, 1H), 7.03 (m, 1H), 6.63 (d, J=8.8 Hz, 1H), 3.91 (m, 1H), 3.73 (d, J=7.2 Hz, 1H), 3.45 (m, 2H), 2.11 (m, 3H), 1.32 (m, 2H).

Example Compound 22

Preparation of 3-(4-chloro-3-fluorophenyl)-1-(pyridin-2-ylethynyl)-3-azabicyclo[3.1.0]hexane

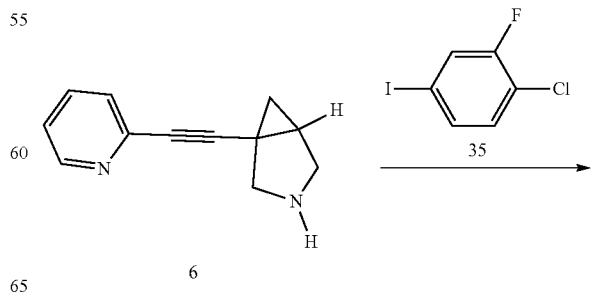

47

-continued

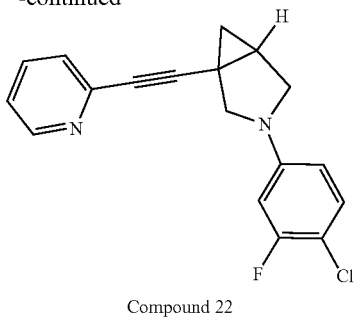

Compound 22

Experimental Section

Procedure for Preparation of Compound 22

A mixture of 6 (100 mg, 542 μmol), 35 (139 mg, 542 μmol), Cs$_2$CO$_3$ (353 mg, 1.09 mmol), Xantphos (31.4 mg, 54.2 μmol) and Pd$_2$(dba)$_3$ (49.7 mg, 54.2 μmol) in dioxane (4 mL) was degassed and purged with N$_2$ for 3 times, and then the mixture was stirred at 80° C. for 16 hrs under N$_2$ atmosphere. LCMS showed that 6 was consumed completely. The reaction mixture was quenched by addition water (15 mL) at rt., and then diluted with EA (15 mL) and extracted with EA (20 mL×3). The combined organic layers were washed with brine (20 mL×2), filtered and concentrated under reduced pressure to give a residue. The residue was purified by prep-HPLC to give the desired product Compound 22 (30 mg, yield: 17%).

LCMS: m/z, 312.1 (M+H)$^+$;

$^1$H NMR (400 MHz CDCl3): δ 8.58 (d, J=4.4 Hz, 1H), 7.67 (t, J=14 Hz, 1H), 7.42 (d, J=8 Hz, 1H), 7.25 (m, 2H), 6.36 (m, 2H), 3.75 (d, J=8.8 Hz, 1H), 3.54 (d, J=9.2 Hz, 1H), 3.46 (m, 2H), 2.20 (m, 1H), 1.43 (m, 2H), 1.07 (t, J=9.2 Hz, 1H).

Example Compound 23

Preparation of 2-(1-(pyridin-2-ylethynyl)-3-azabicyclo[3.1.0]hexan-3-yl)isonicotinonitrile

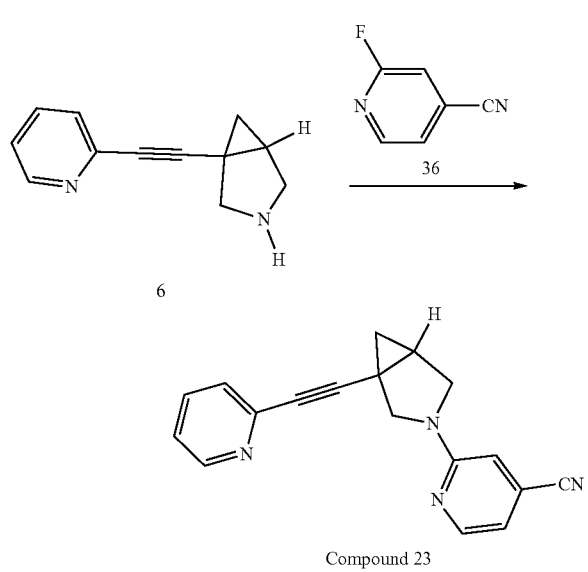

48

Experimental Section

Procedure for Preparation of Compound 23

To a solution of compound 6 (99 mg, 0.54 mmol) and 36 (99 mg, 81 mmol) in DMF (2 mL) was added K$_2$CO$_3$ (0.15 g, 1.09 mmol) and the mixture was stirred at 110° C. for 16 hrs. After the DMF evaporated under vacuo, the residue was diluted with EA (5 mL), then washed with water, the organic layer was purified by prep-HPLC to give the desired product Compound 23 (100 mg, yield: 64%).

LCMS: m/z, 286.1 (M+H)$^+$;

$^1$H NMR (400 MHz CDCl3): δ 8.58 (d, J=4 Hz, 1H), 8.28 (d, J=5.2 Hz, 1H), 7.67 (m, 1H), 7.43 (d, J=7.6 Hz, 1H), 7.25 (t, J=12.4 Hz, 1H), 6.77 (d, J=4.8 Hz, 1H), 6.54 (s, 1H), 4.00 (d, J=10.4 Hz, 1H), 3.80 (d, J=10 Hz, 1H), 3.68 (m, 2H), 2.23 (m, 1H), 1.48 (m, 2H), 0.98 (t, J=10 Hz, 1H).

Example Compound 24

Preparation of 5-(1-(pyridin-2-ylethynyl)-3-azabicyclo[3.1.0]hexan-3-yl)-1H-pyrrolo[3,2-b]pyridine

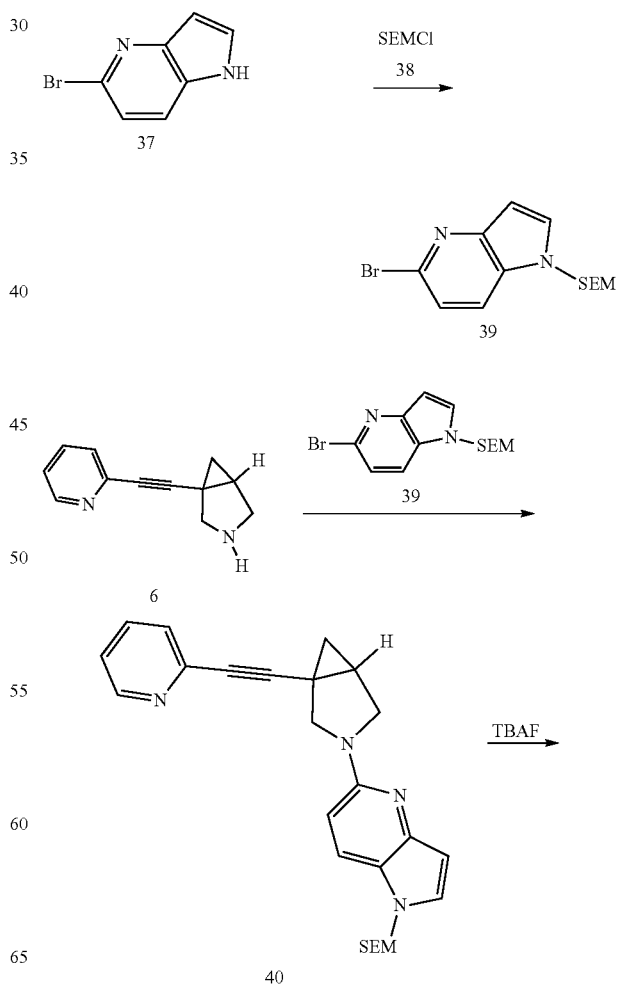

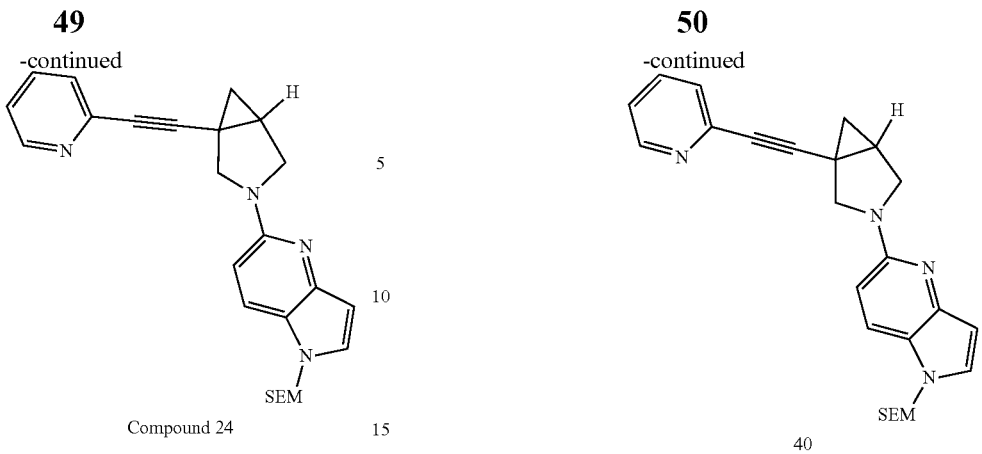

Compound 24

Experimental Section

Procedure for Preparation of Compound 39

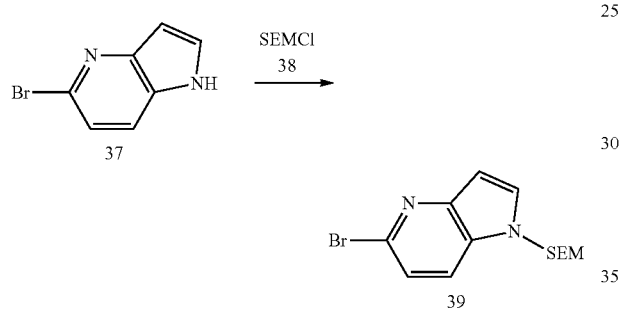

To a solution of 37 (300 mg, 1.52 mmol) in THF (10 mL) was added NaH (109 mg, 4.56 mmol) at 0° C. The mixture was stirred at 0° C. for 0.5 h, then 38 (380 mg, 2.28 mmol) was added, the mixture was stirred at 0~25° C. for 4 hrs. LCMS showed 37 was consumed completely and one main peak with desired MS was detected. The reaction mixture was quenched by addition water (15 mL), and then diluted with EA (30 mL) and extracted with EA (20 mL×2). The combined organic layers were filtered and concentrated under reduced pressure to give a residue. The residue was purified by silica column chromatography to give product 37 (380 mg, yield: 76%).

Procedure for Preparation of 40

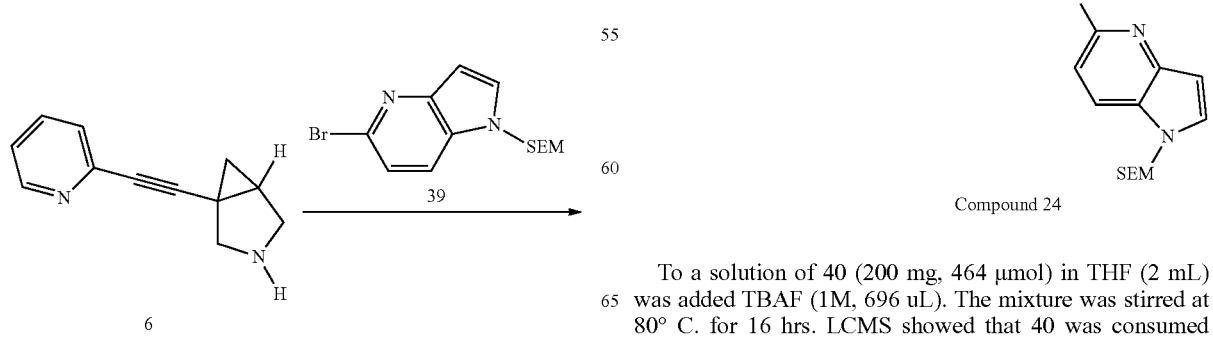

A mixture of 6 (150 mg, 814 μmol), 39 (266 mg, 814 μmol), $Cs_2CO_3$ (530 mg, 1.63 mmol), Xantphos (47 mg, 81 μmol,) and $Pd_2(dba)_3$ (74 mg, 81 μmol) in dioxane (3 mL) was degassed and purged with $N_2$ for 3 times, and then the mixture was stirred at 80° C. for 16 hrs under $N_2$ atmosphere. The reaction mixture was quenched by addition water (20 mL) at rt., and then diluted with EA (20 mL) and extracted with EA (30 mL×3). The combined organic layers were washed with brine (20 mL×2), filtered and concentrated under reduced pressure to give a residue. The residue was purified by silica column chromatography to give product 40 (200 mg, yield: 57%).

Procedure for Preparation of Compound 24

To a solution of 40 (200 mg, 464 μmol) in THF (2 mL) was added TBAF (1M, 696 uL). The mixture was stirred at 80° C. for 16 hrs. LCMS showed that 40 was consumed completely. The reaction mixture was quenched by addition water (15 mL) at rt., and extracted with EA (20 mL×3), filtered and concentrated under reduced pressure to give a residue. The residue was purified by prep-HPLC to give desired product Compound 24 (6.02 mg, yield: 4.3%).

LCMS: m/z, 300.1 (M+H)+;

$^1$H NMR (400 MHz, MeOD): δ 11.79 (s, 1H), 8.80 (d, J=5.6 Hz, 1H), 8.57 (t, J=8 Hz, 1H), 8.17 (m, 2H), 8.02 (t, J=7.2 Hz, 1H), 7.63 (s, 1H), 7.07 (d, J=9.2 Hz, 1H), 6.59 (s, 1H), 4.22 (d, J=9.6 Hz, 1H), 3.98 (m, 3H), 2.63 (m, 1H), 1.60 (m, 1H), 1.30 (m, 1H).

Example Compound 25

Preparation of 5-(1-(pyridin-2-ylethynyl)-3-azabicyclo[3.1.0]hexan-3-yl)-1H-benzo[d]imidazole

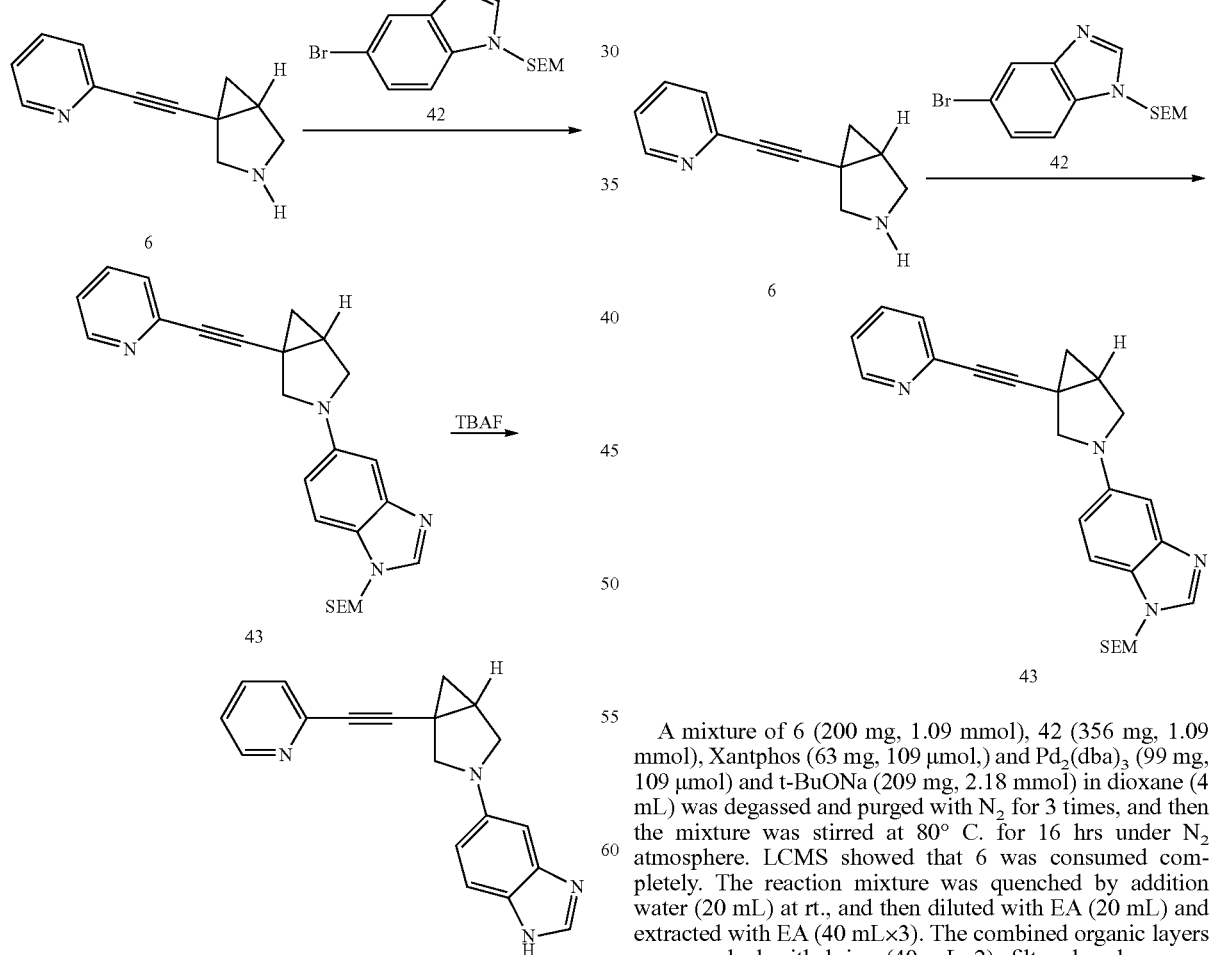

Compound 25

Experimental Section

Procedure for Preparation of 42

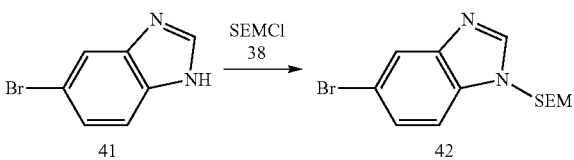

To a solution of 41 (400 mg, 2.03 mmol) in THF (10 mL) was added NaH (146 mg, 6.09 mmol) at 0° C. The mixture was stirred at 0° C. for 0.5 hr, then 38 (507 mg, 3.04 mmol) was added, the mixture was stirred at 0~25° C. for 4 hrs. LCMS showed that 41 was consumed completely and one main peak with desired MS was detected. The reaction mixture was quenched by addition water (20 mL), and then diluted with EA (30 mL) and extracted with EA (30 mL×2). The combined organic layers were filtered and concentrated under reduced pressure to give a residue. The residue was purified by silica column chromatography to give the desired product 42 (503 mg, yield: 75%).

Procedure for Preparation of 43

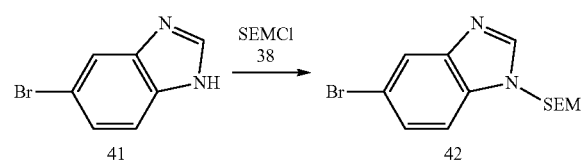 [SMILES: Brc1ccc2[nH]cnc2c1 ; C[Si](C)(C)CCOCn1cnc2cc(Br)ccc21]

A mixture of 6 (200 mg, 1.09 mmol), 42 (356 mg, 1.09 mmol), Xantphos (63 mg, 109 μmol,) and Pd$_2$(dba)$_3$ (99 mg, 109 μmol) and t-BuONa (209 mg, 2.18 mmol) in dioxane (4 mL) was degassed and purged with N$_2$ for 3 times, and then the mixture was stirred at 80° C. for 16 hrs under N$_2$ atmosphere. LCMS showed that 6 was consumed completely. The reaction mixture was quenched by addition water (20 mL) at rt., and then diluted with EA (20 mL) and extracted with EA (40 mL×3). The combined organic layers were washed with brine (40 mL×2), filtered and concentrated under reduced pressure to give a residue. The residue was purified by silica column chromatography to give product 43 (259 mg, yield: 55%).

Procedure for Preparation of Compound 25

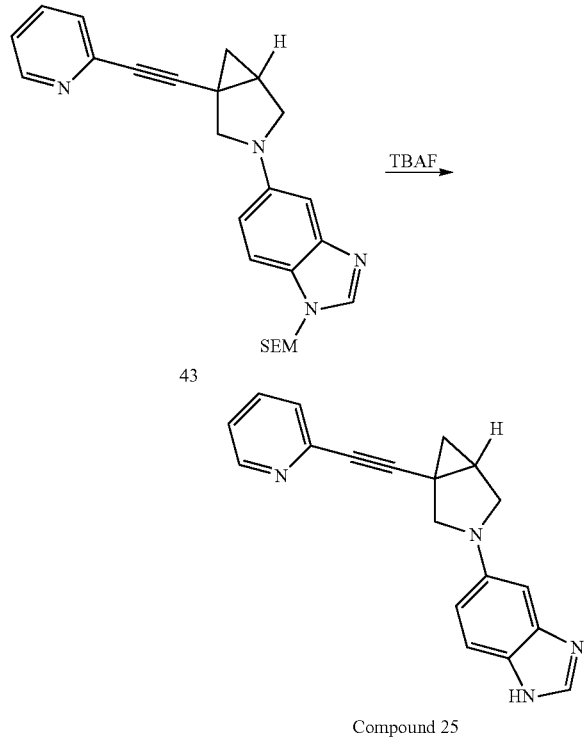

43

Compound 25

To a solution of 43 (227.00 mg, 527.15 μmol) in THF (1 mL) was added TBAF (0.15 mL, 1N TBAF/THF). The mixture was stirred at 60° C. for 3 hrs, TLC was showed that most of 43 was consumed, the reaction was quenched with water (5 mL), extracted with EA (10 mL×2), the combined organic layers were washed brine (5 mL), dried, concentrated. The residue was purified by prep-HPLC to give the desired product Compound 25 (30.00 mg, yield: 18.95%).

LCMS: m/z, 300.1 (M+H)$^+$;

$^1$H NMR (400 MHz MeOD): δ 9.12 (s, 1H), 8.78 (d, J=5.2 Hz, 1H), 8.58 (t, J=8 Hz, 1H), 8.12 (d, J=8 Hz, 1H), 8.02 (t, J=7.2 Hz, 1H), 7.66 (d, J=9.6 Hz, 1H), 7.07 (d, J=8.8 Hz, 1H), 6.87 (s, 1H), 4.01 (d, J=8.8 Hz, 1H), 3.79 (d, J=9.2 Hz, 1H), 3.56 (d, J=8.8 Hz, 1H), 3.50 (m, 1H), 2.49 (m, 1H), 1.60 (m, 1H), 1.30 (m, 1H).

Example Compound 26

Preparation of (3-chlorophenyl)(1-(pyridin-2-ylethynyl)-3-azabicyclo[3.1.0]hexan-3-yl)methanone

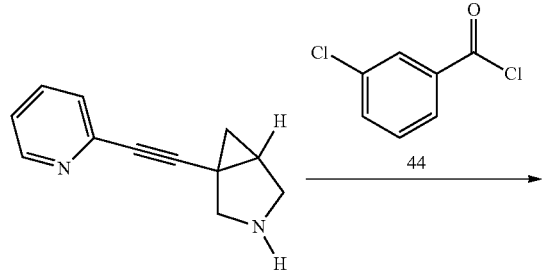

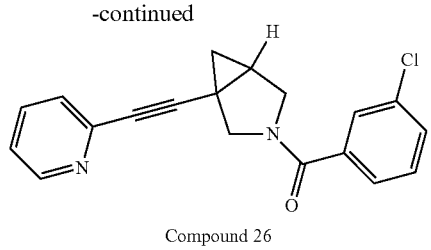

Compound 26

Experimental Section

Procedure for Preparation of Compound 26

To a solution of 6 (50.0 mg, 271 μmol) in DCM (1 mL) was added TEA (54.9 mg, 542 μmol) and 44 (49.8 mg, 284 μmol). The mixture was stirred at 0° C. for 1 hr. LCMS showed 6 was consumed completely. The reaction mixture was quenched by addition water (5 mL) at 0° C., and then extracted with DCM (10 mL×2). The combined organic layers were filtered and concentrated under reduced pressure to give a residue. The residue was purified by prep-HPLC to give the desired product Compound 26 (31.0 mg, yield: 35%).

LCMS: m/z, 322.1 (M+H)$^+$;

$^1$H NMR (400 MHz CDCl$_3$): δ 8.56 (s, 1H), 7.65 (t, J=15.6 Hz, 1H), 7.45 (m, 4H), 7.23 (d, J=5.2 Hz, 1H), 4.48 (m, 1H), 3.85 (m, 3H), 2.09 (dt, J=3.6 Hz, 1H), 1.39 (t, J=13.2 Hz, 1H), 0.85 (s, 1H).

Example Compound 27

Preparation of pyridin-2-yl(1-(pyridin-2-ylethynyl)-3-azabicyclo[3.1.0]hexan-3-yl)methanone

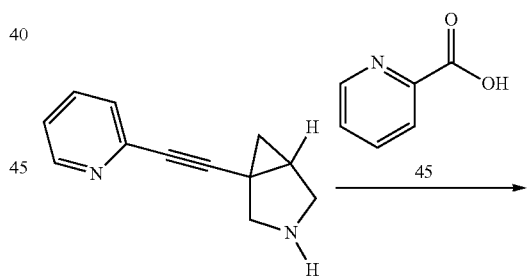

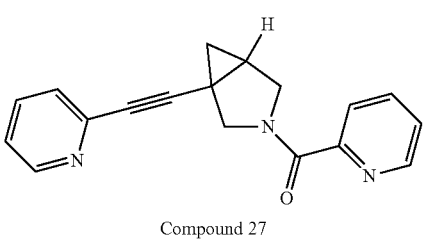

Compound 27

Experimental Section

Procedure for Preparation of Compound 27

To a solution of 6 (100 mg, 542 μmol) in DCM (1 mL) was added HATU (227 mg, 597.05 μmol), TEA (109 mg, 1.09 mmol), 45 (73.5 mg, 597 µmol) at 0° C. The mixture was stirred at 20° C. for 5 hrs. LCMS showed 6 was consumed completely. The reaction mixture was quenched by addition water (5 mL) at 20° C., and then extracted with DCM (10 mL×2). The combined organic layer concentrated under reduced pressure to give a residue. The residue was purified by prep-HPLC to give the desired product Compound 27 (59.0 mg, yield: 37%).

LCMS: m/z, 289.1 (M+H)⁺;

¹H NMR (400 MHz CDCl₃): δ 8.61 (m, 2H), 7.85 (m, 2H), 7.67 (m, 1H), 7.44 (m, 2H), 7.24 (m, 1H), 4.44 (m, 2H), 4.10 (m, 1H), 3.77 (t, J=12.8 Hz, 1H), 2.10 (m, 1H), 1.38 (m, 1H), 0.92 (m, 1H).

Example Compound 28

Preparation of phenyl(1-(pyridin-2-ylethynyl) 3-azabicyclo[3.1.0]hexan-3-yl)methanone

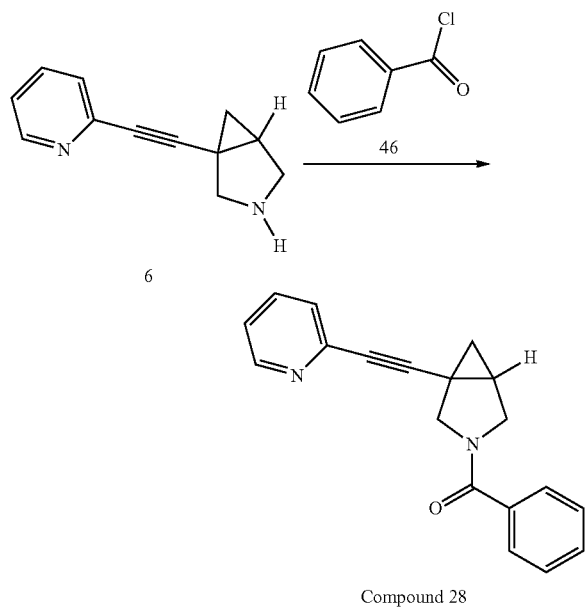

Compound 28

Experimental Section

Procedure for Preparation of Compound 28

To a solution of 6 (100 mg, 542 µmol) in DCM (2 mL) was added TEA (109 mg, 1.09 mmol), 46 (80.1 mg, 569 µmol). The mixture was stirred at 0~20° C. for 2 hrs. LCMS showed 6 was consumed completely. The reaction mixture was quenched by addition water (5 mL) at 20° C., and extracted with DCM (10 mL×2). The combined organic layers were filtered and concentrated under reduced pressure to give a residue. The residue was purified by prep-HPLC to give the desired product Compound 28 (67 mg, yield: 42%).

LCMS: m/z, 288.1 (M+H)⁺;

¹H NMR (400 MHz CDCl₃): δ 8.54 (s, 1H), 7.65 (m, 1H), 7.45 (d, J=6 Hz, 4H), 7.36 (d, J=7.6 Hz, 1H), 7.23 (d, J=4.8 Hz, 1H), 7.50 (m, 1H), 3.85 (m, 3H), 2.09 (m, 1H), 1.37 (m, 1H), 0.85 (s, 1H).

Example Compound 29

Preparation of 2-phenyl-1-(1-(pyridin-2-ylethynyl)-3-azabicyclo[3.1.0]hexan-3-yl)ethanone

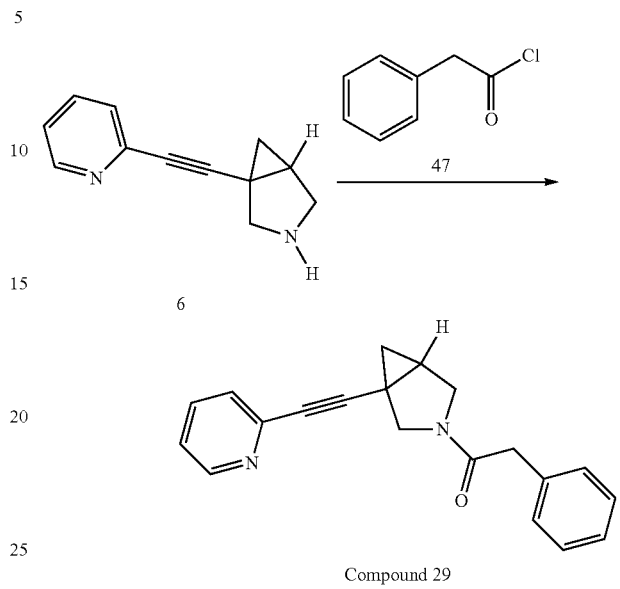

Compound 29

Experimental Section

Procedure for Preparation of Compound 29

To a solution of 6 (100 mg, 542 µmol) in DCM (2 mL), was added was added TEA (109 mg, 1.09 mmol) and 47 (92.3 mg, 597 µmol). The mixture was stirred at 0~20° C. for 2 hrs. LCMS showed 6 was consumed completely. The reaction mixture was quenched by addition water (5 mL) at 20° C., and extracted with DCM (10 mL x 2). The combined organic layers were filtered and concentrated under reduced pressure to give a residue. The residue was purified by prep-HPLC to give the desired product Compound 29 (76.0 mg, yield: 46%).

LCMS: m/z, 302.1 (M+H)⁺;

¹H NMR (400 MHz CDCl₃): δ 8.55 (d, J=2.8 Hz, 1H), 7.64 (m, 1H), 7.34 (m, 7H), 4.16 (d, J=11.6 Hz, 1H), 3.96 (m, 1H), 3.68 (m, 4H), 2.03 (m, 1H), 1.35 (m, 1H), 0.76 (m, 1H).

Example Compound 30

Preparation of (2-chlorophenyl) (1-(pyridin-2-yl-ethynyl)-3-azabicyclo[3.1.0]hexan-3-yl)methanone

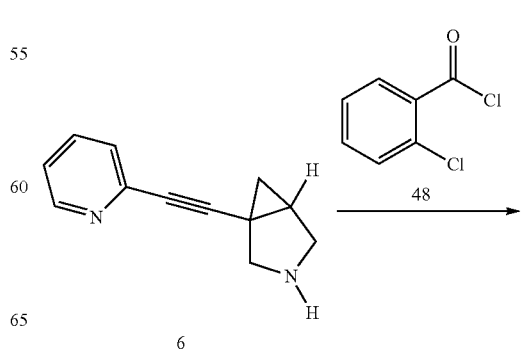

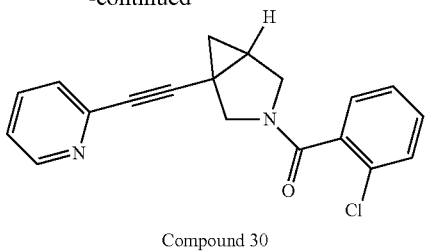

Compound 30

Experimental Section

Procedure for Preparation of Compound 30

To a solution of 6 (50.0 mg, 271 μmol) in DCM (1 mL) was added TEA (54.9 mg, 542 μmol), and 48 (47.5 mg, 271 μmol,). The mixture was stirred at 0° C. for 1 hr. LCMS showed 6 was consumed completely. The reaction mixture was quenched by addition water (5 mL) at 0° C., and then extracted with DCM (10 mL×2). The combined organic layers were filtered and concentrated under reduced pressure to give a residue. The residue was purified by prep-HPLC to give the desired product Compound 30 (35.0 mg, yield: 39%).

LCMS: m/z, 322.1 (M+H)$^+$;

$^1$H NMR (400 MHz CDCl$_3$): δ 8.56 (m, 1H), 7.66 (m, 1H), 7.42 (m, 4H), 7.34 (m, 2H), 4.41 (m, 1H), 3.72 (m, 2H), 3.46 (m, 1H), 2.13 (m, 1H), 1.41 (m, 1H), 1.00 (s, 1H).

Example Compound 31

Preparation of 1-(1-(pyridin-2-ylethynyl)-3-azabicyclo[3.1.0]hexan-3-yl)pentan-1-one

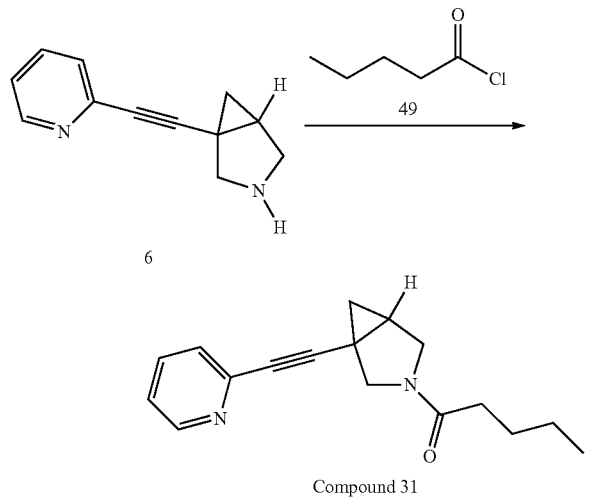

Compound 31

Experimental Section

Procedure for Preparation of Compound 31

To a solution of 6 (100 mg, 542 μmol) in DCM (2 mL) was added TEA (109 mg, 1.09 mmol), and 49 (68.7 mg, 569 μmol). The mixture was stirred at 0~20° C. for 2 hrs. LCMS showed 6 was consumed completely. The reaction mixture was quenched by addition water (5 mL) at 20° C., and extracted with DCM (10 mL×2). The combined organic layers were filtered and concentrated under reduced pressure to give a residue. The residue was purified by prep-HPLC to give the desired product Compound 31 (98 mg, yield: 67%).

LCMS: m/z, 268.1 (M+H)$^+$;

$^1$H NMR (400 MHz CDCl$_3$): δ 8.53 (t, J=8 Hz, 1H), 7.61 (m, 1H), 7.37 (t, J=14 Hz, 1H), 7.19 (m, 1H), 4.10 (d, J=12 Hz, 1H), 3.89 (d, J=12 Hz, 1H), 3.78 (d, J=10 Hz, 1H), 3.72 (m, 1H), 3.56 (m, 2H), 2.24 (m, 2H), 2.05 (m, 1H), 1.60 (m, 1H), 1.36 (m, 3H), 0.92 (m, 3H), 0.81 (t, J=10 Hz, 1H).

Example Compound 32

Preparation of 3-phenyl-1-(1-(pyridin-2-ylethynyl)-3-azabicyclo[3.1.0]hexan-3-yl)propan-1-one

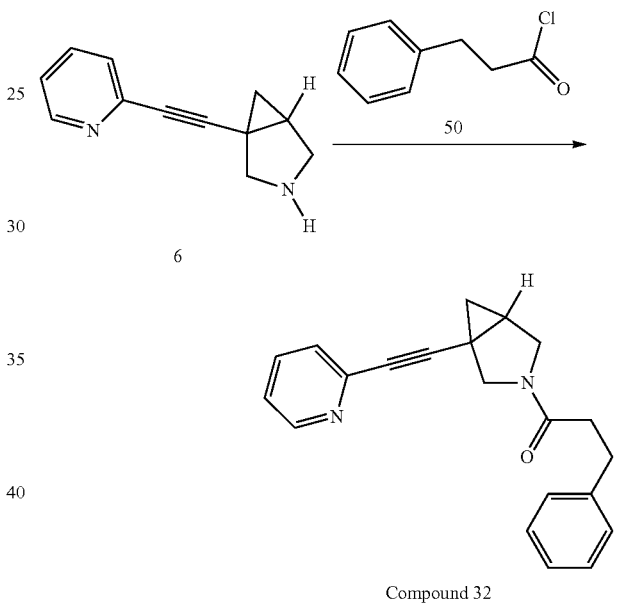

Compound 32

Experimental Section

Procedure for Preparation of Compound 32

To a solution of 6 (100 mg, 542 μmol) in DCM (2 mL), was added was added TEA (109 mg, 1.09 mmol) and 50 (91.5 mg, 542 μmol). The mixture was stirred at 0~20° C. for 2 hrs. LCMS showed 6 was consumed completely. The reaction mixture was quenched by addition water (5 mL) at 20° C., and extracted with DCM (10 mL×2). The combined organic layers were filtered and concentrated under reduced pressure to give a residue. The residue was purified by prep-HPLC to give the desired product Compound 32 (86.0 mg, yield: 50%).

LCMS: m/z, 316.1 (M+H)$^+$;

$^1$H NMR (400 MHz CDCl$_3$): δ 8.55 (d, J=4.4 Hz, 1H), 7.64 (m, 1H), 7.38 (m, 7H), 4.12 (m, 1H), 3.70 (m, 3H), 2.98 (t, J=15.6 Hz, 2H), 2.56 (m, 2H), 2.02 (m, 1H), 1.34 (m, 1H), 0.72 (m, 1H).

Example Compound 33

Preparation of (4-chlorophenyl)(1-(pyridin-2-ylethynyl)-3-azabicyclo[3.1.0]hexan-3-yl)methanone

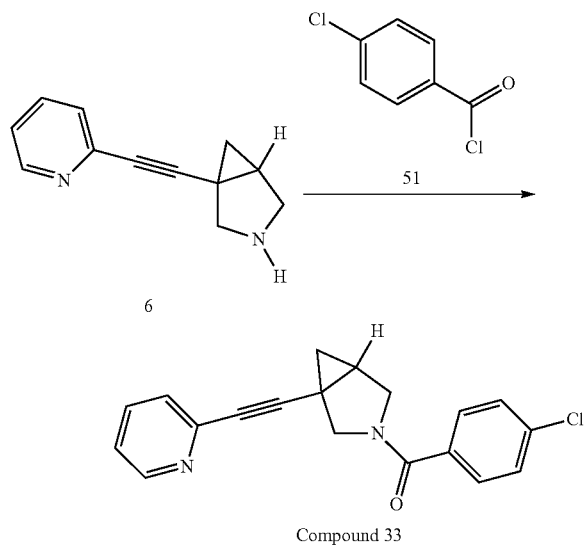

Compound 33

Experimental Section

Procedure for Preparation of Compound 33

To a solution of 6 (50.0 mg, 271 μmol) in DCM (1 mL) was added TEA (54.9 mg, 542 μmol) and 51 (47.5 mg, 271 μmol). The mixture was stirred at 0° C. for 1 hr. LCMS showed 6 was consumed completely. The reaction mixture was quenched by addition water (5 mL) at 20° C., and extracted with DCM (10 mL×2). The combined organic layers were filtered and concentrated under reduced pressure to give a residue. The residue was purified by prep-HPLC to give the desired product Compound 33 (34.0 mg, yield: 38%).

LCMS: m/z, 322.1 (M+H)$^+$;

$^1$H NMR (400 MHz CDCl$_3$): δ 8.56 (s, 1H), 7.65 (d, J=7.2 Hz, 1H), 7.41 (m, 5H), 7.23 (m, 1H), 4.49 (m, 1H), 3.86 (m, 3H), 2.09 (m, 1H), 1.38 (m, 1H), 0.85 (s, 1H).

Example Compound 34

Preparation of 3-((3-chlorophenyl)sulfonyl)-1-(pyridin-2-ylethynyl)-3-azabicyclo[3.1.0]hexane

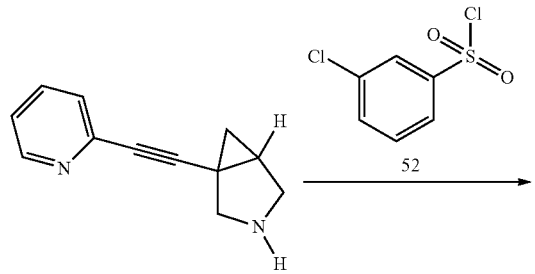

-continued

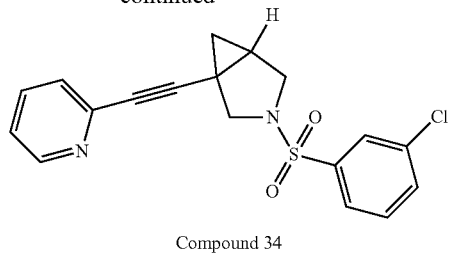

Compound 34

Experimental Section

Procedure for Preparation of Compound 34

To a solution of 6 (100 mg, 542 μmol) in DCM (2 mL) was added TEA (109 mg, 1.09 mmol), and 52 (120 mg, 569 μmol). The mixture was stirred at 0~20° C. for 1 hr. LCMS showed 6 was consumed completely. The reaction mixture was quenched by addition water (5 mL) at 20° C., and extracted with DCM (10 mL×2). The combined organic layers were filtered and concentrated under reduced pressure to give a residue. The residue was purified by prep-HPLC to give the desired product Compound 34 (93.0 mg, yield: 47%).

LCMS: m/z, 358.1 (M+H)$^+$;

$^1$H NMR (400 MHz CDCl$_3$): δ 8.55 (d, J=4.4 Hz, 1H), 7.82 (s, 1H), 7.72 (d, J=7.6 Hz, 1H), 7.70 (m, 2H), 7.53 (t, J=8 Hz, 1H), 7.35 (d, J=8 Hz, 1H), 7.22 (m, 1H), 3.81 (d, J=9.2 Hz, 1H), 3.64 (d, J=9.6 Hz, 1H), 3.23 (m, 2H), 1.98 (m, 1H), 1.30 (m, 1H), 1.17 (t, J=10.4 Hz, 1H).

Example Compound 35

Preparation of 3-((4-chlorophenyl)sulfonyl)-1-(pyridin-2-ylethynyl)-3-azabicyclo[3.1.0]hexane Compound 35

Experimental Section

Procedure for Preparation of Compound 35

To a solution of 6 (100 mg, 542 µmol) in DCM (2 mL) was added TEA (109 mg, 1.09 mmol) and 53 (120 mg, 569 µmol). The mixture was stirred at 0~20° C. for 2 hrs. LCMS showed 6 was consumed completely. The reaction mixture was quenched by addition water (5 mL) at 20° C., and extracted with DCM (10 mL×2). The combined organic layers were filtered and concentrated under reduced pressure to give a residue. The residue was purified by prep-HPLC to give the desired product Compound 35 (84.0 mg, yield: 43%).

LCMS: m/z, 358.1 (M+H)+

¹H NMR (400 MHz CDCl₃): δ 8.50 (d, J=4.4 Hz, 1H), 7.73 (d, J=8.8 Hz, 2H), 7.59 (t, J=7.6 Hz, 1H), 7.52 (d, J=8.4 Hz, 2H), 7.32 (d, J=7.6 Hz, 1H), 7.19 (t, J=6 Hz, 1H), 3.75 (d, J=9.2 Hz, 1H), 3.58 (d, J=9.6 Hz, 1H), 3.16 (m, 2H), 1.92 (m, 1H), 1.25 (m, 1H), 1.13 (t, J=10 Hz, 1H).

Example Compound 36

Preparation of 3-((2-chlorophenyl)sulfonyl)-1-(pyridin-2-ylethynyl)-3-azabicyclo[3.1.0]hexane

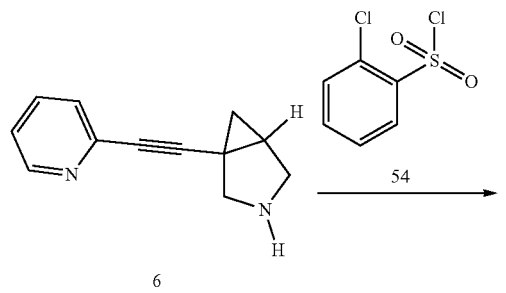

Experimental Section

Procedure for Preparation of Compound 36

To a solution of 6 (100 mg, 542 µmol) in DCM (2 mL) was added TEA (109 mg, 1.09 mmol) and 54 (120 mg, 569 µmol). The mixture was stirred at 0~20° C. for 1 hr. LCMS showed 6 was consumed completely. The reaction mixture was quenched by addition water (5 mL) at 20° C., and extracted with DCM (10 mL×2). The combined organic layers were filtered and concentrated under reduced pressure to give a residue. The residue was purified by prep-HPLC to give the desired product Compound 36 (73.0 mg, 37% yield) was obtained as a white solid.

LCMS: m/z, 358.1 (M+H)+;

¹H NMR (400 MHz CDCl₃): δ 8.55 (d, J=4.4 Hz, 1H), 8.09 (d, J=8 Hz, 1H), 7.65 (m, 1H), 7.55 (m, 2H), 7.43 (m, 2H), 7.22 (m, 1H), 3.85 (d, J=9.6 Hz, 1H), 3.71 (d, J=10 Hz, 1H), 3.58 (m, 2H), 2.02 (m, 1H), 1.32 (m, 1H), 1.15 (t, J=10 Hz, 1H).

Example Compound 37

Preparation of 1-(pyridin-2-ylethynyl)-3-tosyl-3-azabicyclo[3.1.0]hexane

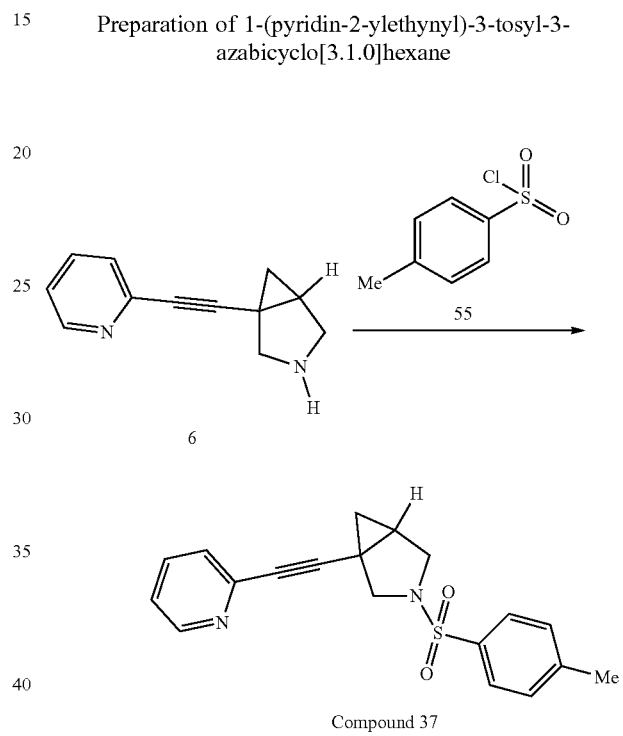

Experimental Section

Procedure for Preparation of Compound 37

To a solution of 6 (100 mg, 542 µmol) in DCM (2 mL) was added TEA (109 mg, 1.09 mmol) and 55 (108 mg, 569 µmol). The mixture was stirred at 0~20° C. for 1 hr. LCMS showed 6 was consumed completely. The reaction mixture was quenched by addition water (5 mL) at 20° C., and extracted with DCM (10 mL×2). The combined organic layers were filtered and concentrated under reduced pressure to give a residue. The residue was purified by prep-HPLC to give the desired product Compound 37 (68.0 mg, yield: 37%).

LCMS: m/z, 338.1 (M+H)+;

¹H NMR (400 MHz CDCl₃): δ 8.54 (d, J=4.4 Hz, 1H), 7.71 (m, 3H), 7.38 (t, J=17.2 Hz, 3H), 7.22 (t, J=5.2 Hz, 1H), 3.77 (d, J=9.2 Hz, 1H), 3.61 (d, J=9.2 Hz, 1H), 3.18 (m, 2H), 2.47 (s, 3H), 1.93 (m, 1H), 1.27 (m, 2H).

Example Compound 38

Preparation of 6-(1-(pyridin-2-ylethynyl)-3-azabicyclo[3.1.0]hexan-3-yl)picolinonitrile

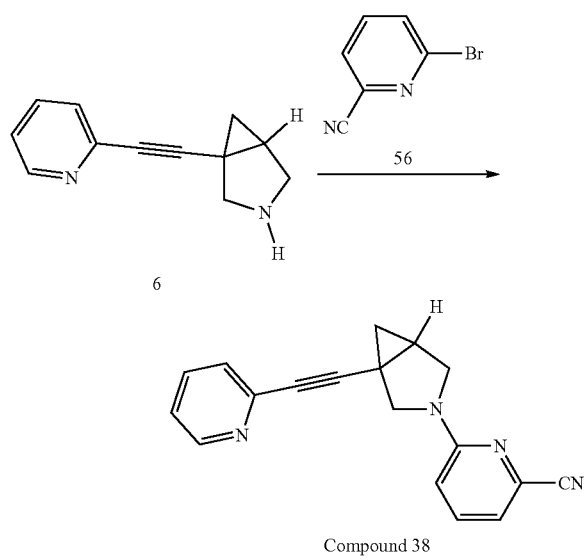

Experimental Section

Procedure for Preparation of Compound 38

A mixture of compound 6 (100 mg, 542 μmol), 54 (109 mg, 597 μmol), $Cs_2CO_3$ (353 mg, 1.09 mmol), Xantphos (31.4 mg, 54.2 μmol) and $Pd_2(dba)_3$ (49.7 mg, 54.2 μmol) in dioxane (5 mL) was degassed and purged with $N_2$ for 3 times, and then the mixture was stirred at 80° C. for 16 hrs under $N_2$ atmosphere. LCMS showed 10% of reactant 6 was remained. The reaction mixture was quenched by addition $H_2O$ (5 mL) at rt., and then diluted with EA (10 mL) and extracted with EA (15 mL×3). The combined organic layers were washed with brine (20 mL×2), filtered and concentrated under reduced pressure to give a residue. The residue was purified by prep-HPLC to give the desired product Compound 38 (9.00 mg, yield: 5%).

LCMS: m/z, 286.1 (M+H)+;

1H NMR (400 MHz CDCl3): δ 8.56 (d, J=4.8 Hz, 1H), 7.64 (t, J=7.6 Hz, 1H), 7.51 (t, J=7.6 Hz, 1H), 7.41 (d, J=8 Hz, 1H), 7.23 (m, 1H), 6.98 (d, J=7.2 Hz, 1H), 6.54 (d, J=8.8 Hz, 1H), 3.98 (d, J=10 Hz, 1H), 3.82 (d, J=10.4 Hz, 1H), 3.65 (m, 2H), 2.20 (m, 1H), 1.45 (m, 1H), 0.96 (t, J=6 Hz, 1H).

Example Compound 39

Preparation of 3-fluoro-5-(1-((2-methylthiazol-4-yl)ethynyl)-3-azabicyclo[3.1.0]hexan-3-yl)benzonitrile

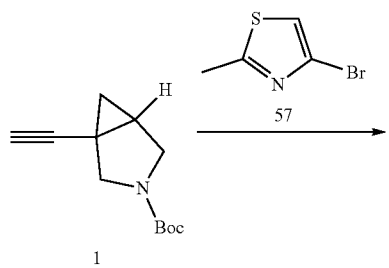

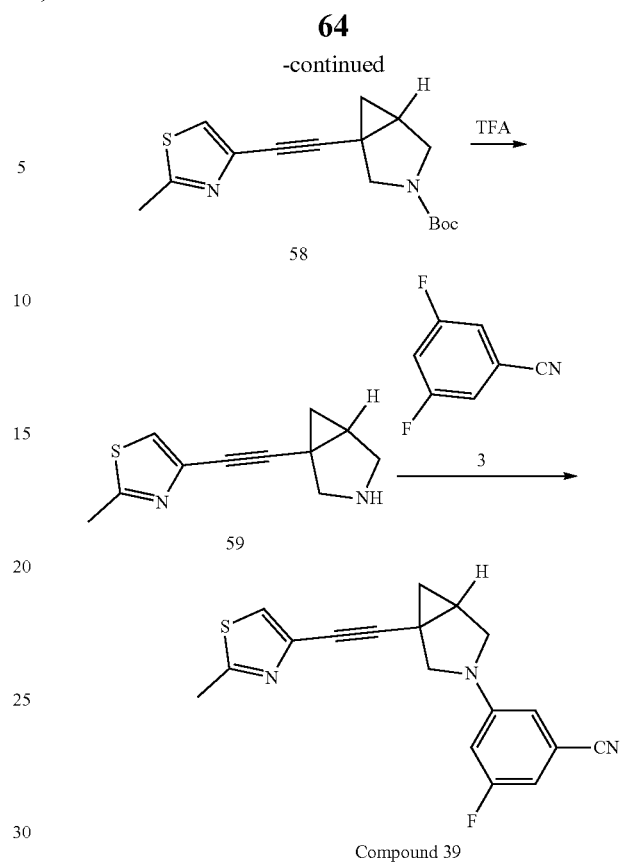

Experimental Section

Procedure for Preparation of 58

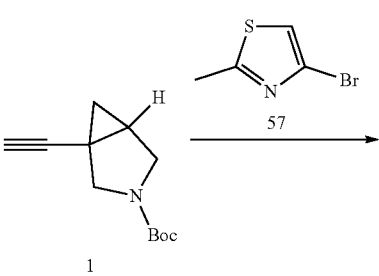

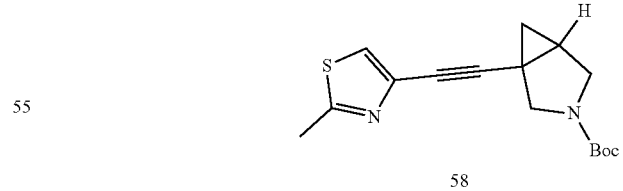

A mixture of 1 (1.00 g, 4.82 mmol), 57 (944 mg, 5.30 mmol), CuI (91.8 mg, 482 μmol), $PPh_3$ (126 mg, 482 μmol) and $Pd(PPh_3)_2Cl_2$ (169 mg, 241 μmol) in THF (10 mL) and TEA (10 mL) was degassed and purged with $N_2$ for 3 times, and then the mixture was stirred at 35~40° C. for 16 hrs under $N_2$ atmosphere. LCMS and TLC showed reactant 1 was consumed completely. The reaction mixture was concentrated under vacuo at 40° C. The residue was purified by silica column chromatography to give product 58 (921 mg, yield: 62%).

Procedure for Preparation of 59

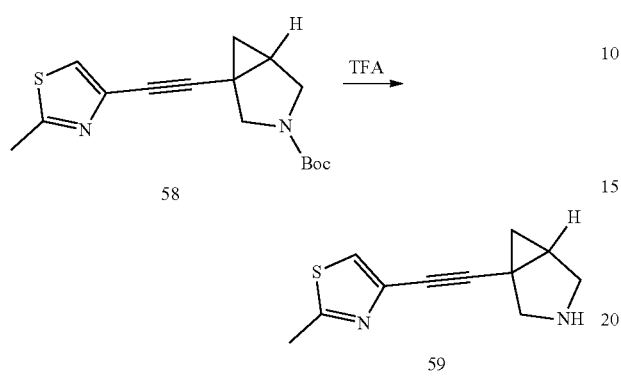

To a solution of 58 (500 mg, 1.64 mmol) in DCM (10 mL) was added TFA (7.65 mg, 67.0 mmol). The mixture was stirred at 20° C. for 1 hr. LCMS showed reactant 58 was consumed completely. The reaction mixture was concentrated under reduced pressure to remove solvent. The residue was dissolved in MeOH (50 mL) then the pH debugging to 8-9 by basic resin, filtered and concentrated under reduced pressure to give a residue to give product 59 (302 mg, crude), which was used for the next step without purification.

LCMS: m/z, 205.2 (M+H)$^+$;

Procedure for Preparation of Compound 39

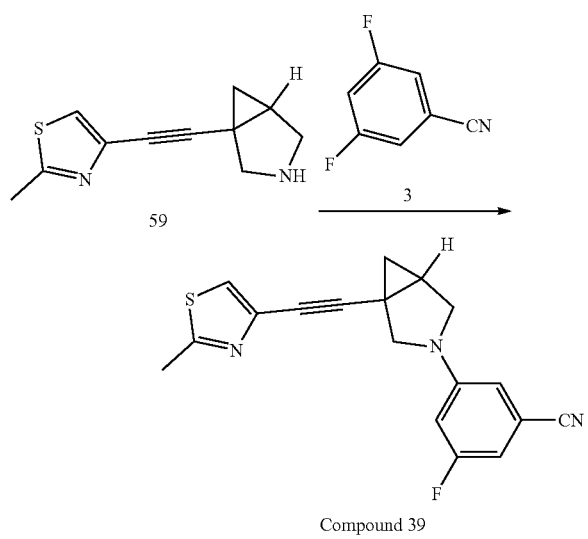

To a solution of 59 (150 mg, 734 µmol) in DMF (1 mL) was added K$_2$CO$_3$ (202 mg, 1.47 mmol) and 3 (112 mg, 807 µmol). The mixture was stirred at 110° C. for 16 hrs. LCMS showed 28% of reactant 59 was remained. The reaction mixture was quenched by addition water (10 mL) at 20° C., and extracted with EA (20 mL×2). The combined organic layers were filtered and concentrated under reduced pressure to give a residue. The residue was purified by prep-HPLC to give the desired product Compound 39 (73.0 mg, yield: 30%).

LCMS: m/z, 323.1 (M+H)$^+$;

$^1$H NMR (400 MHz CDCl$_3$): δ 7.28 (d, J=6.4 Hz, 1H), 6.69 (d, J=7.6 Hz, 1H), 6.56 (s, 1H), 6.45 (m, 1H), 3.73 (d, J=9.2 Hz, 1H), 3.54 (m, 3H), 2.72 (s, 3H), 2.20 (m, 1H), 1.43 (m, 1H), 0.99 (t, J=9.6 Hz, 1H).

Example Compound 40

Preparation of 3-(1-(pyridin-2-ylethynyl)-3-azabicyclo[3.1.0]hexan-3-yl)benzonitrile

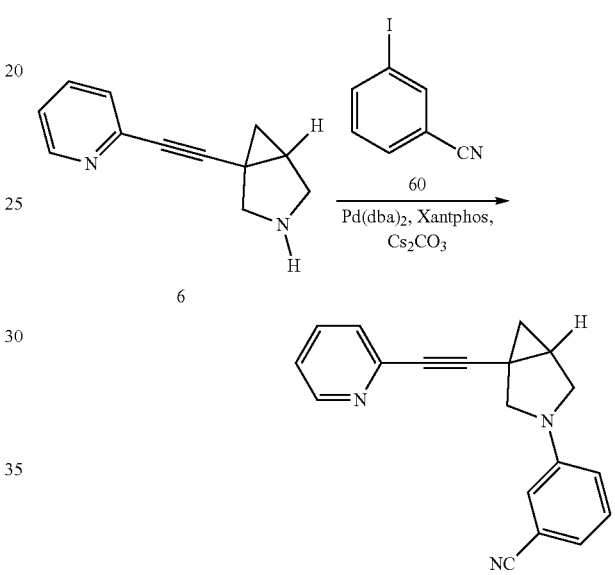

Experimental Section

Procedure for Preparation of Compound 40

To a mixture of 6 (300 mg, 1.63 mmol) in anhydrous dioxane (10.00 mL) was added Cs$_2$CO$_3$ (1.59 g, 4.89 mmol), Xtanphos (94.32 mg, 163.00 µmol), 60 (373.30 mg, 1.63 mmol) and Pd$_2$(dba)$_3$ (149.26 mg, 163.00 µmol) at 5-10° C. The mixture was degassed and purged with N$_2$ for 3 times, and then the mixture was stirred at 80° C. for 16 hr. LCMS showed the starting material was consumed completely and the desired product was detected. TLC showed the starting material was consumed completely. The mixture was cooled to 15° C. and concentrated to remove dioxane. The mixture was dissolved in EtOAc (50 mL) and H$_2$O (50 mL). The aqueous layer was extracted with EtOAc (30 mL×3), the combined organic layers were washed with brine (5 mL), dried over anhydrous Na$_2$SO$_4$, filtered and concentrated under reduced pressure to give a residue. The residue was purified by column chromatography to give the crude product. The crude product was purified by prep-HPLC to give the desired product Compound 40 (44.25 mg, yield: 9%) as a yellow solid.

LCMS: m/z, 286.1 (M+H)$^+$;

$^1$H NMR (400 MHz CDCl$_3$): δ 8.55 (d, J=4.4 Hz, 1H), 7.64 (t, J=5.6 Hz, 1H), 7.49 (d, J=8.0 Hz, 1H), 7.20-7.29 (m, 2H), 6.98 (d, J=7.2 Hz, 1H), 6.73-6.67 (m, 2H), 3.77 (d, J=8.8 Hz, 1H), 3.56 (d, J=8.8 Hz, 1H), 3.47 (d, J=8.8 Hz, 1H), 3.40-3.43 (m, 1H), 2.17-2.21 (m, 1H), 1.41 (dd, J=8.0, 3.2 Hz, 1H), 1.03 (t, J=4.8 Hz, 1H).

Example Compound 41

Preparation of (3-fluorophenyl)-(1-(pyridin-2-yl-ethynyl)-3-azabicyclo[3.1.0]hexan-3-yl)methanone

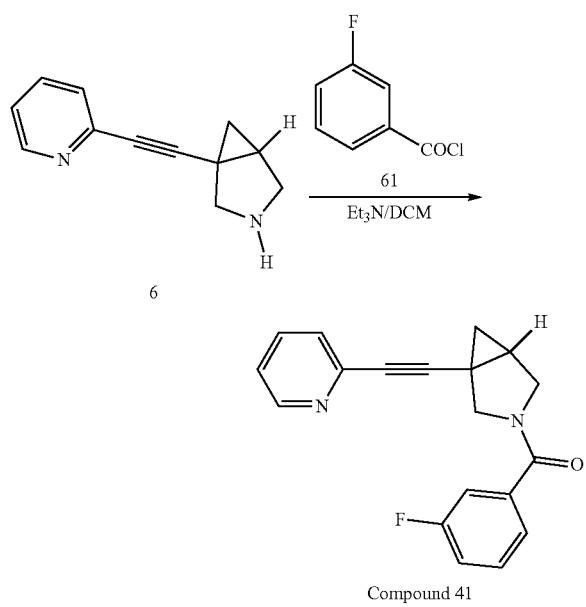

Compound 41

Experimental Section

Procedure for Preparation of Compound 41

To a solution of compound 6 (250 mg, 1.36 mmol) in DCM (1.00 mL) was added Et$_3$N (549 mg, 5.43 mmol) at 5-10° C. The mixture was stirred at 15° C. for 15 mins. Then 61 (258 mg, 1.63 mmol) was added to the above mixture at 5-10° C. The mixture was stirred at 15° C. for 2 hr. TLC showed the starting material was consumed completely. The mixture was poured into H$_2$O (5 mL) at 5-10° C. The aqueous layer was extracted with DCM (5 mL×2), the combined organic layers were washed with brine (2 mL), dried over anhydrous Na$_2$SO$_4$, filtered and concentrated under reduced pressure to give a residue. The residue was purified by prep-HPLC to give the desired product Compound 41 (25.15 mg, yield: 6%) as yellow oil.

LCMS: m/z, 307.1 (M+H)$^+$;

$^1$H NMR (400 MHz CDCl$_3$): δ 8.55 (s, 1H), 7.61-7.67 (m, 1H), 7.36-7.41 (m, 2H), 7.15-7.23 (m, 4H), 4.25-4.48 (m, 1H), 3.50-3.85 (m, 3H), 2.00-2.09 (m, 1H), 1.36 (t, J=6.4 Hz, 1H), 0.84 (br. s, 1H).

Example Compound 42

Preparation of 3-((2-fluorophenyl)sulfonyl)-1-(pyridin-2-ylethynyl)-3-azabicyclo[3.1.0]hexane

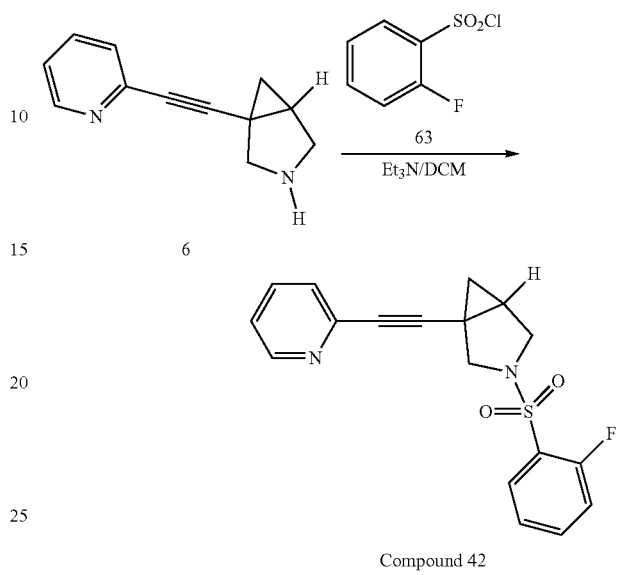

Compound 42

Experimental Section

Procedure for Preparation of Compound 42

To a solution of compound 6 (250 mg, 1.36 mmol) in DCM (1.00 mL) was added Et$_3$N (549 mg, 5.43 mmol) at 5-10° C. The mixture was stirred at 15° C. for 15 mins. Then added 63 (317 mg, 1.63 mmol) to the above mixture at 5-10° C. The mixture was stirred at 15° C. for 2 hr. TLC showed the starting material was consumed completely. The mixture was poured into H$_2$O (5 mL) at 5-10° C. The aqueous layer was extracted with DCM (5 mL×2), the combined organic layers were washed with brine (2 mL), dried over anhydrous Na$_2$SO$_4$, filtered and concentrated under reduced pressure to give a residue. The crude product was purified by prep-HPLC to give the desired product Compound 42 (28.18 mg, yield: 6%) as a yellow solid.

LCMS: m/z, 343.1 (M+H)$^+$;

$^1$H NMR (400 MHz CDCl$_3$): δ 8.51 (d, J=4.0 Hz, 1H), 7.86 (t, J=7.8 Hz, 1H), 7.59-7.61 (m, 2H), 7.20-7.35 (m, 4H), 3.81 (d, J=9.2 Hz, 1H), 3.66 (d, J=9.2 Hz, 1H), 3.39-3.42 (d, J=9.2 Hz, 2H), 1.94-2.04 (m, 1H), 1.24-1.28 (m, 1H), 1.08 (t, J=5.2 Hz, 1H).

Example Compound 43

Preparation of 3-(5-fluoropyridin-3-yl)-1-((6-methylpyridin-2-yl)ethynyl)-3-azabicyclo[3.1.0]hexane

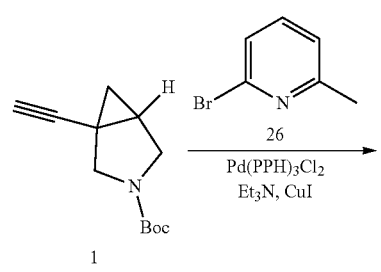

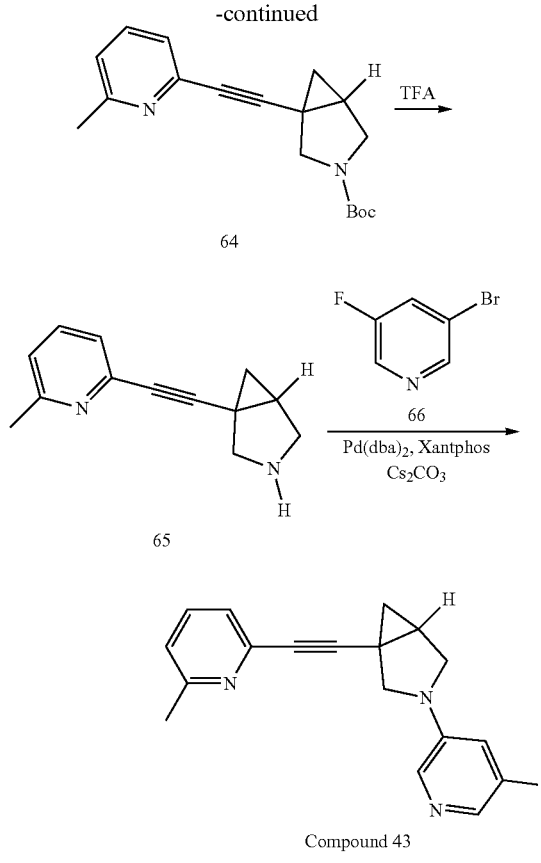

64

65

Compound 43

Experimental Section

Procedure for Preparation of 65

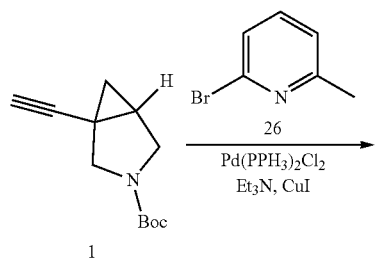

1

To a solution of compound 1 (1.00 g, 4.82 mmol) and Et₃N (6.83 g, 67.5 mmol) in THF (3 mL) was added 26 (994.96 mg, 5.78 mmol), Pd(PPh₃)₂Cl₂ (169.16 mg, 241.00 μmol), PPh₃ (126.42 mg, 482 μmol) and CuI (91.8 mg, 482 μmol) at 15° C. The mixture was bubbling with N₂ at 15° C.

The mixture was stirred at 40° C. for 16 hr. TLC showed the starting material was consumed completely and a main spot was detected. The mixture was poured into H₂O (30 mL) at 5-10° C. The aqueous layer was extracted with EtOAc (15 mL×3). The combined organic layers were washed with brine (10 mL), dried over anhydrous Na₂SO₄, filtered and concentrated under reduced pressure to give a residue. The residue was purified by column chromatography to give the desired product 64 (0.65 g, yield: 45%) as yellow oil.

¹H NMR (400 MHz CDCl3): δ 7.52 (t, J=8.0 Hz, 1H), 7.21 (t, J=6.4 Hz, 1H) 7.07 (d, J=8.0 Hz, 1H), 3.74-3.87 (m, 1H), 3.45-3.66 (m, 3H), 2.45 (s, 3H), 1.94-1.95 (m, 1H), 1.45 (s, 9H), 1.31 (dd, J=8.0, 4.8 Hz, 1H), 0.83 (t, J=4.8 Hz, 1H).

Procedure for Preparation of 66

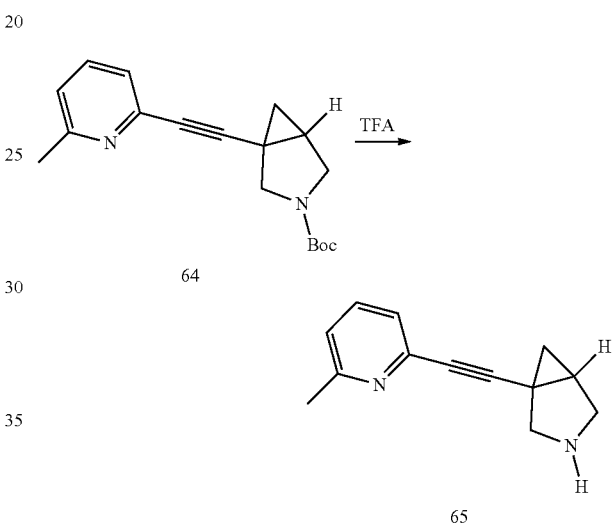

64

65

To a solution of compound 64 (650 mg, 2.18 mmol) in DCM (10 mL) was added TFA (4.47 g, 39.2 mmol) at 5-10° C. The mixture was stirred at 15° C. for 2 hr. TLC showed the starting material was consumed completely. The mixture was concentrated to give product 65 (1.20 g, crude) as yellow oil, which was used to the next step directly.

¹H NMR (400 MHz CDCl₃): δ 8.21 (t, J=8.0 Hz, 1H), 7.58-7.73 (m, 3H), 3.58-3.74 (m, 4H), 2.83 (s, 3H), 2.39 (s, 1H), 1.53-1.56 (m, 2H).

Procedure for Preparation of Compound 43

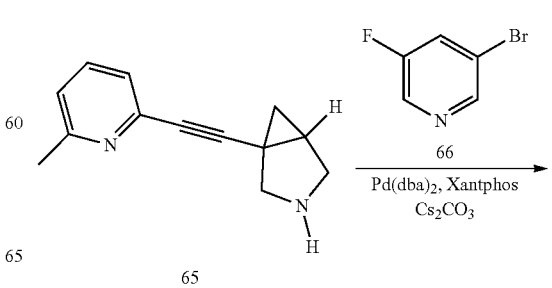

65

-continued

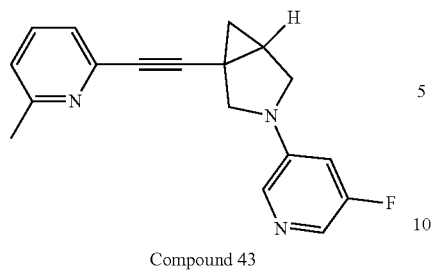

Compound 43

To a solution of compound 65 (300 mg, 1.51 mmol) in anhydrous dioxane (10.00 mL) was added Cs₂CO₃ (1.48 g, 4.53 mmol), Xtanphos (87.4 mg, 151.00 μmol), 66 (266 mg, 1.51 mmol) and Pd₂(dba)₃ (138.27 mg, 151.00 μmol) at 5-10° C. The mixture was degessed with N₂ with 3 times and the mixture was stirred at 80° C. for 16 hr. TLC showed the starting material was consumed completely and the main spot was detected. The mixture was cooled to 15° C. The mixture was poured into H₂O (50 mL) at 0-5° C. The aqueous layer ware extracted with EtOAc (25 mL×3). The combined organic layers were washed with brine (15 mL), dried over anhydrous Na₂SO₄, filtered and concentrated under reduced pressure to give a residue. The residue was purified by column chromatography to give the crude product. The crude product was purified by prep-HPLC to give the desired product Compound 43 (23.15 mg, yield: 5%) as yellow oil.

LCMS: m/z, 294.1 (M+H)⁺;

$^1$H NMR (400 MHz CDCl₃): δ 7.86 (d, J=2.0 Hz, 1H), 7.80 (s, 1H), 7.54 (t, J=8.0 Hz, 1H), 7.23 (d, J=8.0 Hz, 1H), 7.09 (d, J=8.0 Hz, 1H), 6.51-6.55 (m, 1H), 3.77 (d, J=8.8 Hz, 1H), 3.42-3.58 (m, 3H), 2.18-2.22 (m, 1H), 1.42-1.45 (m, 1H), 1.02 (t, J=4.8 Hz, 1H).

Example Compound 44

Preparation of (3-fluorophenyl)-(1-((6-methylpyridin-2-yl)ethynyl)-3-azabicyclo[3.1.0]hexan-3-yl)methanone -continued

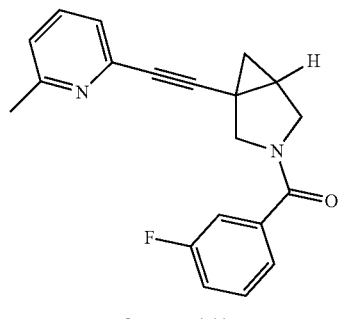

Compound 44

Experimental Section

Procedure for Preparation of Compound 44

To a solution of compound 65 (250 mg, 1.26 mmol) in DCM (2.00 mL) was added Et₃N (1.28 g, 12.6 mmol) at 5-10° C. The mixture was stirred at 15° C. for 15 mins. 67 (240 mg, 1.51 mmol) was added to the above mixture at 5-10° C. The mixture was stirred at 15° C. for 2 hr. TLC showed the starting material was consumed completely. The mixture was poured into ice-water (5 mL), the aqueous layer was extracted with DCM (5 mL×2), the combined organic layers were washed with brine (2 mL), dried over anhydrous Na₂SO₄, filtered and concentrated under reduced pressure to give a residue. The residue was purified by prep-HPLC to give the desired product Compound 44 (42.15 mg, yield: 10%) as yellow oil.

LCMS: m/z, 321.1 (M+H)⁺;

$^1$H NMR (400 MHz CDCl₃): δ 7.48-7.51 (m, 1H), 7.35-7.46 (m, 1H), 7.06-7.23 (m, 5H), 4.21-4.44 (m, 1H), 3.46-3.82 (m, 3H), 2.51 (d, J=7.2 Hz, 3H), 1.96-2.08 (m, 1H), 1.31-1.35 (m, 1H), 0.79 (t, J=4.8 Hz, 1H 1H).

Example Compound 45

Preparation of 3-(3,5-difluorophenyl)-1-(pyrimidin-2-ylethynyl)-3-azabicyclo[3.1.0]hexane

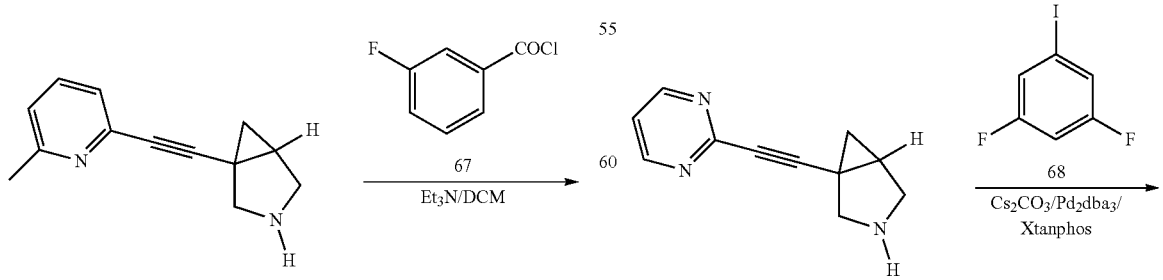

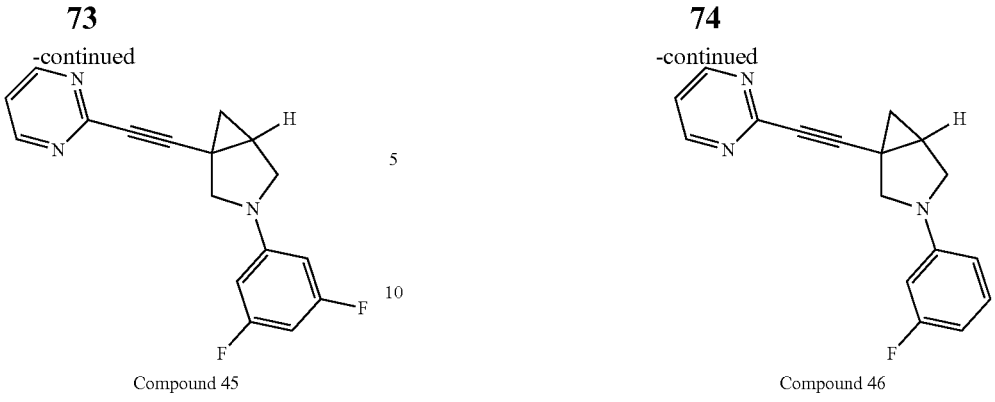

Compound 45

Compound 46

Experimental Section

Procedure for Preparation of Compound 45

To a solution of 17 (300 mg, 1.62 mmol) in anhydrous dioxane (10 mL) was added Cs$_2$CO$_3$ (1.58 g, 4.86 mmol), compound 72 (389 mg, 1.62 mmol), Xtanphos (93.7 mg, 162 μmol) and Pd$_2$(dba)$_3$ (148 mg, 162 μmol) at 5-15° C. The mixture was degessed with N$_2$ for 3 times and stirred at 80° C. for 16 hr. LCMS showed the starting material was consumed completely and the desired product was detected. TLC showed the starting material was consumed completely. The mixture was cooled to 15° C. and concentrated to remove dioxane. The mixture was dissolved EtOAc (50 mL) and H$_2$O (50 mL). The aqueous layer was extracted with EtOAc (30 mL×3), the combined organic layers were washed with brine (5 mL), dried over anhydrous Na$_2$SO$_4$, filtered and concentrated under reduced pressure to give a residue. The residue was purified by column chromatography to give the crude product. The crude product was purified by prep-HPLC to give the desired product Compound 45 (20.13 mg, yield: 4%) as a yellow solid.

LCMS: m/z, 298.1 (M+H)$^+$;

$^1$H NMR (400 MHz CDCl$_3$): δ 8.71 (d, J=4.8 Hz, 1H), 7.24 (t, J=4.8 Hz, 1H), 6.17 (dd, J=10.4, 2.8 Hz, 1H), 6.03 (d, J=8.4 Hz, 2H), 3.73 (d, J=8.8 Hz, 1H), 3.50 (d, J=8.0 Hz, 1H), 3.40-3.43 (m, 1H), 2.22-2.27 (m, 1H), 1.47-1.50 (m, 1H), 1.07 (t, J=4.8 Hz, 1H).

Procedure for Preparation of Compound 46

To a mixture of 17 (300 mg, 1.62 mmol) in anhydrous dioxane (10 mL) was Cs$_2$CO$_3$ (1.58 g, 4.86 mmol), Xtanphos (93.7 mg, 162 μmol), compound 69 (359 mg, 1.62 mmol) and Pd$_2$(dba)$_3$ (148 mg, 162 μmol) at 5-10° C. The mixture was degassed and purged with N$_2$ for 3 times, and then the mixture was stirred at 80° C. for 16 hrs under N$_2$ atmosphere. LCMS showed the starting material was consumed completely and the desired product was detected. TLC showed the starting material was consumed completely. The mixture was poured into H$_2$O (50 mL). The aqueous layer was extracted with EtOAc (50 mL×3) and the combined organic layers were washed with brine (15 mL), dried over anhydrous Na$_2$SO$_4$, filtered and concentrated under reduced pressure to give a residue. The residue was purified by column chromatography to give the crude product. The crude product was purified by prep-HPLC to give the desired Compound 46 (34.29 mg, yield: 8%) as a yellow solid.

LCMS: m/z, 280.1 (M+H)$^+$;

$^1$H NMR (400 MHz CDCl$_3$): δ 8.71 (d, J=4.8 Hz, 1H), 7.23 (t, J=4.8 Hz, 1H), 7.15 (q, J=8.0 Hz, 1H), 6.42-6.43 (m, 1H), 6.32 (d, J=8.4 Hz, 1H), 6.26 (dd, J=14.0, 2.4 Hz, 1H), 3.78 (d, J=9.2 Hz, 1H), 3.56 (d, J=9.2 Hz, 1H), 3.49 (d, J=9.2 Hz, 1H), 3.38-3.41 (m, 1H), 2.21-2.26 (m, 1H), 1.44-1.47 (m, 1H), 1.11 (t, J=4.8 Hz, 1H).

Example Compound 46

Preparation of 3-(3-fluorophenyl)-1-(pyrimidin-2-ylethynyl)-3-azabicyclo[3.1.0]hexane Example Compound 47

Preparation of 3-(1-((2-methylthiazol-4-yl)ethynyl)-3-azabicyclo[3.1.0]hexan-3-yl)benzonitrile

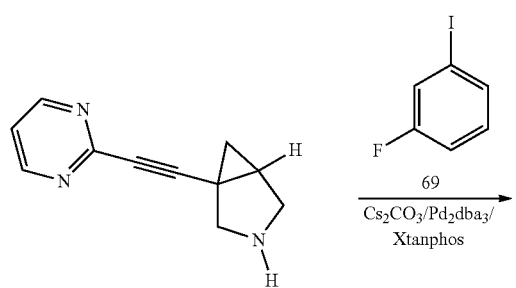

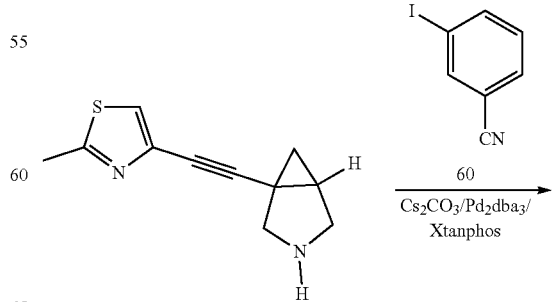

75

-continued

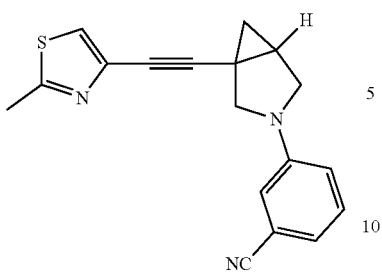

Compound 47

Experimental Section

Procedure for Preparation of Compound 47

To a mixture of 59 (300 mg, 1.47 mmol) in anhydrous dioxane (10 mL) was added Cs$_2$CO$_3$ (1.44 g, 4.41 mmol), Xtanphos (85.1 mg, 147 μmol), 60 (337 mg, 1.47 mmol) and Pd$_2$(dba)$_3$ (135 mg, 147 μmol) at 5-10° C. The mixture was degassed and purged with N$_2$ for 3 times, and then the mixture was stirred at 80° C. for 16 hr. TLC showed the starting material was consumed completely. The mixture was poured into H$_2$O (50 mL). The aqueous layer was extracted with EtOAc (50 mL×3) and the combined organic layers were washed with brine (15 mL), dried over anhydrous Na$_2$SO$_4$, filtered and concentrated under reduced pressure to give a residue. The residue was purified by column chromatography to give the crude product. The crude product was purified by prep-HPLC to give the desired product Compound 47 (42.54 mg, yield: 9%) as a yellow solid.

LCMS: m/z, 306.1 (M+H)$^+$;

$^1$H NMR (400 MHz CDCl$_3$): δ 7.27-7.29 (m, 1H), 7.25 (s, 1H), 6.98 (d, J=8.0 Hz, 1H), 6.73-6.75 (m, 2H), 3.75 (d, J=8.8 Hz, 1H), 3.55 (d, J=9.2 Hz, 1H), 3.41-3.46 (m, 2H), 2.71 (s, 3H), 2.13-2.17 (m, 1H), 1.36-1.39 (m, 1H), 1.00 (t, J=4.8 Hz, 1H).

Example Compound 48

Preparation of 4-((3-(5-fluoropyridin-3-yl)-3-azabicyclo[3.1.0]hexan-1-yl)ethynyl)-2-methylthiazole

76

-continued

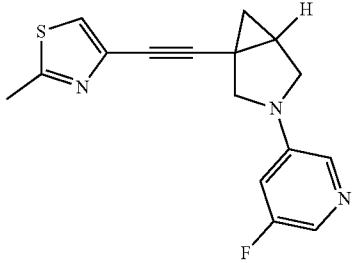

Compound 48

Experimental Section

Procedure for Preparation of Compound 48

To a solution of 59 (300 mg, 1.47 mmol) in anhydrous dioxane (2.00 mL) was added Cs$_2$CO$_3$ (1.44 g, 4.41 mmol), Xtanphos (85.0 mg, 147 μmol), 66 (258 mg, 1.47 mmol) and Pd$_2$(dba)$_3$ (134 mg, 147 μmol) at 5-10° C. The mixture was degessed with N$_2$ for 3 times and stirred at 80° C. for 16 hr. TLC showed the starting material was consumed completely and the main spot was detected. The mixture was cooled to 15° C. The mixture was poured into H$_2$O (50 mL) at 0-5° C. The aqueous layer ware extracted with EtOAc (25 mL×3). The combined organic layers were washed with brine (15 mL), dried over anhydrous Na$_2$SO$_4$, filtered and concentrated under reduced pressure to give a residue. The residue was purified by column chromatography to give the crude product. The crude product was purified by prep-HPLC to give the desired product Compound 48 (23.06 mg, yield: 5%) as a yellow solid.

LCMS: m/z, 300.0 (M+H)$^+$;

$^1$H NMR (400 MHz CDCl$_3$): δ 7.85 (d, J=2.0 Hz, 1H), 7.80 (s, 1H), 7.25 (s, 1H), 6.51-6.55 (m, 1H), 3.76 (d, J=8.8 Hz, 1H), 3.56 (d, J=9.2 Hz, 1H), 3.44-3.49 (m, 2H), 2.71 (s, 3H), 2.14-2.18 (m, 1H), 1.37-1.41 (m, 1H), 1.01 (t, J=4.8 Hz, 1H).

Example Compound 49

Preparation of (3-chlorophenyl)-(1-((2-methylthiazol-4-yl)ethynyl)-3-azabicyclo[3.1.0]hexan-3-yl)methanone

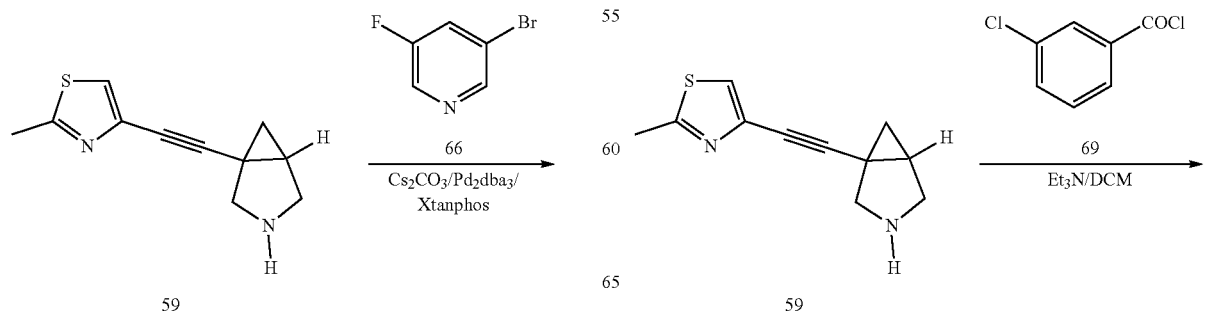

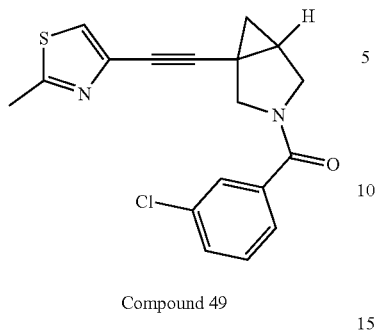

Compound 49

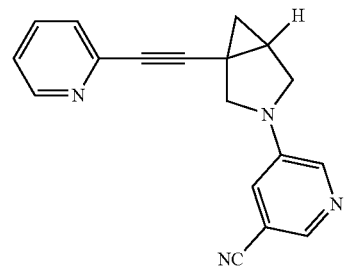

Compound 50

Experimental Section

Procedure for Preparation of Compound 49

To a solution of 59 (250 mg, 1.22 mmol) in DCM (3.00 mL) was added Et$_3$N (1.23 g, 12.2 mmol) at 5-10° C. The mixture was stirred at 15° C. for 15 mins. 69 (256 mg, 1.46 mmol) was added to the above mixture at 5-10° C. The mixture was stirred at 15° C. for 2 hr. TLC showed the starting material was consumed completely. The mixture was poured into ice-water (5 mL), the aqueous layer was extracted with DCM (5 mL×2), the combined organic layers were washed with brine (2 mL), dried over anhydrous Na$_2$SO$_4$, filtered and concentrated under reduced pressure to give a residue. The residue was purified by prep-HPLC to give the desired product Compound 49 (42.34 mg, yield: 10%) as yellow oil.

LCMS: m/z, 343.1 (M+H)$^+$;

$^1$H NMR (400 MHz CDCl$_3$): δ 7.37-7.43 (m, 2H), 7.31-7.37 (m, 2H), 7.21 (s, 1H), 4.23-4.45 (m, 1H), 3.50-3.81 (m, 3H), 2.70 (d, J=6.8 Hz, 3H), 1.95-2.06 (m, 1H), 1.30-1.33 (m, 1H), 0.81 (t, J=4.8 Hz, 1H).

Example Compound 50

Preparation of S-(1-(pyridin-2-ylethynyl)-3-azabicyclo[3.1.0]hexan-3-yl)nicotinonitrile Experimental Section Procedure for Preparation of Compound 50

A mixture of 6 (150 mg, 814 μmol), 70 (149 mg, 814 μmol), Cs$_2$CO$_3$ (796 mg, 2.44 mmol), Pd$_2$(dba)$_3$ (74.6 mg, 81.4 μmol) and Xantphos (47.1 mg, 81.4 μmol) in dioxane (5.00 mL) was stirred under N$_2$ at 45° C. for 16 hrs. TLC and LCMS showed the reaction was complete. The mixture was cooled to 25° C. and filtered. The filtrate was concentrated in vacuum. The residue was purified by prep-HPLC to give the desired product Compound 50 (18.0 mg, yield: 7.7%) as a yellow solid.

LCMS: m/z, 287.1 (M+H)$^+$;

$^1$H NMR (400 MHz DMSO): δ 8.53 (dd, J=4.8, 0.8 Hz, 1H), 8.25 (dd, J=4.8, 2.0 Hz, 2H), 7.79 (td, J=7.6, 1.6 Hz, 1H), 7.48 (dt, J=8.0, 0.8 Hz, 1H), 7.44 (dd, J=2.8, 1.6 Hz, 1H), 7.33-7.39 (m, 1H), 3.92 (d, J=9.6 Hz, 1H), 3.68 (d, J=9.6 Hz, 1H), 3.39-3.46 (m, 2H), 2.25-2.32 (m, 1H), 1.34 (dd, J=8.0, 4.8 Hz, 1H), 1.00 (t, J=4.8 Hz, 1H).

Example Compound 51

Preparation of cyclopentyl((1R,5S)-1-(pyridin-2-ylethynyl)-3-azabicyclo[3.1.0]hexan-3-yl)methanone

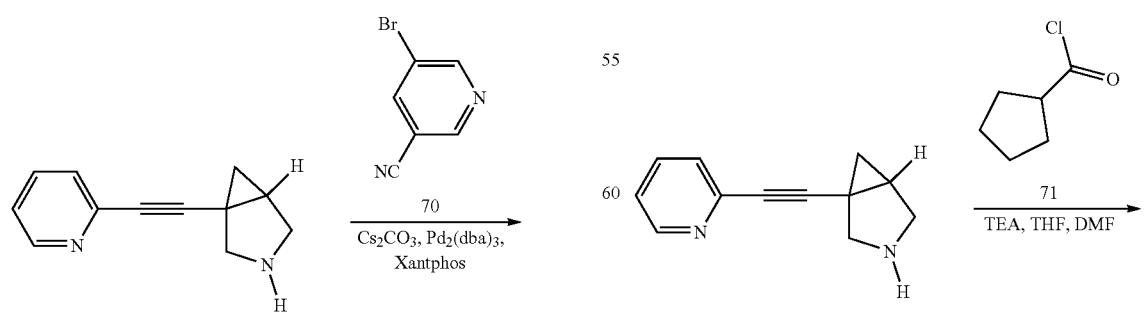

79

-continued

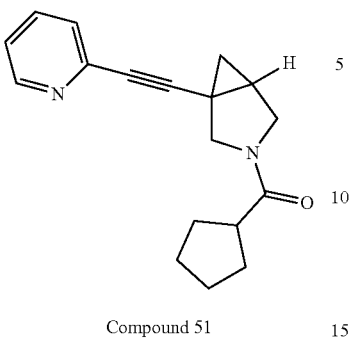

Compound 51

Experimental Section:

Procedure for Preparation of Compound 51:

To a mixture of 6 (150 mg, 680 μmol) in THF (6.00 mL) and DMF (2.00 mL) was added TEA (550 mg, 5.44 mmol) dropwise at 0° C. The mixture was stirred at 0° C. for 10 min, then 71 (108 mg, 816 μmol) was added dropwise at 0° C. The mixture was warmed to 25° C. and stirred for 2 hrs. TLC showed the reaction was complete. The mixture was poured into water (20 mL) and extracted with EtOAc (3*20 mL). The combined organic layers were washed with brine (40 mL), dried over anhydrous $Na_2SO_4$ and concentrated in vacuum. The residue was purified by prep-HPLC to give the desired product Compound 51 (35.0 mg, yield: 18%) as a yellow oil.

LCMS: m/z, 281.1 $(M+H)^+$;

$^1$H NMR (400 MHz DMSO): δ 8.49-8.55 (m, 1H), 7.77 (tt, J=7.6, 2.0 Hz, 1H), 7.44-7.50 (m, 1H), 7.35 (br. dd, J=6.8, 5.6 Hz, 1H), 3.88-4.01 (m, 1H), 3.63-3.75 (m, 1H), 3.63-3.75 (m, 2H), 3.34-3.40 (m, 1H), 2.71-2.84 (m, 1H), 2.03-2.18 (m, 1H), 1.69-1.82 (m, 2H), 1.44-1.68 (m, 6H), 1.24-1.31 (m, 1H), 0.81 (t, J=4.8 Hz, 1H).

Example Compound 52

Preparation of 2,2-dimethyl-1-((1R,5S)-1-(pyridin-2-ylethynyl)-3-azabicyclo[3.1.0]hexan-3-yl)propan-1-one

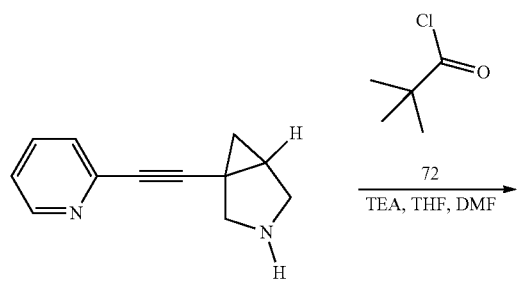

80

-continued

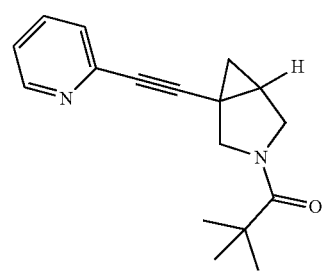

Compound 52

Experimental Section

Procedure for Preparation of Compound 52

To a mixture of 6 (150 mg, 680 μmol) in THF (6.00 mL) and DMF (2.00 mL) was added TEA (550 mg, 5.44 mmol) dropwise at 0° C. The mixture was stirred at 0° C. for 10 min, then 52 (98.34 mg, 816 μmol) was added dropwise at 0° C. The mixture was warmed to 25° C. and stirred for 2 hrs. TLC showed the reaction was complete. The mixture was poured into water (20 mL) and extracted with EtOAc (3*20 mL). The combined organic layers were washed with brine (40 mL), dried over anhydrous $Na_2SO_4$ and concentrated in vacuum. The residue was purified by prep-HPLC to give the desired product Compound 52 (38.0 mg, yield: 21%) as a yellow oil.

LCMS: m/z, 269.1 $(M+H)^+$;

$^1$H NMR (400 MHz DMSO): δ 8.49-8.54 (m, 1H), 7.77 (td, J=7.6, 1.6 Hz, 1H), 7.44-7.51 (m, 1H), 7.35 (ddd, J=7.6, 4.8, 1.2 Hz, 1H), 4.08 (br. d, J=9.2 Hz, 1H), 3.86 (br. d, J=10.4 Hz, 1H), 3.39-3.67 (m, 2H), 2.08 (br. s, 1H), 1.23 (dd, J=8.0, 4.8 Hz, 1H), 1.14 (s, 9H), 0.77 (t, J=4.8 Hz, 1H).

Example Compound 53

Preparation of methyl 1-(pyridin-2-ylethynyl)-3-azabicyclo[3.1.0]hexane-3-carboxylate

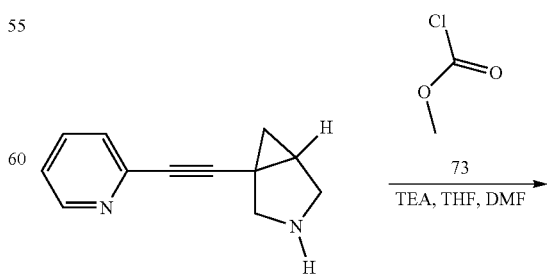

-continued

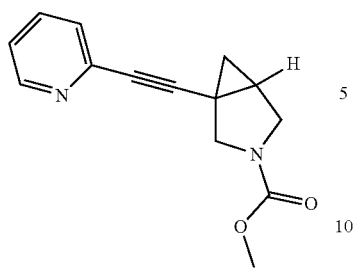

Compound 53

Experimental Section

Procedure for Preparation of Compound 53

To a mixture of 6 (150 mg, 680 μmol) in THF (6.00 mL) and DMF (2.00 mL) was added TEA (550 mg, 5.44 mmol) dropwise at 0° C. The mixture was stirred at 0° C. for 10 min, then 73 (77.1 mg, 816 μmol) was added dropwise at 0° C. The mixture was warmed to 25° C. and stirred for 2 hrs. TLC showed the reaction was complete. The mixture was poured into water (20 mL) and extracted with EtOAc (3*20 mL). The combined organic layers were washed with brine (40 mL), dried over anhydrous $Na_2SO_4$ and concentrated in vacuum. The residue was purified by prep-HPLC to give the desired product Compound 53 (40.0 mg, yield: 24%) as a yellow solid.

LCMS: m/z, 243.0 $(M+H)^+$;

$^1$H NMR (400 MHz DMSO): δ 8.49-8.54 (m, 1H), 7.77 (td, J=7.6, 2.0 Hz, 1H), 7.46 (d, J=8.0 Hz, 1H), 7.35 (ddd, J=7.6, 4.8, 1.2 Hz, 1H), 3.74 (br. d, J=9.6 Hz, 1H), 3.58 (s, 3H), 3.41-3.53 (m, 3H), 2.08 (br. s, 1H), 1.28 (dd, J=7.6, 5.2 Hz, 1H), 0.86 (t, J=5.2 Hz, 1H).

Example Compound 54

Preparation of (5-chloropyridin-3-yl)((1R,5S)-1-(pyridin-2-ylethynyl)-3-azabicyclo[3.1.0]hexan-3-yl)methanone

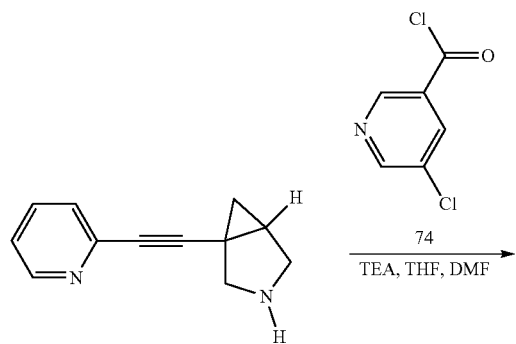

-continued

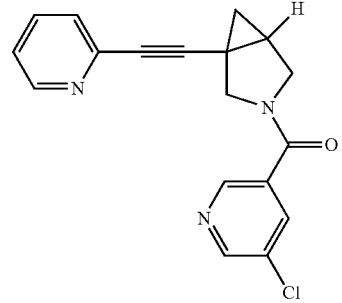

Compound 54

Experimental Section

Procedure for Preparation of Compound 54

To a mixture of 6 (150 mg, 814 μmol) in THF (6.00 mL) and DMF (2.00 mL) was added TEA (659 mg, 6.51 mmol) dropwise at 0° C. The mixture was stirred at 0° C. for 10 min, then 74 (143 mg, 814 μmol) was added dropwise at 0° C. The mixture was warmed to 25° C. and stirred for 2 hrs. TLC showed the reaction was complete. The mixture was poured into water (20 mL) and extracted with EtOAc (3*20 mL). The combined organic layers were washed with brine (40 mL), dried over anhydrous $Na_2SO_4$ and concentrated in vacuum. The residue was purified by prep-HPLC to give the desired product Compound 54 (34.0 mg, yield: 13%) as a yellow oil.

LCMS: m/z, 324.0 $(M+H)^+$;

$^1$H NMR (400 MHz DMSO): δ 8.73 (d, J=2.4 Hz, 1H), 8.64 (dd, J=5.2, 1.6 Hz, 1H), 8.52 (br. dd, J=9.6, 4.8 Hz, 1H), 8.05-8.12 (m, 1H), 7.72-7.83 (m, 1H), 7.42-7.51 (m, 1H), 7.31-7.39 (m, 1H), 4.21 (d, J=11.6 Hz, 1H), 4.00 (d, J=12.0 Hz, 1H), 3.91 (br. d, J=10.2 Hz, 1H), 3.35-3.66 (m, 1H), 3.38 (d, J=10.6 Hz, 1H), 2.06-2.20 (m, 1H), 1.28 (br. t, J=6.0 Hz, 1H), 0.96-1.05 (m, 1H).

Example Compound 55

Preparation of (4-chloropyridin-2-yl)-(1-(pyridin-2-ylethynyl)-3-azabicyclo[3.1.0]hexan-3-yl)methanone

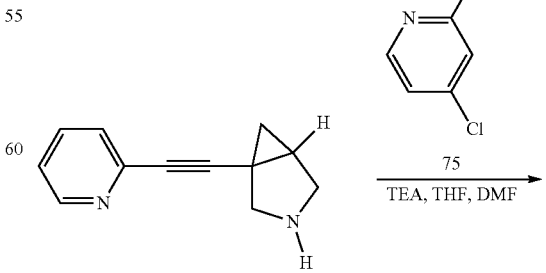

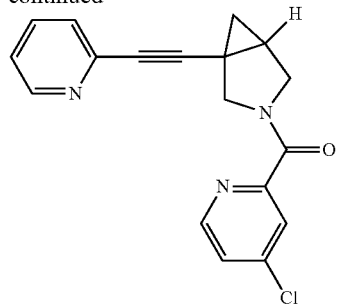

Compound 55

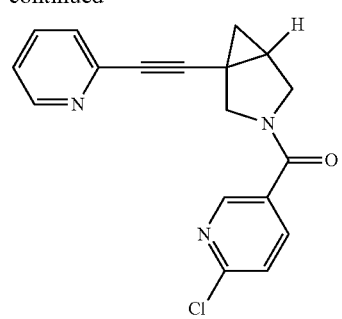

Compound 56

Experimental Section

Procedure for Preparation of Compound 55

To a mixture of 6 (150 mg, 814 µmol) in THF (6.00 mL) and DMF (2.00 mL) was added TEA (659 mg, 6.51 mmol) dropwise at 0° C. The mixture was stirred at 0° C. for 10 min, then 75 (143 mg, 814 µmol) was added dropwise at 0° C. The mixture was warmed to 25° C. and stirred for 2 hrs. TLC showed the reaction was complete. The mixture was poured into water (20 mL) and extracted with EtOAc (3*20 mL). The combined organic layers were washed with brine (40 mL), dried over anhydrous Na$_2$SO$_4$ and concentrated in vacuum. The residue was purified by prep-HPLC to give the desired product Compound 55 (50.0 mg, yield: 19%) as a yellow oil.

LCMS: m/z, 324.0 (M+H)$^+$;

$^1$H NMR (400 MHz DMSO): δ 8.60 (dd, J=8.0, 5.2 Hz, 1H), 8.49-8.55 (m, 1H), 7.74-7.82 (m, 2H), 7.66-7.71 (m, 1H), 7.44-7.51 (m, 1H), 7.35 (dddd, J=7.6, 6.4, 4.8, 1.2 Hz, 1H), 4.01-4.23 (m, 1H), 3.74-4.01 (m, 2H), 3.57-3.68 (m, 1H), 2.10-2.18 (m, 1H), 1.29 (dd, J=8.0, 4.8 Hz, 1H), 0.89-0.95 (m, 1H).

Example Compound 56

Preparation of (6-chloropyridin-3-yl)-(1-(pyridin-2-ylethynyl)-3-azabicyclo[3.1.0]hexan-3-yl)methanone

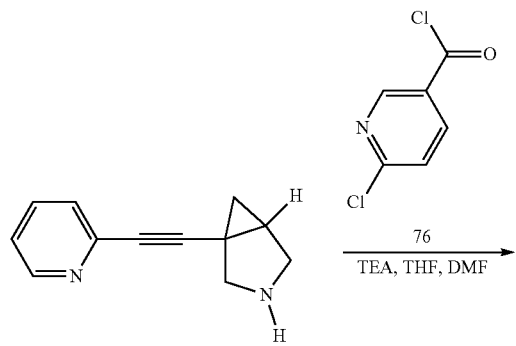

Procedure for Preparation of Compound 56

To a mixture of 6 (150 mg, 680 µmol) in THF (6.00 mL) and DMF (2.00 mL) was added TEA (550.19 mg, 5.44 mmol) dropwise at 0° C. The mixture was stirred at 0° C. for 10 min, then 76 (144 mg, 816 µmol) was added dropwise at 0° C. The mixture was warmed to 25° C. and stirred for 2 hrs. TLC showed the reaction was complete. The mixture was poured into water (20 mL) and extracted with EtOAc (3*20 mL). The combined organic layers were washed with brine (40 mL), dried over anhydrous Na$_2$SO$_4$ and concentrated in vacuum. The residue was purified by prep-HPLC to give the desired product Compound 56 (40.0 mg, yield: 18%) as a yellow oil.

LCMS: m/z, 324.0 (M+H)$^+$;

$^1$H NMR (400 MHz DMSO): δ 8.48-8.57 (m, 2H), 7.99 (br. t, J=7.6 Hz, 1H), 7.73-7.82 (m, 1H), 7.60 (br. d, J=8.0 Hz, 1H), 7.41-7.52 (m, 1H), 7.31-7.39 (m, 1H), 3.96-4.26 (m, 1H), 3.90 (br. d, J=10.0 Hz, 1H), 3.37-3.66 (m, 2H), 2.06-2.19 (m, 1H), 1.28 (br. t, J=6.0 Hz, 1H), 0.97 (br. d, J=4.4 Hz, 1H).

Example Compound 57

Preparation of N-phenyl-1-(pyridin-2-ylethynyl)-3-azabicyclo[3.1.0]hexane-3-carboxamide

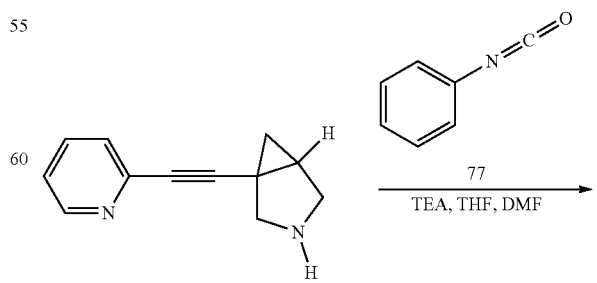

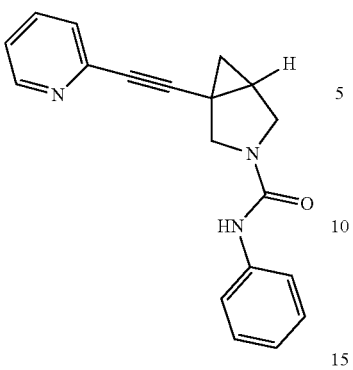

Compound 57

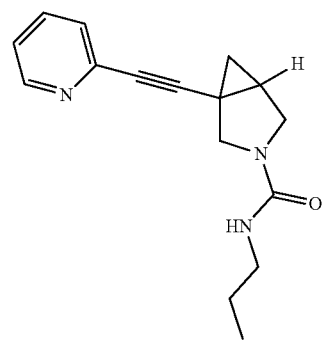

Compound 58

Experimental Section

Procedure for Preparation of Compound 57

To a mixture of 6 (150 mg, 680 μmol) in THF (6.00 mL) and DMF (2.00 mL) was added TEA (550 mg, 5.44 mmol) dropwise at 0° C. The mixture was stirred at 0° C. for 10 min, then 77 (97.2 mg, 816 μmol) was added dropwise at 0° C. The mixture was warmed to 25° C. and stirred for 2 hrs. TLC showed the reaction was complete. The mixture was poured into water (20 mL) and extracted with EtOAc (3*20 mL). The combined organic layers were washed with brine (40 mL), dried over anhydrous $Na_2SO_4$ and concentrated in vacuum. The residue was purified by prep-HPLC to give the desired product Compound 57 (45.0 mg, yield: 22%) as a yellow solid.

LCMS: m/z, 304.1 $(M+H)^+$;

$^1H$ NMR (400 MHz DMSO): δ 8.51-8.56 (m, 1H), 8.20 (s, 1H), 7.78 (td, J=7.6, 1.6 Hz, 1H), 7.44-7.52 (m, 3H), 7.35 (ddd, J=7.6, 4.8, 1.2 Hz, 1H), 7.18-7.26 (m, 2H), 6.90-6.97 (m, 1H), 3.95 (d, J=10.0 Hz, 1H), 3.73 (d, J=10.4 Hz, 1H), 3.49-3.56 (m, 2H), 2.09-2.17 (m, 1H), 1.29 (dd, J=8.0, 4.8 Hz, 1H), 0.91 (t, J=4.8 Hz, 1H).

Example Compound 58

Preparation of (1R,5S)—N-propyl-1-(pyridin-2-ylethynyl)-3-azabicyclo[3.1.0]hexane-3-carboxamide Experimental Section Procedure for Preparation of Compound 58

To a mixture of 6 (150 mg, 680 μmol) in THF (6.00 mL) and DMF (2.00 mL) was added TEA (550 mg, 5.44 mmol) dropwise at 0° C. The mixture was stirred at 0° C. for 10 min, then 78 (69.4 mg, 816 μmol) was added dropwise at 0° C. The mixture was warmed to 25° C. and stirred for 2 hrs. TLC showed the reaction was complete. The mixture was poured into water (20 mL) and extracted with EtOAc (3*20 mL). The combined organic layers were washed with brine (40 mL), dried over anhydrous $Na_2SO_4$ and concentrated in vacuum. The residue was purified by prep-HPLC to give the desired product Compound 58 (28.0 mg, yield: 15%) as a yellow oil.

LCMS: m/z, 270.1 $(M+H)^+$;

$^1H$ NMR (400 MHz DMSO): δ 8.48-8.54 (m, 1H), 7.77 (td, J=7.6, 1.6 Hz, 1H), 7.46 (dt, J=8.0, 1.2 Hz, 1H), 7.34 (ddd, J=7.6, 4.8, 1.2 Hz, 1H), 6.21 (t, J=5.6 Hz, 1H), 3.75 (d, J=9.6 Hz, 1H), 3.53 (d, J=10 Hz, 1H), 3.32-3.37 (m, 2H), 2.90-2.99 (m, 2H), 2.01-2.09 (m, 1H), 1.39 (sxt, J=7.2 Hz, 2H), 1.22 (dd, J=8.0, 4.8 Hz, 1H), 0.78-0.85 (m, 4H).

Example Compound 59

Preparation of (1-(pyridin-2-ylethynyl)-3-azabicyclo[3.1.0]hexan-3-yl)(pyrrolidin-1-yl)methanone

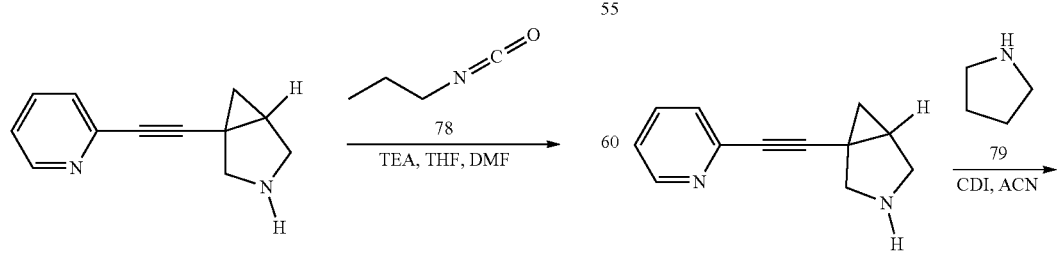

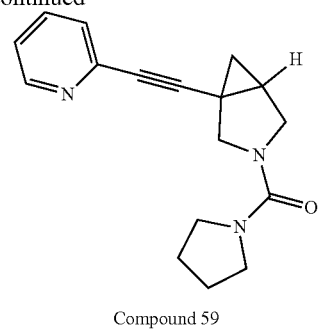

Compound 59

Experimental Section

Procedure for Preparation of Compound 59

To a solution of CDI (132 mg, 814 μmol) in ACN (2.00 mL) was added a solution of 6 (150 mg, 814 μmol) in ACN (2.00 mL) dropwise under N₂ at 0° C. After stirring at 25° C. for 1 hr, 79 (290 mg, 4.07 mmol) was added dropwise at 25° C. The reaction mixture was stirred at 80° C. for 48 hrs. TLC showed the reaction was complete. The mixture was concentrated in vacuum. The residue was purified by prep-HPLC to give the desired product Compound 59 (47.0 mg, yield: 20%) as a yellow oil.

LCMS: m/z, 282.1 (M+H)⁺;

¹H NMR (400 MHz DMSO): δ 8.48-8.54 (m, 1H), 7.77 (td, J=7.6, 1.6 Hz, 1H), 7.43-7.49 (m, 1H), 7.34 (ddd, J=7.6, 4.8, 1.2 Hz, 1H), 3.89 (d, J=10.4 Hz, 1H), 3.67 (d, J=10.4 Hz, 1H), 3.40 (dd, J=10.4, 3.6 Hz, 1H), 3.36 (d, J=10.4 Hz, 1H), 3.20-3.28 (m, 4H), 1.97-2.04 (m, 1H), 1.70-1.76 (m, 4H), 1.18 (dd, J=8.0, 4.8 Hz, 1H), 0.68 (t, J=4.8 Hz, 1H).

Example Compound 60

Preparation of 1-(pyridin-2-yl-ethynyl)-N-(2,2,2-trifluoroethyl)-3-azabicyclo[3.1.0]hexane-3-carboxamide

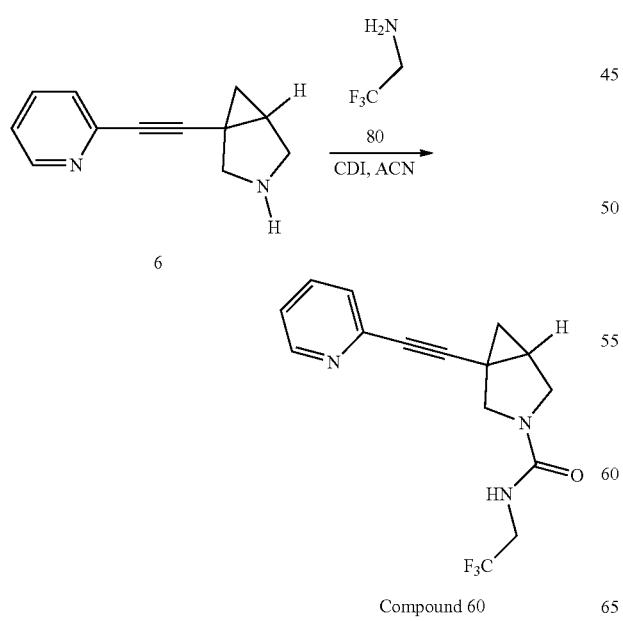

Compound 60

Experimental Section

Procedure for Preparation of Compound 60

To a solution of CDI (264 mg, 1.63 mmol) in ACN (6.00 mL) was added 80 (161 mg, 1.63 mmol) dropwise under N₂ at 25° C. After stirring for 1 hr, a solution of 6 (300 mg, 1.63 mmol) in ACN (4.00 mL) was added dropwise. The reaction mixture was stirred at 25° C. for 12 hrs. TLC and LCMS showed the reaction was complete. The reaction mixture was concentrated in vacuum. The residue was purified by prep-HPLC to give the desired product Compound 60 (38.0 mg, yield: 7.5%) as a yellow oil.

LCMS: m/z, 310.0 (M+H)⁺;

¹H NMR (400 MHz DMSO): δ 8.52 (d, J=4.8 Hz, 1H), 7.77 (td, J=7.6, 1.6 Hz, 1H), 7.46 (d, J=7.6 Hz, 1H), 7.35 (ddd, J=7.6, 4.8, 1.2 Hz, 1H), 6.93 (t, J=6.4 Hz, 1H), 3.72-3.85 (m, 3H), 3.57 (d, J=10.4 Hz, 1H), 3.36-3.46 (m, 2H), 2.09 (dt, J=8.0, 4.4 Hz, 1H), 1.26 (dd, J=8.0, 4.8 Hz, 1H), 0.80 (t, J=4.8 Hz, 1H).

Example Compound 61

Preparation of (3-chlorophenyl)-(1-(pyrimidin-2-ylethynyl)-3-azabicyclo[3.1.0]hexan-3-yl)methanone

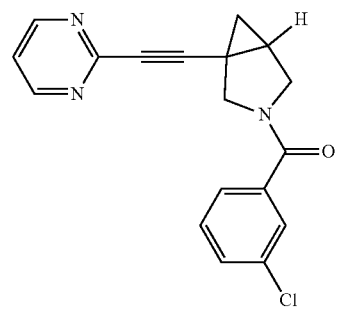

Compound 61

Experimental Section

Procedure for Preparation of Compound 61

To a solution of 17 (114 mg, 615.48 μmol) in DCM (2.00 mL) was added TEA (623 mg, 6.15 mmol) at 25° C. The mixture was stirred at 25° C. for 30 mins. Add 81 (129 mg, 739 μmol) to the above mixture at 25° C. The mixture was stirred at 25° C. for 2 hr. TLC indicated 17 was consumed completely and one new spot formed. The mixture was poured into ice-water (50 mL), the aqueous layer was extracted with DCM (20 mL*2), the combined organic layers were washed with brine (50 mL), dried over anhydrous Na$_2$SO$_4$, filtered and concentrated under reduced pressure to give a residue. The residue was purified by prep-HPLC to give the desired product Compound 61 (26.0 mg, yield: 13%) as a yellow solid.

LCMS: m/z, 324.0 (M+H)$^+$;

$^1$H NMR (400 MHz DMSO): δ 8.76 (dd, J=10.4, 4.8 Hz, 2H), 7.52-7.57 (m, 2H), 7.41-7.50 (m, 3H), 3.97-4.27 (m, 1H), 3.82-3.91 (m, 1H), 3.33-3.60 (m, 2H), 2.11-2.25 (m, 1H), 1.31 (dd, J=8.0, 5.2 Hz, 1H), 0.98 (q, J=5.2 Hz, 1H).

Example Compound 62

Preparation of 3-(1-(pyrimidin-2-ylethynyl)-3-azabicyclo[3.1.0]hexan-3-yl)benzonitrile

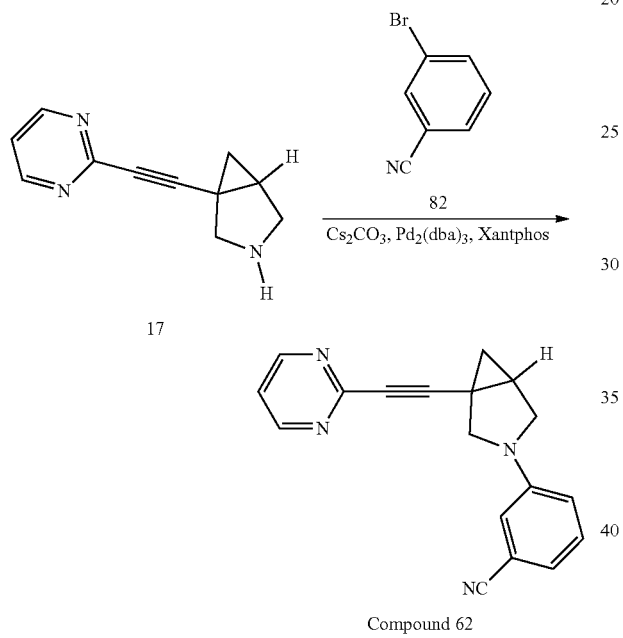

Compound 62

Experimental Section

Procedure for Preparation of Compound 62

To a solution of 17 (200 mg, 1.08 mmol) in dioxane (10 mL) was added Cs$_2$CO$_3$ (1.06 g, 3.24 mmol), Xantphos (62.3 mg, 108 μmol), 82 (197 mg, 1.08 mmol) and Pd$_2$(dba)$_3$ (98.9 mg, 108 mol) at 25° C. The mixture was degassed with N$_2$ with 3 times and the mixture was stirred at 80° C. for 16 hr. TLC showed 17 was consumed completely and the main spot was detected. The mixture was cooled to 15° C. The mixture was poured into H$_2$O (50 mL) at 0-5° C. The aqueous layer ware extracted with EtOAc (25 mL*3). The combined organic layers were washed with brine (15 mL), dried over anhydrous Na$_2$SO$_4$, filtered and concentrated under reduced pressure to give a residue. The crude product was purified by prep-HPLC to give the desired product Compound 62 (23.0 mg, yield: 7.4%) as a yellow solid.

LCMS: m/z, 287.0 (M+H)$^+$;

$^1$H NMR (400 MHz DMSO): δ 8.77 (d, J=5.2 Hz, 2H), 7.47 (t, J=4.8 Hz, 1H), 7.31-7.38 (m, 1H), 7.05 (d, J=7.6 Hz, 1H), 6.99-7.02 (m, 1H), 6.94 (dd, J=8.4, 2.0 Hz, 1H), 3.90 (d, J=9.2 Hz, 1H), 3.64 (d, J=9.6 Hz, 1H), 3.33-3.39 (m, 2H), 2.29-2.35 (m, 1H), 1.37 (dd, J=8.4, 4.4 Hz, 1H), 1.05 (t, J=4.8 Hz, 1H).

Example Compound 63

Preparation of 3-(5-fluoropyridin-3-yl)-1-(pyrimidin-2-ylethynyl)-3-azabicyclo[3.1.0]hexane

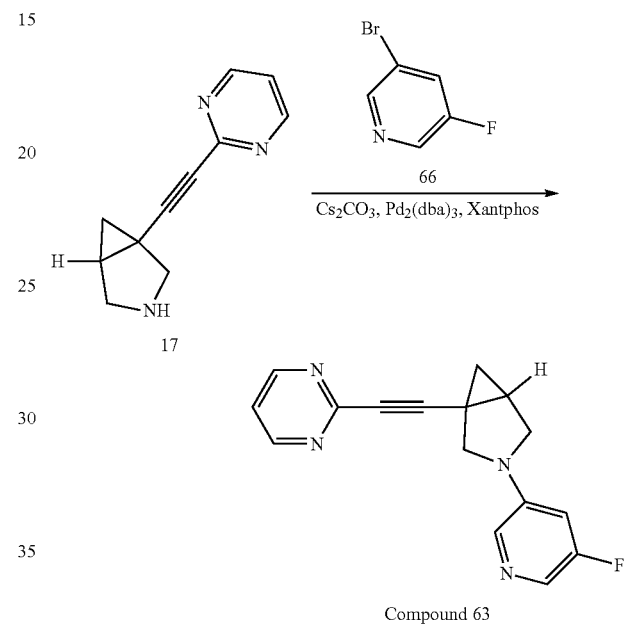

Compound 63

Experimental Section

Procedure for Preparation of Compound 63

To a solution of 17 (200 mg, 1.08 mmol) in dioxane (10 mL) was added Cs$_2$CO$_3$ (1.06 g, 3.24 mmol), Xantphos (62.3 mg, 108 μmol), 66 (190 mg, 1.08 mmol) and Pd$_2$(dba)$_3$ (98.9 mg, 108 mol) at 25° C. The mixture was degassed with N$_2$ with 3 times and the mixture was stirred at 80° C. for 16 hr. TLC showed 17 was consumed completely. The mixture was cooled to 25° C. The mixture was poured into H$_2$O (50 mL) at 0-5° C. The aqueous layer ware extracted with EtOAc (25 mL*3). The combined organic layers were washed with brine (50 mL), dried over anhydrous Na$_2$SO$_4$, filtered and concentrated under reduced pressure to give a residue. The crude product was purified by prep-HPLC to get the desired product Compound 63 (23.0 mg, yield: 7.6%) was obtained as a yellow solid.

LCMS: m/z, 281.0 (M+H)$^+$;

$^1$H NMR (400 MHz DMSO): δ 8.77 (br. d, J=4.8 Hz, 2H), 7.86 (br. d, J=13.2 Hz, 2H), 7.47 (br. s, 1H), 6.92 (br. d, J=11.6 Hz, 1H), 3.90 (br. d, J=9.2 Hz, 1H), 3.65 (br. d, J=9.2 Hz, 1H), 3.39 (br. d, J=9.2 Hz, 2H), 2.33 (br. s, 1H), 1.38 (br. s, 1H), 1.05 (br. s, 1H).

91

Example Compound 64

Preparation of 2-methyl-1-(1-((6-methylpyridin-2-yl)ethynyl)-3-azabicyclo[3.1.0]hexan-3-yl)propan-1-one

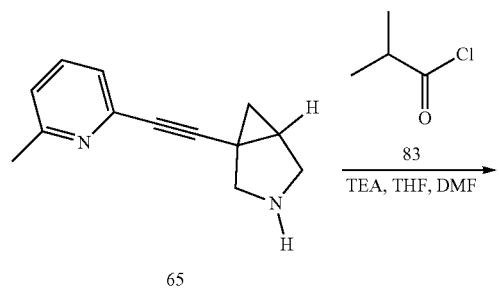

92

Example Compound 65

Preparation of 1-(1-((6-chloropyridin-2-yl)ethynyl)-3-azabicyclo[3.1.0]hexan-3-yl)-2-methylpropan-1-one

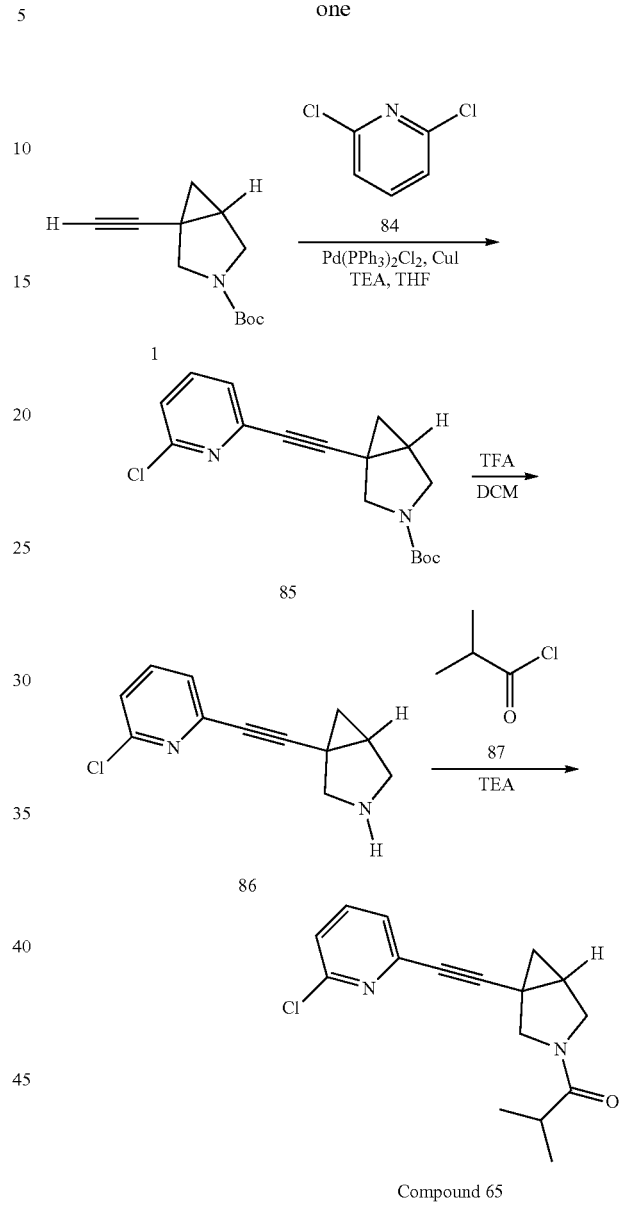

Experimental Section

Procedure for Preparation of Compound 64

To a mixture of 65 (200 mg, 640 μmol) in THF (6.00 mL) and DMF (2.00 mL) was added TEA (518 mg, 5.12 mmol) dropwise at 0° C. The mixture was stirred at 0° C. for 10 min, then 83 (81.9 mg, 769 μmol) was added dropwise at 0° C. The mixture was warmed to 25° C. and stirred for 2 hrs. TLC and LCMS showed the reaction was complete. The mixture was poured into water (20 mL) and extracted with EtOAc (3*20 mL). The combined organic layers were washed with brine (40 mL), dried over anhydrous $Na_2SO_4$ and concentrated in vacuum. The residue was purified by prep-HPLC to give the desired product Compound 64 (56.0 mg, yield: 33%) as a yellow oil.

LCMS: m/z, 269.1 (M+H)$^+$;

$^1$H NMR (400 MHz DMSO): δ 7.62-7.68 (m, 1H), 7.65 (td, J=7.6, 1.6 Hz, 1H), 7.26 (d, J=7.6 Hz, 1H), 7.21 (d, J=7.6 Hz, 1H), 3.86-3.98 (m, 1H), 3.65-3.72 (m, 2H), 3.33-3.39 (m, 1H), 2.55-2.65 (m, 1H), 2.42 (s, 3H), 2.02-2.17 (m, 1H), 1.24-1.31 (m, 1H), 0.94-1.00 (m, 6H), 0.80 (t, J=4.8 Hz, 1H).

Experimental Section

Procedure for Preparation of 85

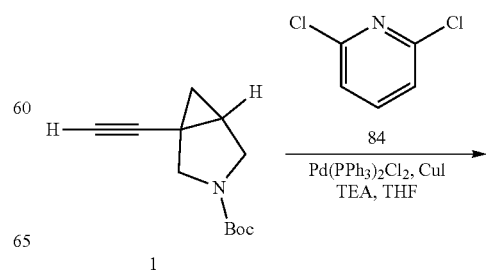

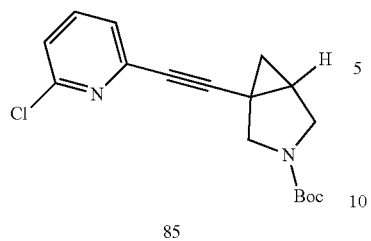

85

To a solution of 1 (500 mg, 2.41 mmol) in THF (5.00 mL) was added Pd(PPh$_3$)$_2$Cl$_2$ (84.7 mg, 120 μmol), 84 (355 mg, 2.41 mmol) and CuI (45.9 mg, 241 μmol) PPh$_3$ (63.2 mg, 241 μmol, 0.10 eq) at 15° C. The mixture was bubbling with N$_2$ at 15° C. Then the mixture was stirred at 40° C. for 16 hrs. TLC showed the starting material was consumed completely and a main spot was detected. The mixture was poured into H$_2$O (10 mL*3) at 5-10° C. The aqueous layer was extracted with Ethyl acetate (15 mL*3). The combined organic layers were washed with brine (10 mL), dried over anhydrous Na$_2$SO$_4$, filtered and concentrated under reduced pressure to give a residue. The residue was purified by column chromatography to give the desired product 85 (350 mg, yield: 45%) as yellow oil.

Procedure for Preparation of 86

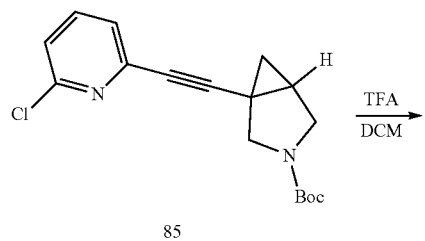

To a mixture of 85 (300 mg, 941 μmol) in DCM (10.0 mL) was added TFA (1.93 g, 16.9 mmol) in one portion at 15° C. under N$_2$ for 2 hours. TLC showed the starting material was consumed completely. The reaction mixture was extracted with ethyl acetate 30 mL (10 mL*3). The combined organic layers were washed with H$_2$O (10 mL*3), dried over Na$_2$SO$_4$, filtered and concentrated under reduced pressure to give a residue. The mixture was concentrated to give the desired product 86 (310 mg, crude, TFA) as yellow oil.

Procedure for Preparation of Compound 65

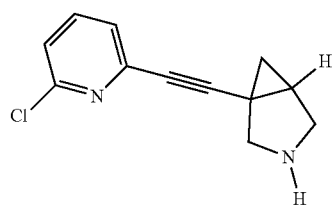

Compound 65

To a solution of 86 (310 mg, 1.42 mmol) in DCM (2.00 mL) was added Et$_3$N (1.44 g, 14.2 mmol) at 5-10° C. The mixture was stirred at 15° C. for 15 min. 87 was added (181 mg, 1.70 mmol) to the above mixture at 5-10° C. The mixture was stirred at 15° C. for 2 hrs. TLC showed the starting material was consumed completely. The mixture was poured into ice-water (5 mL), the aqueous layer was extracted with DCM (5 mL*2), and the combined organic layers were washed with brine (2 mL), dried over anhydrous Na$_2$SO$_4$, filtered and concentrated under reduced pressure to give a residue. The residue was purified by prep-TLC and lyophilized to give the desired product Compound 65 (33.0 mg, yield: 8.0%) as white oil.

LCMS: m/z, 275.0 (M+H)$^+$;

$^1$H NMR (400 MHz CDCl$_3$): δ 7.57-7.62 (m, 1H), 7.30-7.32 (m, 1H), 7.25-7.28 (m, 1H), 3.70-4.13 (m, 3H), 3.46-3.53 (m, m, 1H), 2.53-2.57 (m, 1H), 2.02-2.07 (m, 1H), 1.35-1.37 (t, J=8.0 Hz, 1H), 1.09-1.11 (d, J=7.2 Hz, 6H), 0.82-0.85 (t, J=8.6 Hz, 1H).

Example Compound 66

Preparation of (1-((2-methylthiazol-4-yl)ethynyl)-3-azabicyclo[3.1.0]hexan-3-yl)(phenyl)methanone

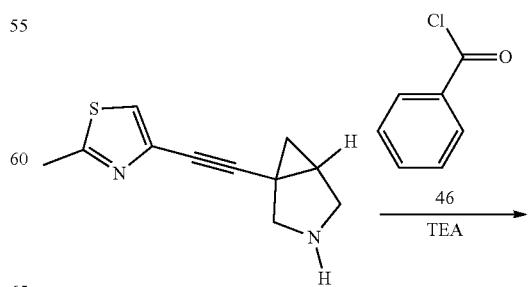

59

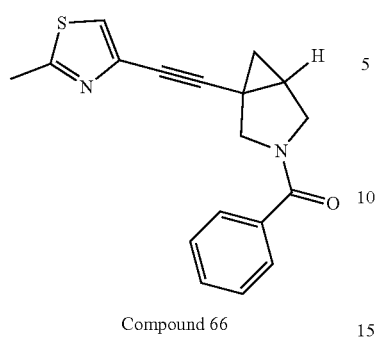

Compound 66

Experimental Section

Procedure for Preparation of Compound 66

To a solution of 59 (150 mg, 734 μmol) in DCM (10.00 mL) was added Et₃N (742.99 mg, 7.34 mmol) at 5-10° C. The mixture was stirred at 15° C. for 15 mins. 46 (123 mg, 881 μmol) was added to the above mixture at 5-10° C. The mixture was stirred at 15° C. for 2 hr. LCMS showed compound 59 was consumed completely and one main peak with desired MS was detected. The mixture was poured into ice-water (5 mL), the aqueous layer was extracted with DCM (5 mL*2), the combined organic layers were washed with brine (2 mL), dried over anhydrous Na₂SO₄, filtered and concentrated under reduced pressure to give a residue. The residue was purified by prep-TLC and lyophilized to give the desired product Compound 66 (35.0 mg, yield: 15%) as white oil.

LCMS: m/z, 309.1 (M+H)⁺;

¹H NMR (400 MHz CDCl₃): δ 7.13 (s, 5H), 7.19 (s, 1H), 4.25-4.47 (m, 1H), 3.50-3.80 (m, 3H), 2.70 (s, 3H), 1.94-2.02 (m, 1H), 1.26-1.29 (m, 1H), 0.82 (s, 1H).

Example Compound 67

Preparation of 1-(1-((2-mehylthyiazol-4-yl)ethynyl)-3-azabicyclo[3.1.0]hexan-3-yl)pentan-1-one

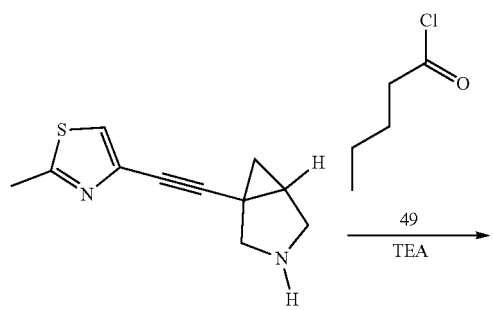

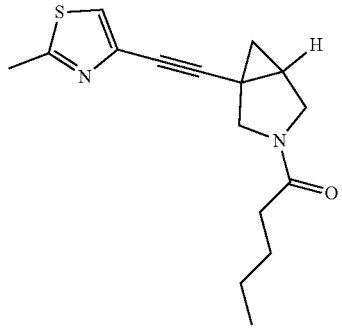

Compound 67

Experimental Section

Procedure for Preparation of Compound 67

To a solution of compound 59 (150 mg, 734 μmol) in DCM (10.0 mL) was added Et₃N (743 mg, 7.34 mmol) at 5-10° C. The mixture was stirred at 15° C. for 15 mins. Add pentanoyl chloride (106 mg, 881 μmol) to the above mixture at 5-10° C. The mixture was stirred at 15° C. for 2 hrs. LCMS showed 59 was consumed completely and one main peak with desired MS was detected. TLC indicated 59 was consumed completely and one new spot formed. The mixture was poured into ice-water (5 mL) and the aqueous layer was extracted with DCM (5 mL*2), the combined organic layers were washed with brine (2 mL), dried over anhydrous Na₂SO₄, filtered and concentrated under reduced pressure to give a residue. The residue was purified by prep-TLC and lyophilized to give the desired product Compound 67 (27.0 mg, yield: 13%) as a white solid.

LCMS: m/z, 289.0 (M+H)⁺;

¹H NMR (400 MHz CDCl₃): δ 7.23 (s, 1H), 3.87-4.10 (m, 1H), 3.57-3.78 (m, 2H), 3.48-3.51 (m, 1H), 2.70 (s, 3H), 2.19-2.24 (m, 2H), 1.99 (s, 1H), 1.58-1.62 (m, 2H), 1.32-1.38 (m, 3H), 0.92 (t, J=14.4 Hz, 3H), 0.79 (t, J=9.6 Hz, 1H).

Example Compound 68

Preparation of 2-methyl-1-(1-((2-methylthiazol-4-yl)ethynyl)-3-azabicyclo[3.1.0]hexan-3-yl)propan-1-one

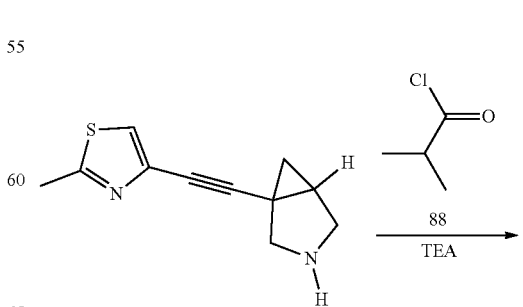

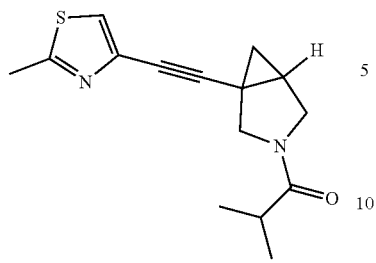

Compound 68

Experimental Section

Procedure for Preparation of Compound 68

To a solution of 59 (150 mg, 734 µmol) in DCM (10.0 mL) was added Et₃N (743 mg, 7.34 mmol) at 5-10° C. The mixture was stirred at 15° C. for 15 mins. 88 (93.9 mg, 881 µmol) was added to the above mixture at 5-10° C. The mixture was stirred at 15° C. for 2 hrs. LCMS showed 59 was consumed completely and one main peak with desired MS was detected. TLC indicated 59 was consumed completely and one new spot formed. The mixture was poured into ice-water (5 mL), the aqueous layer was extracted with DCM (5 mL*2), and the combined organic layers were washed with brine (2 mL), dried over anhydrous Na₂SO₄, filtered and concentrated under reduced pressure to give a residue. The residue was purified by prep-TLC and lyophilized to give the desired product Compound 68 (17.0 mg, 8.4% yield) as a white solid.

LCMS: m/z, 275.0 (M+H)⁺;

$^1$H NMR (400 MHz CDCl₃): δ 7.23 (s, 1H), 4.10 (d, J=11.6 Hz, 1H), 3.85-3.92 (m, 1H), 3.67-3.74 (m, 2H), 3.45-3.51 (m, 1H), 2.70 (s, 3H), 2.53-2.69 (m, 1H), 1.97-2.03 (m, 1H), 1.32 (t, J=8.8 Hz, 1H), 1.11 (d, J=6.4 Hz, 6H), 0.79 (t, J=6.0 Hz, 1H).

Example Compound 69

Preparation of 2,2-dimethyl-1-(1-((2-methylthiazol-4-yl)ethynyl)-3-azabicyclo[3.1.0]hexan-3-yl)propan-1-one

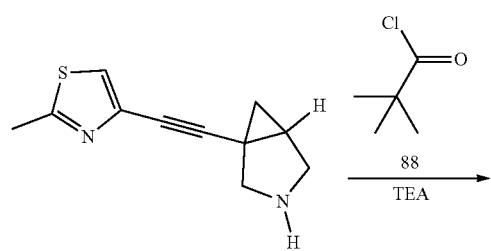

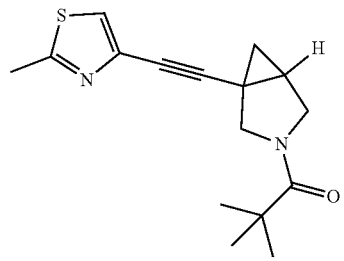

Compound 69

Experimental Section

Procedure for Preparation of Compound 69

To a solution of 59 (150 mg, 734 µmol) in DCM (10.0 mL) was added Et₃N (742.99 mg, 7.34 mmol,) at 5-10° C. The mixture was stirred at 15° C. for 15 mins. 88 (106 mg, 881 µmol) was added to the above mixture at 5-10° C. The mixture was stirred at 15° C. for 2 hrs. LCMS showed 59 was consumed completely and one main peak with desired MS was detected. The mixture was poured into ice-water (5 mL), the aqueous layer was extracted with DCM (5 mL*2), the combined organic layers were washed with brine (2 mL), dried over anhydrous Na₂SO₄, filtered and concentrated under reduced pressure to give a residue. The residue was purified by prep-TLC and lyophilized to give the desired product Compound 69 (17.0 mg, yield: 8.0%) as a white solid.

LCMS: m/z, 275.0 (M+H)⁺;

$^1$H NMR (400 MHz CDCl₃): δ 7.23 (s, 1H), 4.16 (d, J=10.8 Hz, 1H), 3.98 (d, J=11.2 Hz, 1H), 3.63 (s, 2H), 2.70 (s, 3H), 1.95 (s, 1H), 1.23 (s, 10H), 0.76-0.78 (t, J=4.8 Hz, 1H).

Functional Calcium Flux Assay Methodology

For functional assays, HEK293 cells stably expressing recombinant rat mGluR5 were seeded in 384-well plates and dye loaded using Fluo-8. Cells were then washed to remove the un-incorporated dye. Antagonist evaluation was performed following a 15 min incubation of the test compound followed by the addition of submaximal concentration of glutamate. Intracellular calcium ([Ca²⁺]$_i$) measurements were performed using a fluorometric imaging plate reader (FLIPR, Molecular Devices). The glutamate-evoked increase in [Ca²⁺]$_i$ in the presence of the test compounds was compared to the response to glutamate alone (the positive control). Antagonist inhibition curves were fitted with a 4-parameter logistic equation giving IC₅₀ values, and Hill coefficients using an iterative nonlinear curve fitting algorithm.

The tables below provide IC50 data in this assay. In the activity column, A=IC₅₀>1,000 and <5,000 nM; B=IC₅₀>500 and <1,000 nM and C=IC₅₀<500 nM.

TABLE 1

| # | Example Compound | Structure | IC50 value (FLIPR assay) |
|---|---|---|---|
| 1 | 1 | 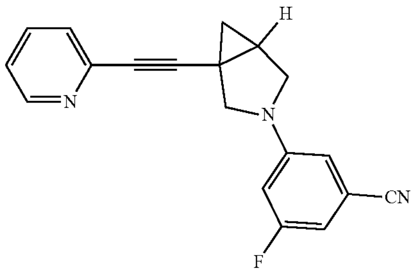 [SMILES: N#Cc1cc(F)cc(N2CC3CC3(C#Cc3ccccn3)C2)c1] | C |
| 2 | 2 | 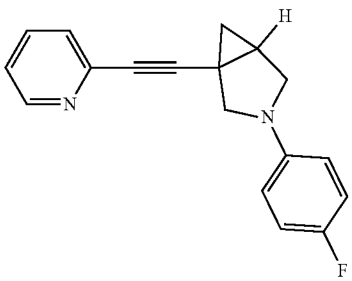 [SMILES: Fc1ccc(N2CC3CC3(C#Cc3ccccn3)C2)cc1] | C |
| 3 | 3 | 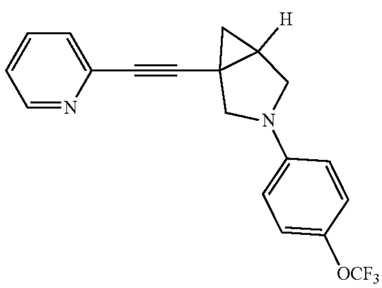 [SMILES: FC(F)(F)Oc1ccc(N2CC3CC3(C#Cc3ccccn3)C2)cc1] | A |
| 4 | 10 | 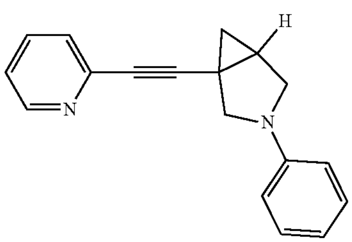 [SMILES: C(#CC12CC1CN(c1ccccc1)C2)c1ccccn1] | C |
| 5 | 16 | 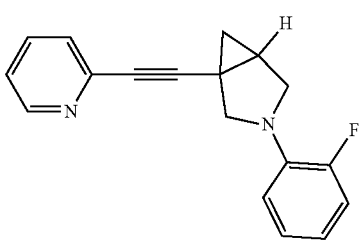 [SMILES: Fc1ccccc1N1CC2CC2(C#Cc2ccccn2)C1] | C |
| 6 | 17 | 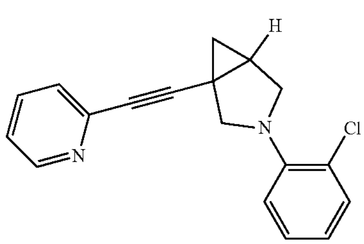 [SMILES: Clc1ccccc1N1CC2CC2(C#Cc2ccccn2)C1] | C |

TABLE 1-continued

| Example # | Compound | Structure | IC50 value (FLIPR assay) |
|---|---|---|---|
| 7 | 18 | 3-chlorophenyl-pyrrolidine pyridine alkyne | C |
| 8 | 19 | 4-chlorophenyl-pyrrolidine pyridine alkyne | B |
| 9 | 20 | 3-chloro-5-fluorophenyl-pyrrolidine pyridine alkyne | C |
| 10 | 21 | 2-fluoro-4-chlorophenyl-pyrrolidine pyridine alkyne | B |
| 11 | 22 | 3-fluoro-4-chlorophenyl-pyrrolidine pyridine alkyne | B |

TABLE 1-continued

| # | Example Compound | Structure | IC50 value (FLIPR assay) |
|---|---|---|---|
| 12 | 40 | 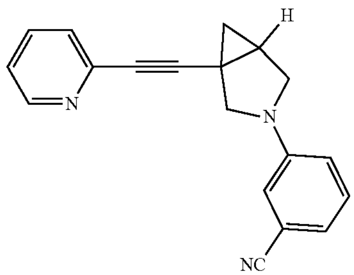 [SMILES: N#Cc1cccc(N2CC3CC3(C#Cc3ccccn3)C2)c1] | C |
| 13 | 45 | 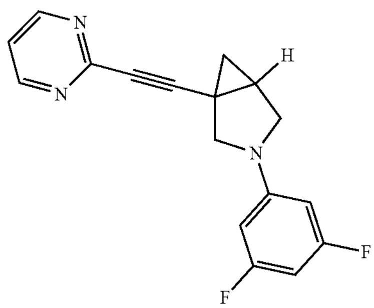 [SMILES: Fc1cc(F)cc(N2CC3CC3(C#Cc3ncccn3)C2)c1] | C |
| 14 | 46 | 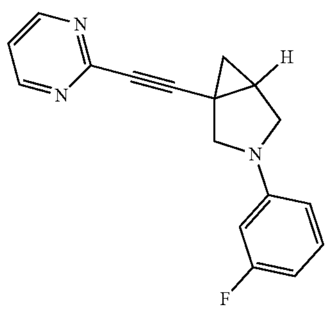 [SMILES: Fc1cccc(N2CC3CC3(C#Cc3ncccn3)C2)c1] | C |
| 15 | 47 | 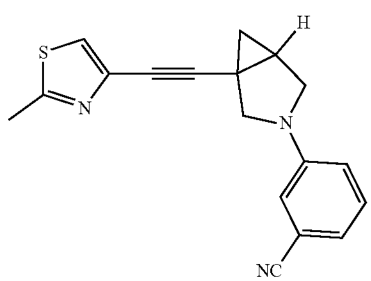 [SMILES: Cc1nc(C#CC23CC2CN(c2cccc(C#N)c2)C3)cs1] | C |
| 16 | 48 | 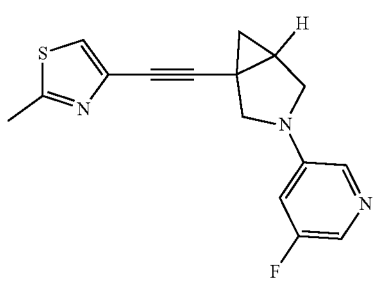 [SMILES: Cc1nc(C#CC23CC2CN(c2cncc(F)c2)C3)cs1] | C |

TABLE 1-continued

| Example # | Compound | Structure | IC50 value (FLIPR assay) |
|---|---|---|---|
| 17 | 62 | (pyrimidin-2-yl-ethynyl-azabicyclo[3.1.0]hexane with 3-cyanophenyl on N) | C |
| 18 | 4 | (pyridin-2-yl-ethynyl-azabicyclo[3.1.0]hexane with 5-fluoropyridin-3-yl on N) | C |
| 19 | 6 | (pyridin-2-yl-ethynyl-azabicyclo[3.1.0]hexane with 5-fluoropyridin-2-yl on N) | C |
| 20 | 23 | (pyridin-2-yl-ethynyl-azabicyclo[3.1.0]hexane with 4-cyanopyridin-2-yl on N) | C |
| 21 | 24 | (pyridin-2-yl-ethynyl-azabicyclo[3.1.0]hexane with 7-azaindol-6-yl on N) | A |

TABLE 1-continued

| # | Example Compound | Structure | IC50 value (FLIPR assay) |
|---|---|---|---|
| 22 | 25 | 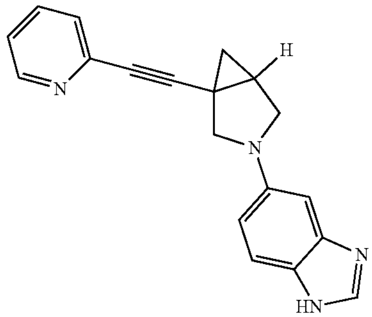 [SMILES: C(#CC12CC1CN(c1ccc3[nH]cnc3c1)C2)c1ccccn1] | A |
| 23 | 38 | 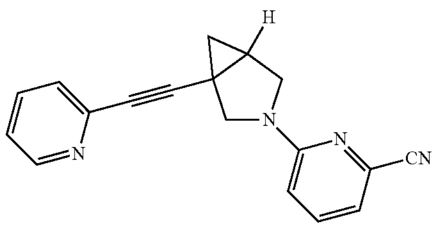 [SMILES: N#Cc1cccc(N2CC3CC3(C#Cc3ccccn3)C2)n1] | C |
| 24 | 43 | 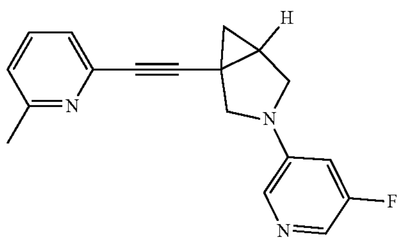 [SMILES: Cc1cccc(C#CC23CC2CN(c2cncc(F)c2)C3)n1] | C |
| 25 | 50 | 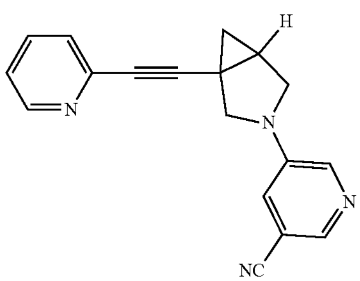 [SMILES: N#Cc1cncc(N2CC3CC3(C#Cc3ccccn3)C2)c1] | C |
| 26 | 63 | 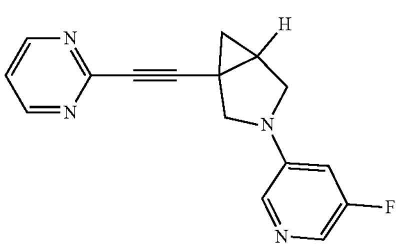 [SMILES: Fc1cncc(N2CC3CC3(C#Cc3ncccn3)C2)c1] | C |
| 27 | 5 | 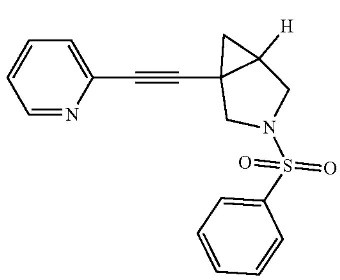 [SMILES: O=S(=O)(c1ccccc1)N1CC2CC2(C#Cc2ccccn2)C1] | C |

TABLE 1-continued

| # | Example Compound | Structure | IC50 value (FLIPR assay) |
|---|---|---|---|
| 28 | 26 | 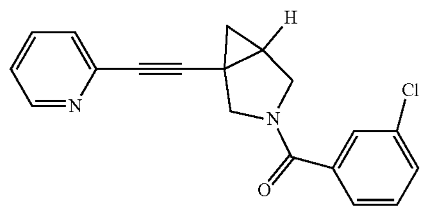 [SMILES: O=C(c1cccc(Cl)c1)N1CC2CC2(C#Cc2ccccn2)C1] | C |
| 29 | 27 | 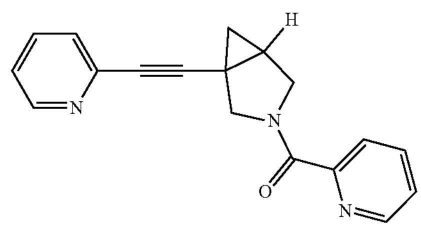 [SMILES: O=C(c1ccccn1)N1CC2CC2(C#Cc2ccccn2)C1] | C |
| 30 | 28 | 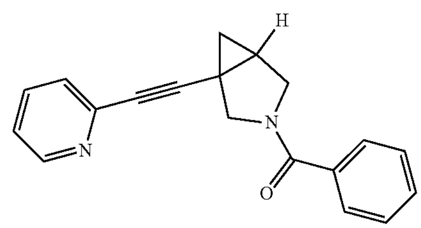 [SMILES: O=C(c1ccccc1)N1CC2CC2(C#Cc2ccccn2)C1] | C |
| 31 | 29 | 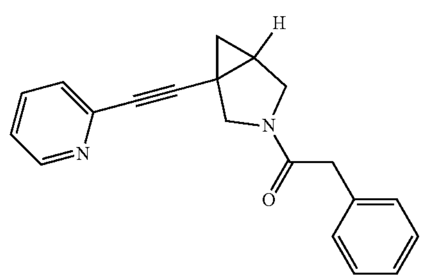 [SMILES: O=C(Cc1ccccc1)N1CC2CC2(C#Cc2ccccn2)C1] | C |
| 32 | 30 | 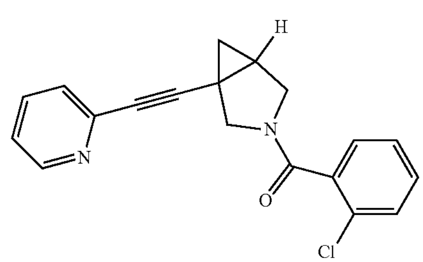 [SMILES: O=C(c1ccccc1Cl)N1CC2CC2(C#Cc2ccccn2)C1] | C |
| 33 | 31 | 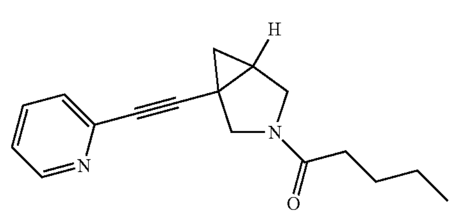 [SMILES: CCCCC(=O)N1CC2CC2(C#Cc2ccccn2)C1] | C |

TABLE 1-continued

| # | Example Compound | Structure | IC50 value (FLIPR assay) |
|---|---|---|---|
| 34 | 32 | (pyridin-2-ylethynyl-bicyclic amine with 3-phenylpropanoyl group) | C |
| 35 | 33 | (pyridin-2-ylethynyl-bicyclic amine with 4-chlorobenzoyl group) | C |
| 36 | 34 | (pyridin-2-ylethynyl-bicyclic amine with 3-chlorophenylsulfonyl group) | C |
| 37 | 35 | (pyridin-2-ylethynyl-bicyclic amine with 4-chlorophenylsulfonyl group) | C |
| 38 | 36 | (pyridin-2-ylethynyl-bicyclic amine with 2-chlorophenylsulfonyl group) | C |
| 39 | 37 | (pyridin-2-ylethynyl-bicyclic amine with 4-methylphenylsulfonyl group) | C |

TABLE 1-continued

| # | Example Compound | Structure | IC50 value (FLIPR assay) |
|---|---|---|---|
| 40 | 41 | 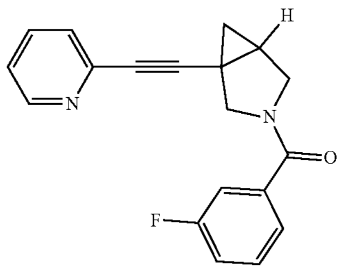 [SMILES: O=C(c1cccc(F)c1)N1CC2CC2(C#Cc2ccccn2)C1] | C |
| 41 | 42 | 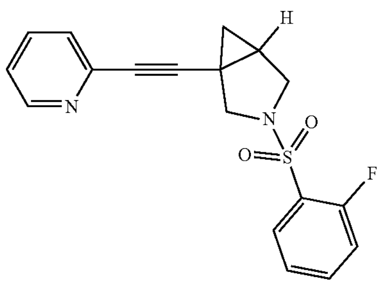 [SMILES: O=S(=O)(c1ccccc1F)N1CC2CC2(C#Cc2ccccn2)C1] | C |
| 42 | 44 | 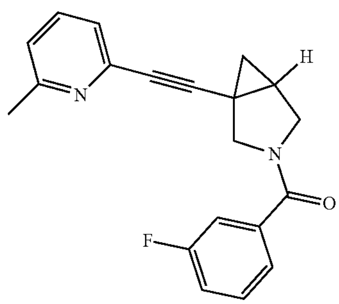 [SMILES: Cc1cccc(C#CC23CC2CN(C(=O)c2cccc(F)c2)C3)n1] | C |
| 43 | 49 | 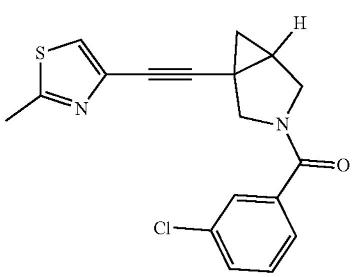 [SMILES: Cc1nc(C#CC23CC2CN(C(=O)c2cccc(Cl)c2)C3)cs1] | C |
| 44 | 51 | 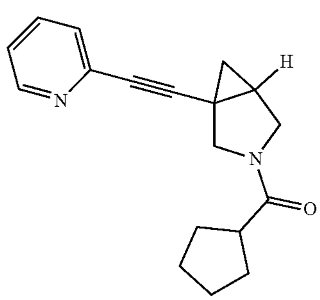 [SMILES: O=C(C1CCCC1)N1CC2CC2(C#Cc2ccccn2)C1] | C |

TABLE 1-continued
| Example # | Compound | Structure | IC50 value (FLIPR assay) |
|---|---|---|---|
| 45 | 52 | 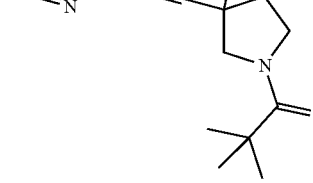 | C |
| 46 | 53 | 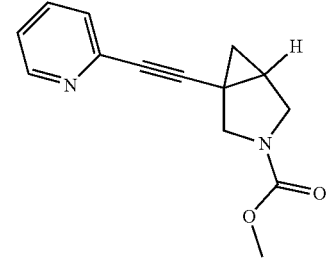 [SMILES: COC(=O)N1CC2CC2(C#Cc2ccccn2)C1] | C |
| 47 | 54 | 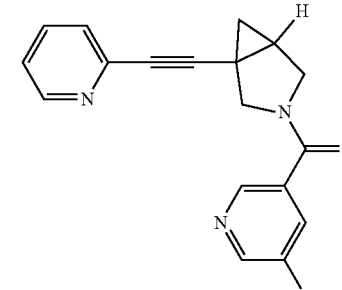 | C |
| 48 | 55 | 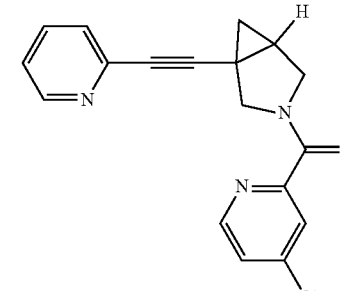 | C |
| 49 | 56 | 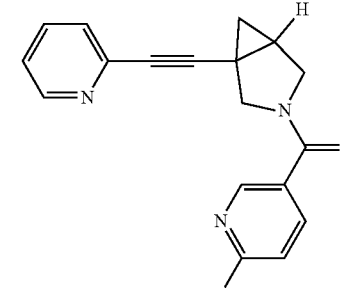 | C |

TABLE 1-continued

| Example # | Compound | Structure | IC50 value (FLIPR assay) |
|---|---|---|---|
| 50 | 61 | 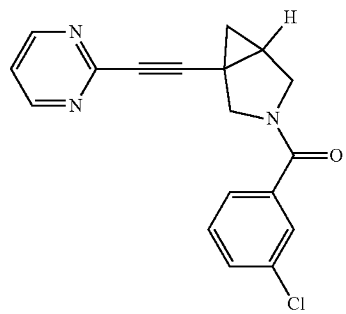 [SMILES: O=C(c1cccc(Cl)c1)N1CC2CC2(C#Cc2ncccn2)C1] | B |
| 51 | 64 | 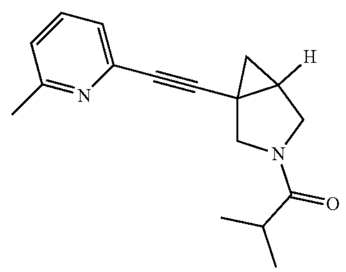 [SMILES: Cc1cccc(C#CC23CC2CN(C(=O)C(C)C)C3)n1] | C |
| 52 | 65 | 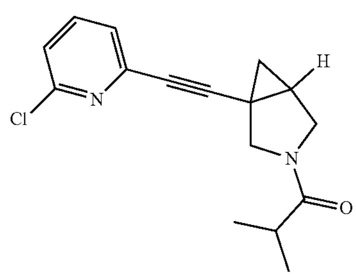 [SMILES: CC(C)C(=O)N1CC2CC2(C#Cc2cccc(Cl)n2)C1] | C |
| 53 | 66 | 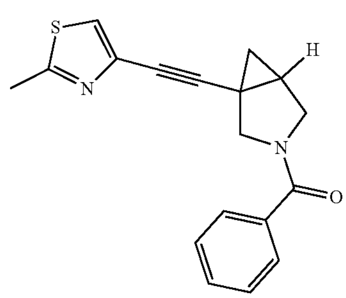 [SMILES: Cc1nc(C#CC23CC2CN(C(=O)c2ccccc2)C3)cs1] | C |
| 54 | 67 | 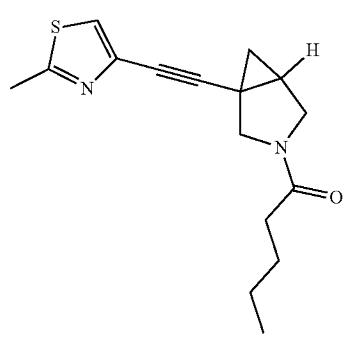 [SMILES: CCCCC(=O)N1CC2CC2(C#Cc2csc(C)n2)C1] | C |

TABLE 1-continued
| Example # | Compound | Structure | IC50 value (FLIPR assay) |
|---|---|---|---|
| 55 | 68 | 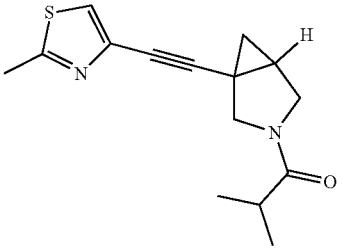 [SMILES: Cc1nc(C#CC23CC2CN(C(=O)C(C)C)C3)cs1] | C |
| 56 | 69 | 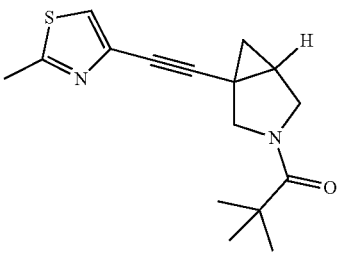 [SMILES: Cc1nc(C#CC23CC2CN(C(=O)C(C)(C)C)C3)cs1] | C |
| 57 | 57 | 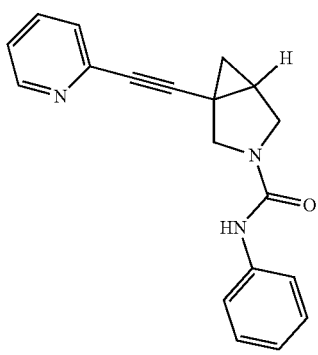 [SMILES: O=C(Nc1ccccc1)N1CC2CC2(C#Cc2ccccn2)C1] | B |
| 58 | 58 | 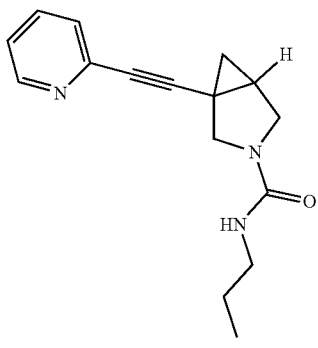 [SMILES: CCCNC(=O)N1CC2CC2(C#Cc2ccccn2)C1] | C |
| 59 | 59 | 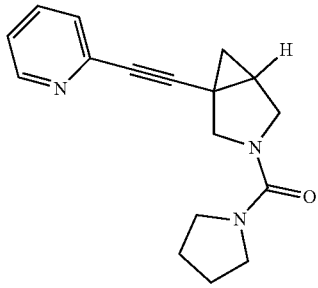 [SMILES: O=C(N1CCCC1)N1CC2CC2(C#Cc2ccccn2)C1] | C |

TABLE 1-continued

| # | Example Compound | Structure | IC50 value (FLIPR assay) |
|---|---|---|---|
| 60 | 60 | 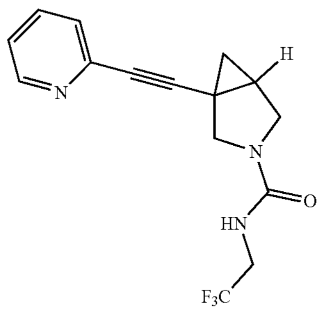 [SMILES: O=C(NCC(F)(F)F)N1CC2CC2(C#Cc2ccccn2)C1] | C |
| 61 | 7 | 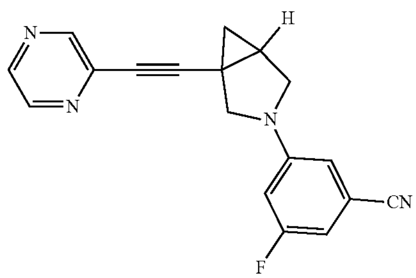 [SMILES: N#Cc1cc(F)cc(N2CC3CC3(C#Cc3cnccn3)C2)c1] | C |
| 62 | 8 | 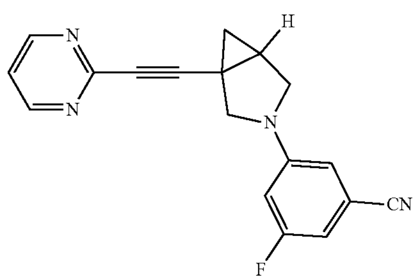 [SMILES: N#Cc1cc(F)cc(N2CC3CC3(C#Cc3ncccn3)C2)c1] | C |
| 63 | 9 | 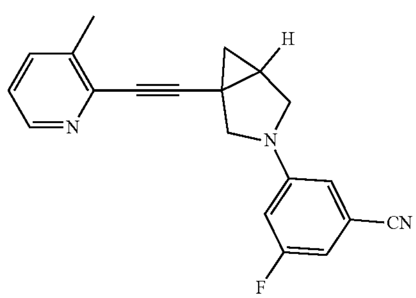 [SMILES: Cc1cccnc1C#CC12CC1CN(c1cc(F)cc(C#N)c1)C2] | A |
| 64 | 11 | 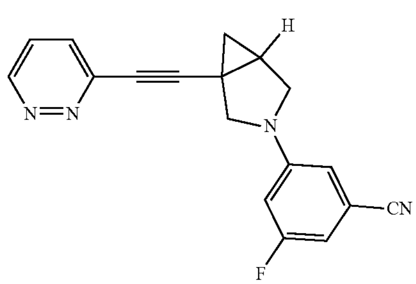 [SMILES: N#Cc1cc(F)cc(N2CC3CC3(C#Cc3cccnn3)C2)c1] | C |

TABLE 1-continued

| Example # | Compound | Structure | IC50 value (FLIPR assay) |
|---|---|---|---|
| 65 | 12 | 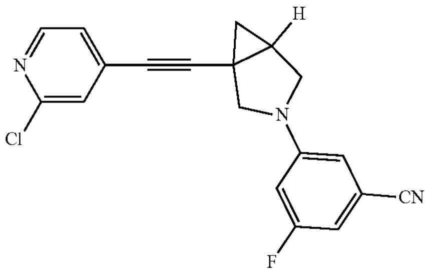 [SMILES: N#Cc1cc(F)cc(N2CC3CC3(C#Cc3ccnc(Cl)c3)C2)c1] | C |
| 66 | 13 | 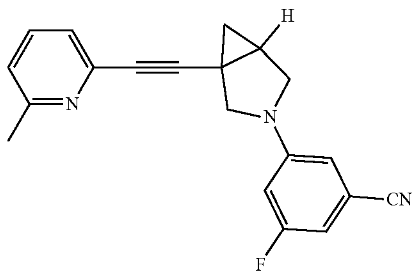 [SMILES: Cc1cccc(C#CC23CC2CN(c2cc(F)cc(C#N)c2)C3)n1] | C |
| 67 | 14 | 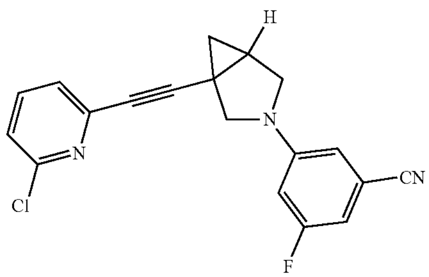 [SMILES: N#Cc1cc(F)cc(N2CC3CC3(C#Cc3cccc(Cl)n3)C2)c1] | C |
| 68 | 15 | 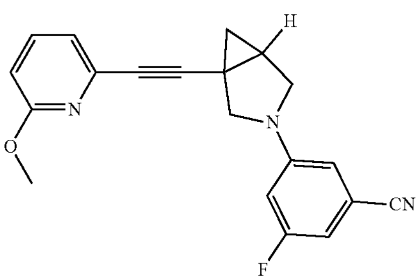 [SMILES: COc1cccc(C#CC23CC2CN(c2cc(F)cc(C#N)c2)C3)n1] | C |
| 69 | 39 | 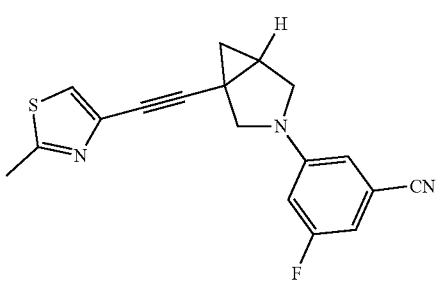 [SMILES: Cc1nc(C#CC23CC2CN(c2cc(F)cc(C#N)c2)C3)cs1] | C |

Example 11

Radioligand Binding Assay Using Membrane Preparations Expressing Rat mGluR5

The radiolabeled allosteric antagonist [$^3$H]-2-Methyl-6-(phenylethynyl)pyridine (MPEP, American Radiolabeled Chemical) was used to evaluate the ability of test compounds to interact with the MPEP site on mGluR5 as described in Rodriguez et al. [Mol Pharmacol 78:1105-1123, 2010]. Membranes were prepared from HEK293 cells expressing rat mGluR5. Radioligand binding assays were performed in 96-well plates (Corning) containing binding buffer (15 mM Tris pH 7.4, 120 mM NaCl, 100 mM KCl, 25 mM MgCl$_2$, 25 mM CaCl$_2$) with a final assay volume of 250 µL and 40 µg membranes/well.

Saturation isotherms were determined by incubation in presence of 12 increasing concentrations of [$^3$H]-MPEP (0.1-100 nM), while competition experiments were performed with a fixed concentration (4 nM) of [$^3$H]-MPEP in presence of 12 increasing concentrations of test compound (1-30,000 nM). Incubations were performed at 4° C. for 1 h. Nonspecific binding was estimated using 100 µM MTEP. At the end of incubation, membranes were filtered over GF/C filter plates (Perkin Elmer) presoaked in 0.1% BSA for 2 h at room temperature. Filter plates were then washed 5 times with ice cold buffer (15 mM Tris, pH 7.4 plus 0.1% BSA) using the Packard Filtermate Harvester and dried overnight in a 37° C. oven. Fifty L microscint 20 (PerkinElmer) were added to each well and the plates were incubated on an orbital shaker for 15 min before counting on a Microbeta Trilux for 2 min/well.

It is to be understood that the invention is not limited to the particular embodiments of the invention described above, as variations of the particular embodiments may be made and still fall within the scope of the appended claims.

The invention claimed is:

1. A compound of formula (I):

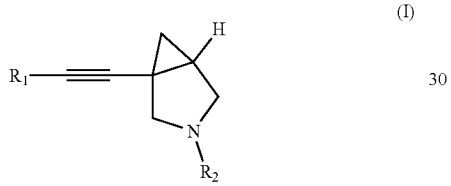

or a pharmaceutically acceptable salt thereof, wherein:
R$_1$ is a 5- to 10-membered monocyclic or bicyclic heteroaryl that contains 1, 2 or 3 heteroatoms selected from the group consisting of nitrogen, oxygen and sulfur, wherein the 5- to 10-membered monocyclic or bicyclic heteroaryl is optionally substituted with 1, 2 or 3 substituents independently selected from the group consisting of alkyl, halogen, —OH, —CN, —NO$_2$, —CF$_3$, —O—CF$_3$, —O-alkyl, —O-aryl, —S-alkyl, —S-aryl, —S(O)-alkyl, —S(O)-aryl, —S(O)$_2$-alkyl, —S(O)$_2$-aryl, —CH$_2$-aryl, aryl, heteroaryl, —O—CH$_2$-aryl, —N(CH$_3$)$_2$, cycloalkyl, heterocycloalkyl, —C(O)-alkyl, —C(O)-cycloalkyl, —C(O)-heterocycloalkyl, —C(O)-aryl, —C(O)— heteroaryl, —C(O)O-alkyl, —C(O)O-cycloalkyl, —C(O)O-heterocycloalkyl, —C(O)O-aryl, —C(O)O-heteroaryl, —C(O)NH-alkyl, —C(O)NH-cycloalkyl, —C(O)NH-heteroalkyl, —C(O)NH-aryl and —C(O)NH-heteroaryl, wherein the substituents may combine to form a 5-7 membered fused carbocyclyl or heterocyclyl; and
R$_2$ is —C(O)-alkyl, —C(O)-arylalkyl, —C(O)-aryl, —C(O)-heteroaryl, —S(O)$_2$-aryl, —S(O)$_2$-heteroaryl, —C(O)O-alkyl, —C(O)O-aryl, —C(O)O-arylalkyl or —C(O)—NH$_2$, wherein the aryl or heteroaryl portion of the —C(O)-arylalkyl, —C(O)-aryl, —C(O)-heteroaryl, —S(O)$_2$-aryl, —S(O)$_2$-heteroaryl, —C(O)O-aryl and —C(O)O-arylalkyl is optionally substituted with 1, 2 or 3 substituents independently selected from the group consisting of alkyl, halogen, —OH, —CN, —NO$_2$, —CF$_3$, —O—CF$_3$, —O-alkyl, —O-aryl, —S-alkyl, —S-aryl, —S(O)-alkyl, —S(O)-aryl, —S(O)$_2$-alkyl, —S(O)$_2$-aryl, —CH$_2$-aryl, heteroaryl, —O—CH$_2$-aryl, —N(CH$_3$)$_2$, cycloalkyl, heterocycloalkyl, —C(O)-alkyl, —C(O)-cycloalkyl, —C(O)-heterocycloalkyl, —C(O)-aryl, —C(O)-heteroaryl, —C(O)O-alkyl, —C(O)O-cycloalkyl, —C(O)O-heterocycloalkyl, —C(O)O-aryl, —C(O)O-heteroaryl, —C(O)NH—alkyl, —C(O)NH-cycloalkyl, —C(O)NH-heteroalkyl, —C(O)NH-aryl and —C(O)NH-heteroaryl, wherein the substituents may combine to form a 5-7 membered fused carbocyclyl or heterocyclyl; or R$_2$ is a 5- to 10-membered monocyclic or bicyclic heteroaryl that contains 1, 2 or 3 heteroatoms selected from the group consisting of nitrogen, oxygen and sulfur, wherein the 5- to 10-membered monocyclic or bicyclic heteroaryl is optionally substituted with 1, 2 or 3 substituents independently selected from the group consisting of alkyl, halogen, —OH, —CN, —NO$_2$, —CF$_3$, —O—CF$_3$, —O-alkyl, —O-aryl, —S-alkyl, —S-aryl, —S(O)-alkyl, —S(O)-aryl, —S(O)$_2$-alkyl, —S(O)$_2$-aryl, —CH$_2$-aryl, aryl, heteroaryl, —O—CH$_2$-aryl, —N(CH$_3$)$_2$, cycloalkyl, heterocycloalkyl, —C(O)-alkyl, —C(O)-cycloalkyl, —C(O)-heterocycloalkyl, —C(O)-aryl, —C(O)— heteroaryl, —C(O)O-alkyl, —C(O)O-cycloalkyl, —C(O)O-heterocycloalkyl, —C(O)O-aryl, —C(O)O-heteroaryl, —C(O)NH-alkyl, —C(O)NH-cycloalkyl, —C(O)NH-heteroalkyl, —C(O)NH-aryl and —C(O)NH-heteroaryl, wherein the substituents may combine to form a 5-7 membered fused carbocyclyl or heterocyclyl; or R$_2$ is a 5- to 10-membered monocyclic or bicyclic aryl, wherein the 5- to 10-membered monocyclic or bicyclic aryl is optionally substituted with 1, 2 or 3 substituents independently selected from the group consisting of alkyl, halogen, —OH, —CN, —NO$_2$, —CF$_3$, —O—CF$_3$, —O-alkyl, —O-aryl, —S-alkyl, —S-aryl, —S(O)-alkyl, —S(O)-aryl, —S(O)$_2$-alkyl, —S(O)$_2$-aryl, —CH$_2$-aryl, aryl, heteroaryl, —O—CH$_2$-aryl, —N(CH$_3$)$_2$, cycloalkyl, heterocycloalkyl, —C(O)-alkyl, —C(O)-cycloalkyl, —C(O)-heterocycloalkyl, —C(O)-aryl, —C(O)-heteroaryl, —C(O)O-alkyl, —C(O)O-cycloalkyl, —C(O)O-heterocycloalkyl, —C(O)O-aryl, —C(O)O-heteroaryl, —C(O)NH— alkyl, —C(O)NH-cycloalkyl, —C(O)NH-heteroalkyl, —C(O)NH-aryl and —C(O)NH-heteroaryl, wherein the substituents may combine to form a 5-7 membered fused carbocyclyl or heterocyclyl.

2. The compound according to claim 1, or a pharmaceutically acceptable salt thereof, wherein:
R$_1$ is a 5- to 6-membered monocyclic heteroaryl that contains 1, 2 or 3 heteroatoms selected from the group consisting of nitrogen, oxygen and sulfur, optionally substituted with 1 or 2 substituents; and
R$_2$ is —C(O)—C$_1$-C$_5$-alkyl, —C(O)—C$_1$-C$_5$-alkylaryl, —C(O)-aryl, —C(O)-heteroaryl, —C(O)O—C$_1$-C$_5$-alkyl, —C(O)O—C$_1$-C$_5$-arylalkyl or —S(O)$_2$-phenyl, wherein the aryl, phenyl or heteroaryl portion of the —C(O)—C$_1$-C$_5$-alkylaryl, —C(O)-aryl, —C(O)-heteroaryl, —C(O)O—C$_1$-C$_5$-arylalkyl and —S(O)$_2$-phenyl is optionally substituted; or R₂ is a 5- to 10-membered monocyclic or bicyclic heteroaryl that contains 1, 2 or 3 heteroatoms selected from the group consisting of nitrogen, oxygen and sulfur, wherein the 5- to 10-membered monocyclic or bicyclic heteroaryl is optionally substituted with 1 or 2 substituents; or R₂ is a 5- to 10-membered monocyclic or bicyclic aryl, wherein the 5- to 10-membered monocyclic or bicyclic aryl is optionally substituted with 1 or 2 substituents.

3. The compound according to claim 1, or a pharmaceutically acceptable salt thereof, wherein:

R₁ is selected from the group consisting of:

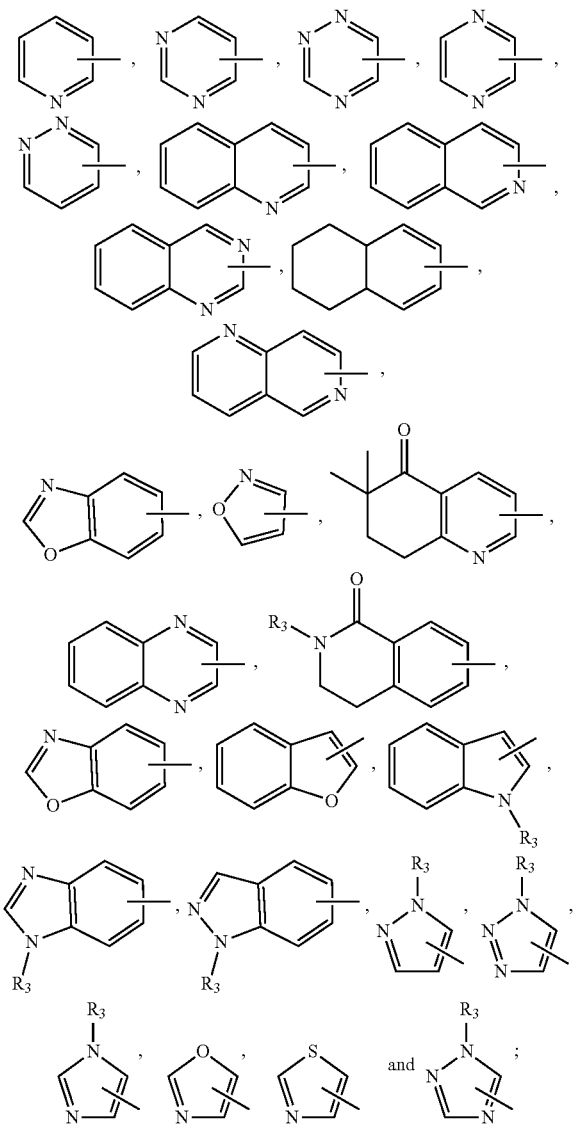

and

R₃ is —H or lower alkyl.

4. The compound according to claim 1, or a pharmaceutically acceptable salt thereof, wherein R₁ is optionally substituted thiazolyl, optionally substituted pyridin-4-yl, optionally substituted pyridazinyl, optionally substituted pyrimidinyl or optionally substituted pyrazinyl.

5. The compound according to claim 1, or a pharmaceutically acceptable salt thereof, wherein R₁ is optionally substituted pyridin-2-yl.

6. The compound according to claim 1, wherein the compound is selected from the group consisting of:
  3-fluoro-5-(1-(pyridin-2-ylethynyl)-3-azabicyclo[3.1.0]hexan-3-yl)benzonitrile,
  3-(4-fluorophenyl)-1-(pyridin-2-ylethynyl)-3-azabicyclo[3.1.0]hexane,
  1-(pyridin-2-ylethynyl)-3-(4-(trifluoromethoxy)phenyl)-3-azabicyclo[3.1.0]hexane,
  3-phenyl-1-(pyridin-2-ylethynyl)-3-azabicyclo[3.1.0]hexane,
  3-(2-fluorophenyl)-1-(pyridin-2-ylethynyl)-3-azabicyclo[3.1.0]hexane,
  3-(2-chlorophenyl)-1-(pyridin-2-ylethynyl)-3-azabicyclo[3.1.0]hexane,
  3-(3-chlorophenyl)-1-(pyridin-2-ylethynyl)-3-azabicyclo[3.1.0]hexane,
  3-(4-chlorophenyl)-1-(pyridin-2-ylethynyl)-3-azabicyclo[3.1.0]hexane,
  3-(3-chloro-5-fluorophenyl)-1-(pyridin-2-ylethynyl)-3-azabicyclo[3.1.0]hexane,
  3-(4-chloro-2-fluorophenyl)-1-(pyridin-2-ylethynyl)-3-azabicyclo[3.1.0]hexane,
  3-(4-chloro-3-fluorophenyl)-1-(pyridin-2-ylethynyl)-3-azabicyclo[3.1.0]hexane,
  3-(1-(pyridin-2-ylethynyl)-3-azabicyclo[3.1.0]hexan-3-yl)benzonitrile,
  3-(3,5-difluorophenyl)-1-(pyrimidin-2-ylethynyl)-3-azabicyclo[3.1.0]hexane,
  3-(3-fluorophenyl)-1-(pyrimidin-2-ylethynyl)-3-azabicyclo[3.1.0]hexane,
  3-(1-((2-methylthiazol-4-yl)ethynyl)-3-azabicyclo[3.1.0]hexan-3-yl)benzonitrile,
  4-(3-(5-fluoropyridin-3-yl)-3-azabicyclo[3.1.0]hexan-1-yl)ethynyl)-2-methylthiazole, and
  3-(1-(pyrimidin-2-ylethynyl)-3-azabicyclo[3.1.0]hexan-3-yl)benzonitrile,
or a pharmaceutically acceptable salt thereof.

7. The compound according to claim 1, wherein the compound is selected from the group consisting of:
  3-(5-fluoropyridin-3-yl)-1-(pyridin-2-ylethynyl)-3-azabicyclo[3.1.0]hexane,
  3-(5-fluoropyridin-2-yl)-1-(pyridin-2-ylethynyl)-3-azabicyclo[3.1.0]hexane,
  2-(1-(pyridin-2-ylethynyl)-3-azabicyclo[3.1.0]hexan-3-yl)isonicotinonitrile,
  5-(1-(pyridin-2-ylethynyl)-3-azabicyclo[3.1.0]hexan-3-yl)-1H-pyrrolo[3,2-b]pyridine,
  5-(1-(pyridin-2-ylethynyl)-3-azabicyclo[3.1.0]hexan-3-yl)-1H-benzo[d]imidazole,
  6-(1-(pyridin-2-ylethynyl)-3-azabicyclo[3.1.0]hexan-3-yl)picolinonitrile,
  3-(5-fluoropyridin-3-yl)-1-((6-methylpyridin-2-yl)ethynyl)-3-azabicyclo[3.1.0]hexane,
  5-(1-(pyridin-2-ylethynyl)-3-azabicyclo[3.1.0]hexan-3-yl)nicotinonitrile, and
  3-(5-fluoropyridin-3-yl)-1-(pyrimidin-2-ylethynyl)-3-azabicyclo[3.1.0]hexane,
or a pharmaceutically acceptable salt thereof.

8. The compound according to claim 1, wherein the compound is selected from the group consisting of:
  3-(phenylsulfonyl)-1-(pyridin-2-ylethynyl)-3-azabicyclo[3.1.0]hexane,
  (3-chlorophenyl)(1-(pyridin-2-ylethynyl)-3-azabicyclo[3.1.0]hexan-3-yl)methanone,
  pyridin-2-yl(1-(pyridin-2-ylethynyl)-3-azabicyclo[3.1.0]hexan-3-yl)methanone, phenyl(1-(pyridin-2-ylethynyl)-3-azabicyclo[3.1.0]
hexan-3-yl)methanone,
2-phenyl-1-(1-(pyridin-2-ylethynyl)-3-azabicyclo[3.1.0]
hexan-3-yl)ethanone,
(2-chlorophenyl)(1-(pyridin-2-ylethynyl)-3-azabicyclo
[3.1.0]hexan-3-yl)methanone,
1-(1-(pyridin-2-ylethynyl)-3-azabicyclo[3.1.0]hexan-3-
yl)pentan-1-one,
3-phenyl-1-(1-(pyridin-2-ylethynyl)-3-azabicyclo[3.1.0]
hexan-3-yl)propan-1-one,
(4-chlorophenyl)(1-(pyridin-2-ylethynyl)-3-azabicyclo
[3.1.0]hexan-3-yl)methanone,
3-((3-chlorophenyl)sulfonyl)-1-(pyridin-2-ylethynyl)-3-
azabicyclo[3.1.0]hexane,
3-((4-chlorophenyl)sulfonyl)-1-(pyridin-2-ylethynyl)-3-
azabicyclo[3.1.0]hexane,
3-((2-chlorophenyl)sulfonyl)-1-(pyridin-2-ylethynyl)-3-
azabicyclo[3.1.0]hexane,
1-(pyridin-2-ylethynyl)-3-tosyl-3-azabicyclo[3.1.0]
hexane,
(3-fluorophenyl)(1-(pyridin-2-ylethynyl)-3-azabicyclo
[3.1.0]hexan-3-yl)methanone,
3-((2-fluorophenyl)sulfonyl)-1-(pyridin-2-ylethynyl)-3-
azabicyclo[3.1.0]hexane,
(3-fluorophenyl)(1-((6-methylpyridin-2-yl)ethynyl)-3-
azabicyclo[3.1.0]hexan-3-yl)methanone,
(3-chlorophenyl)(1-((2-methylthiazol-4-yl)ethynyl)-3-
azabicyclo[3.1.0]hexan-3-yl)methanone,
cyclopentyl(1-(pyridin-2-ylethynyl)-3-azabicyclo[3.1.0]
hexan-3-yl)methanone,
2,2-dimethyl-1-(1-(pyridin-2-ylethynyl)-3-azabicyclo
[3.1.0]hexan-3-yl)propan-1-one,
methyl-1-(pyridin-2-ylethynyl)-3-azabicyclo[3.1.0]
hexane-3-carboxylate
(5-chloropyridin-3-yl)-(1-(pyridin-2-ylethynyl)-3-azabi-
cyclo[3.1.0]hexan-3-yl)methanone,
(4-chloropyridin-2-yl)(1-(pyridin-2-ylethynyl)-3-azabi-
cyclo[3.1.0]hexan-3-yl)methanone,
(6-chloropyridin-3-yl)(1-(pyridin-2-ylethynyl)-3-azabi-
cyclo[3.1.0]hexan-3-yl)methanone,
(3-chlorophenyl)(1-(pyrimidin-2-ylethynyl)-3-azabicyclo
[3.1.0]hexan-3-yl)methanone,
2-methyl-1-(1-((6-methylpyridin-2-yl)ethynyl)-3-azabi-
cyclo[3.1.0]hexan-3-yl)propan-1-one,
1-(1-((6-chloropyridin-2-yl)ethynyl)-3-azabicyclo[3.1.0]
hexan-3-yl)-2-methylpropan-1-one,
(1-((2-methylthiazol-4-yl)ethynyl)-3-azabicyclo[3.1.0]
hexan-3-yl)(phenyl)methanone,
1-(1-((2-methylthiazol-4-yl)ethynyl)-3-azabicyclo[3.1.0]
hexan-3-yl)pentan-1-one,
2-methyl-1-(1-((2-methylthiazol-4-yl)ethynyl)-3-azabi-
cyclo[3.1.0]hexan-3-yl)propan-1-one, and
2,2-dimethyl-1-(1-((2-methylthiazol-4-yl)ethynyl)-3-
azabicyclo[3.1.0]hexan-3-yl)propan-1-one,
or a pharmaceutically acceptable salt thereof.

9. The compound according to claim 1, wherein the compound is selected from the group consisting of:
3-fluoro-5-(1-(pyrazin-2-ylethynyl)-3-azabicyclo[3.1.0]
hexan-3-yl)benzonitrile,
3-fluoro-5-(1-(pyrimidin-2-ylethynyl)-3-azabicyclo
[3.1.0]hexan-3-yl)benzonitrile,
3-fluoro-5-(1-((3-methylpyridin-2-yl)ethynyl)-3-azabicy-
clo[3.1.0]hexan-3-yl)benzonitrile,
3-fluoro-5-(1-(pyridazin-3-ylethynyl)-3-azabicyclo
[3.1.0]hexan-3-yl)benzonitrile,
3-(1-((2-chloropyridin-4-yl)ethynyl)-3-azabicyclo[3.1.0]
hexan-3-yl)-5-fluorobenzonitrile,
3-fluoro-5-(1-((6-methylpyridin-2-yl)ethynyl)-3-azabicy-
clo[3.1.0]hexan-3-yl)benzonitrile,
3-(1-(6-chloropyridin-2-yl)-3-azabicyclo[3.1.0]hexan-3-
yl)-5-fluorobenzonitrile,
3-fluoro-5-(1-((6-methoxypyridin-2-yl)ethynyl)-3-azabi-
cyclo[3.1.0]hexan-3-yl)benzonitrile, and
3-fluoro-5-(1-((2-methylthiazol-4-yl)ethynyl)-3-azabicy-
clo[3.1.0]hexan-3-yl)benzonitrile,
or a pharmaceutically acceptable salt thereof.

10. A pharmaceutical composition comprising a compound according to claim 1, or a pharmaceutically acceptable salt thereof, and a pharmaceutically acceptable carrier or diluent.

11. A pharmaceutical composition comprising a compound according to claim 6, or a pharmaceutically acceptable salt thereof, and a pharmaceutically acceptable carrier or diluent.

12. A pharmaceutical composition comprising a compound according to claim 7, or a pharmaceutically acceptable salt thereof, and a pharmaceutically acceptable carrier or diluent.

13. A pharmaceutical composition comprising a compound according to claim 8, or a pharmaceutically acceptable salt thereof, and a pharmaceutically acceptable carrier or diluent.

14. A pharmaceutical composition comprising a compound according to claim 9, or a pharmaceutically acceptable salt thereof, and a pharmaceutically acceptable carrier or diluent.

15. A method for antagonizing metabotropic glutamate receptor 5 activity in a subject, comprising administering to the subject a compound according to claim 1, or a pharmaceutically acceptable salt thereof.

16. A method for antagonizing metabotropic glutamate receptor 5 activity in a subject, comprising administering to the subject a compound according to claim 6, or a pharmaceutically acceptable salt thereof.

17. A method for antagonizing metabotropic glutamate receptor 5 activity in a subject, comprising administering to the subject a compound according to claim 7, or a pharmaceutically acceptable salt thereof.

18. A method for antagonizing metabotropic glutamate receptor 5 activity in a subject, comprising administering to the subject a compound according to claim 8, or a pharmaceutically acceptable salt thereof.

19. A method for antagonizing metabotropic glutamate receptor 5 activity in a subject, comprising administering to the subject a compound according to claim 9, or a pharmaceutically acceptable salt thereof.

20. A method for antagonizing metabotropic glutamate receptor 5 activity in a subject, comprising administering to the subject a pharmaceutical composition according to claim 10.

21. A compound selected from the group consisting of:
N-phenyl-1-(pyridin-2-ylethynyl)-3-azabicyclo[3.1.0]
hexane-3-carboxamide,
N-propyl-1-(pyridin-2-ylethynyl)-3-azabicyclo[3.1.0]
hexane-3-carboxamide,
(1-(pyridin-2-ylethynyl)-3-azabicyclo[3.1.0]hexan-3-yl)
(pyrrolidin-1-yl)methanone, and
1-(pyridin-2-ylethynyl)-N-(2,2,2-trifluoroethyl)-3-azabi-
cyclo[3.1.0]hexane-3-carboxamide,
or a pharmaceutically acceptable salt thereof.

22. A pharmaceutical composition comprising a compound according to claim 21, or a pharmaceutically acceptable salt thereof, and a pharmaceutically acceptable carrier or diluent.

23. A method for antagonizing metabotropic glutamate receptor 5 activity in a subject, comprising administering to the subject a compound according to claim 21, or a pharmaceutically acceptable salt thereof.

24. A method for antagonizing metabotropic glutamate receptor 5 activity in a subject, comprising administering to the subject a pharmaceutical composition according to claim 22.

* * * * *